US012629523B2

(12) United States Patent
Young

(10) Patent No.: US 12,629,523 B2
(45) Date of Patent: May 19, 2026

(54) INTRAVAGINAL ELECTRICAL STIMULATION DEVICE FOR TREATING FEMALE PELVIC PAIN

(71) Applicant: Ives, LLC, Annapolis, MD (US)

(72) Inventor: Erik B. Young, Annapolis, MD (US)

(73) Assignee: Ives, LLC, Annapolis, MD (US)

( * ) Notice: Subject to any disclaimer, the term of this patent is extended or adjusted under 35 U.S.C. 154(b) by 320 days.

(21) Appl. No.: 18/241,552

(22) Filed: Sep. 1, 2023

(65) Prior Publication Data

US 2024/0050748 A1    Feb. 15, 2024

Related U.S. Application Data

(63) Continuation-in-part of application No. 17/504,689, filed on Oct. 19, 2021, now Pat. No. 11,752,340.
(Continued)

(51) Int. Cl.
*A61N 1/36*         (2006.01)
*A61N 1/05*         (2006.01)
(Continued)

(52) U.S. Cl.
CPC ....... *A61N 1/36071* (2013.01); *A61N 1/0524* (2013.01); *A61N 1/36153* (2013.01);
(Continued)

(58) Field of Classification Search
CPC .. A61N 1/0456; A61N 1/0521; A61N 1/0524; A61N 1/36007; A61N 1/36034;
(Continued)

(56) References Cited

U.S. PATENT DOCUMENTS 4,106,511 A    8/1978  Erlandsson
4,580,578 A    4/1986  Barsom
(Continued)

FOREIGN PATENT DOCUMENTS

CN        104436437 A    3/2015
CN        105848710 A    8/2016
(Continued)

OTHER PUBLICATIONS

Allon, The role of neuromuscular electrical stimulation in the rehabilitation of the pelvic floor muscles, British Journal of Nursing, vol. 28, No. 15, pp. 968-974, 2019.
(Continued)

*Primary Examiner* — Amanda K Hulbert
(74) *Attorney, Agent, or Firm* — Grady L. White; Potomac Law Group, PLLC

(57)              ABSTRACT

An intravaginal electrical stimulation device for treating pelvic pain in a female patient includes, in one embodiment, a set of intravaginal components comprising a frame, at least one pair of paracervical electrodes, an intravaginal capsule, a socket in the proximal end of the intravaginal capsule, an electrode plug that plugs into the socket, and connecting wires that electrically couple the electrode plug to the paracervical electrodes. The intravaginal components are designed to inserted into the patient's vagina so that one or more electrodes are in direct contact with the vaginal epithelium in the lateral vaginal fornices. In some embodiments, a cutaneous electrode may be included to be attached to the skin of the female patient. A microprocessor and an electrical stimulation generator are operable to cause low-voltage electrical current to flow through the intravaginal electrodes, the cutaneous electrode, or both, to create one or more electrical fields that neuromodulate the intrapelvic nerves of the patient. An external controller, which commu-
(Continued)

nicates with the intravaginal components over a wireless data communications channel, sends instructions to and receives status updates from the microprocessor inside the intravaginal capsule. In some embodiments, the electrical stimulation generator is located inside an external electrical stimulator generator (EESG) worn outside the body, instead of being located in an intravaginally worn intravaginal capsule, and the EESG is electrically coupled to the intravaginal components via one or more connecting wires that pass through the orifice of the female patient's vagina.

11 Claims, 41 Drawing Sheets

Related U.S. Application Data

(60) Provisional application No. 63/104,588, filed on Oct. 23, 2020.

(51) Int. Cl.
    *A61N 1/372* (2006.01)
    *A61N 1/40* (2006.01)

(52) U.S. Cl.
    CPC ..... *A61N 1/37223* (2013.01); *A61N 1/37247* (2013.01); *A61N 1/40* (2013.01)

(58) Field of Classification Search
    CPC ............ A61N 1/36071; A61N 1/36153; A61N 1/37223; A61N 1/37247; A61N 1/40
    See application file for complete search history.

(56) References Cited

U.S. PATENT DOCUMENTS

| | | | |
|---|---|---|---|
| 5,800,501 | A | 9/1998 | Sherlock |
| 5,871,533 | A | 2/1999 | Boutos |
| 6,055,456 | A | 4/2000 | Gerber |
| 6,185,465 | B1 | 2/2001 | Mo et al. |
| 6,862,480 | B2 | 3/2005 | Cohen et al. |
| 8,634,920 | B2 | 1/2014 | Hagege |
| 8,644,938 | B2 | 2/2014 | Craggs |
| 8,805,509 | B2 | 8/2014 | Boyd et al. |
| 8,914,111 | B2 | 12/2014 | Haessler |
| 9,358,383 | B2 | 6/2016 | Boyd et al. |
| 9,737,707 | B2 | 8/2017 | Haessler et al. |
| 9,999,490 | B2 | 6/2018 | Rosen et al. |
| 10,016,599 | B2 | 7/2018 | Lockwood et al. |
| 10,105,531 | B2 | 10/2018 | White et al. |
| 11,027,120 | B2 | 6/2021 | Peddicord |
| 11,110,269 | B2 | 9/2021 | Gregson |

| | | | |
|---|---|---|---|
| 2006/0036138 | A1 | 2/2006 | Heller et al. |
| 2009/0270963 | A1 | 10/2009 | Pelger et al. |
| 2011/0009692 | A1 | 1/2011 | Gross |
| 2013/0225922 | A1 | 8/2013 | Schentag et al. |
| 2013/0261702 | A1 | 10/2013 | Garfield et al. |
| 2013/0331905 | A1 | 12/2013 | Haessler |
| 2014/0058474 | A1 | 2/2014 | Haessler |
| 2016/0235978 | A1 | 8/2016 | Haessler |
| 2017/0065222 | A1 | 3/2017 | Egorov |
| 2018/0185641 | A1 | 7/2018 | Peled |
| 2021/0030464 | A1 | 2/2021 | Na |

FOREIGN PATENT DOCUMENTS

| | | |
|---|---|---|
| CN | 206518771 U | 9/2017 |
| CN | 206631014 U | 11/2017 |
| CN | 111801072 A | 10/2020 |
| EP | 0963217 B1 | 12/2004 |
| JP | 3125942 U | 10/2006 |
| JP | 2018064727 A | 4/2018 |
| KR | 200254852 Y1 | 12/2001 |
| WO | 9517922 A2 | 7/1995 |
| WO | 1995017922 A2 | 7/1995 |
| WO | 2012058289 A2 | 5/2012 |
| WO | 2013185121 A1 | 12/2013 |
| WO | 2019084469 A1 | 5/2019 |

OTHER PUBLICATIONS

Boston Scientific, "mySCS A Personalized and Connected SCS Experience," product brochure, https://www.bostonscientific.com/en-US/products/spinal-cord-stimulator-systems/myscs.html, 2021.
Boston Scientific, "Precision Novi Primary Cell Spinal Cord Stimulator System," product brochure, https://www.bostonscientific.com/en-US/products/spinal-cord-stimulator-systems/precision_novi.html, 2021.
Boston Scientific, "SCS Competitive Adapters & Connectors," product brochure, https://www.bostonscientific.com/en-US/products/spinal-cord-stimulator-systems/adapters-and-connectors.html, 2021.
Boston Scientific, "SCS Lead Portfolio," product brochure, https://www.bostonscientific.com/en-US/products/spinal-cord-stimulator-systems/scs_lead_portfolio.html, 2021.
Boston Scientific, "Spectra WaveWriter, Spinal Cord Stimulator System," product brochure, https://www.bostonscientific.com/en-US/products/spinal-cord-stimulator-systems/spectra-wavewriter.html, 2021.
Lempka et al., "Innovations in spinal cord stimulation for pain," Curr. Opin. Biomed. Eng., vol. 8, pp. 51-60, Dec. 2018.
McKenzie-Brown, "Spinal cord stimulation: Placement and Management," UpToDate, 2020, https://www.uptodate.com/contents/spinal-cord-stimulation-placement-and-management/print?source=autocomplete&index=~2&search=spinl%5Cal%E2%80%A6.
Unkown, "Sacral nerve stimulation," Wikipedia, Feb. 2021.

Body Planes and Terms of Relationship

Midline Sectional View of a Female Pelvis

Superior View of the Pelvic Viscera

Superior View of the Pelvic Floor with
Uterus and Peritoneum Removed

IVES Device - Perspective View
(as seen from a left, distal and anterior- lateral point of view)

101

Proximal End

Left Paracevical Electrode

110

Left Lateral

Proximal Portion of Frame

112

104

Electrode plug

110

Proximal End of IVC

112

108

108

106

104

Right Lateral

Distal End

IVES Device - Perspective View
(as seen from a left, proximal and anterior- lateral point of view)

Right Lateral

Proximal End

Proximal End
of IVC

Proximal Portion of Frame

Distal End

Left Lateral

IVES Device – Side View

Anterior

Proximal End

Proximal Portion of Frame (location of paracervical electrode(s) - not shown)

Posterior

Distal End

IVES Device – Top View

Right Lateral

101

Proximal Portion of Frame
(location of paracervical
electrode(s) – not shown)

102

110

124

110

Proximal
End

Proximal End
of IVC

124

Left Lateral

106

108

106

104

Distal
End

IVES Device – Transverse Cross-Section View
(view from distal end)

Anterior

Posterior

101

104

106

108

116

118

102

118

118

116

106

104

Frame
(Left Letral Portion)

Frame
(Right Letral Portion)

IVES Device - Longitudinal Cross-Section View

101

104

108

102

106

Distal End
of Frame

104

Proximal Portion of Frame
(location of paracervical
electrode(s) - not shown)

Intravaginal Capsule (IVC) - Orthogonal Cross-Section View

Intravaginal Capsule (IVC) - Distal End On View

Intravaginal Capsule (IVC) - Proximal End On View

Schematic Relationship of the IVES Device to Female Pelvic Structures
Longitudinal Cross Section View IVES Device In-Situ – Midline Section View

102

Proximal End of Frame in the
Posterior Vaginal Fornix
Uterine Cervix
Proximal End of IVC

146

108

104

Distal End of
Frame

142

141

IVES Device In-situ
(Anterior Transverse Section View)

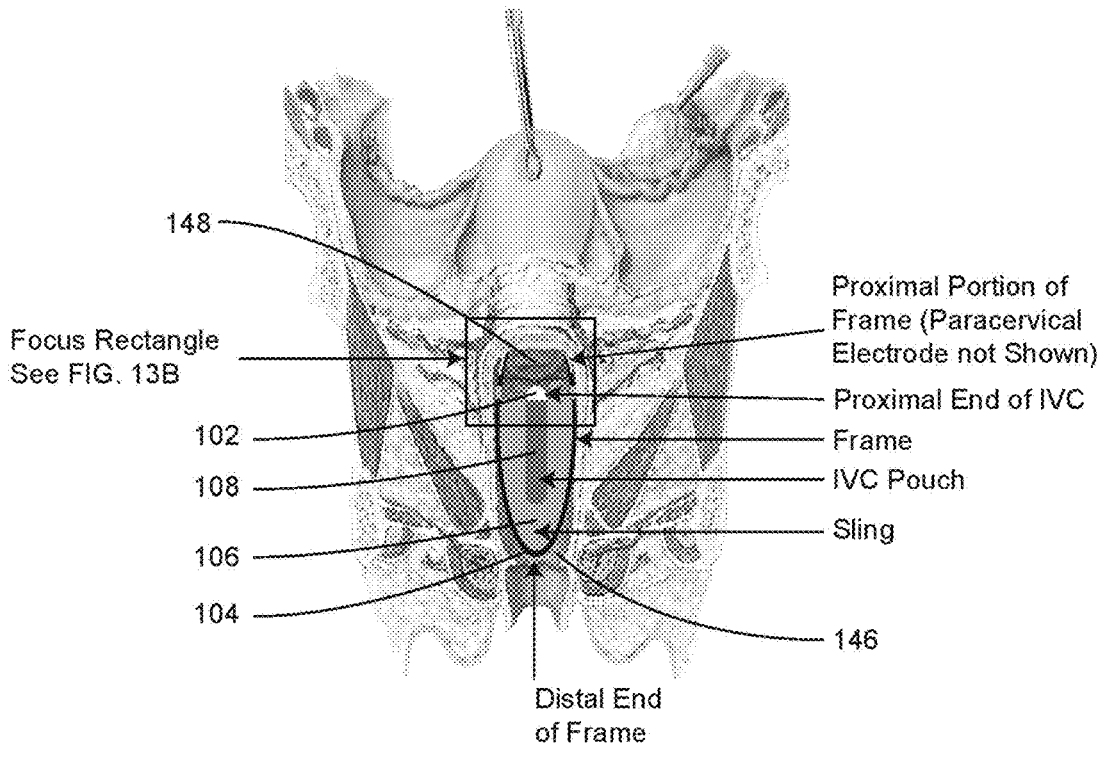

148

Focus Rectangle
See FIG. 13B

102

108

106

104

Proximal Portion of
Frame (Paracervical
Electrode not Shown)

Proximal End of IVC
Frame

IVC Pouch

Sling

146

Distal End
of Frame

FIG. 13A

IVES Device In-situ Enlarge Anterior Transverse
Sectional View of Upper Vagina and Uterine Cervix

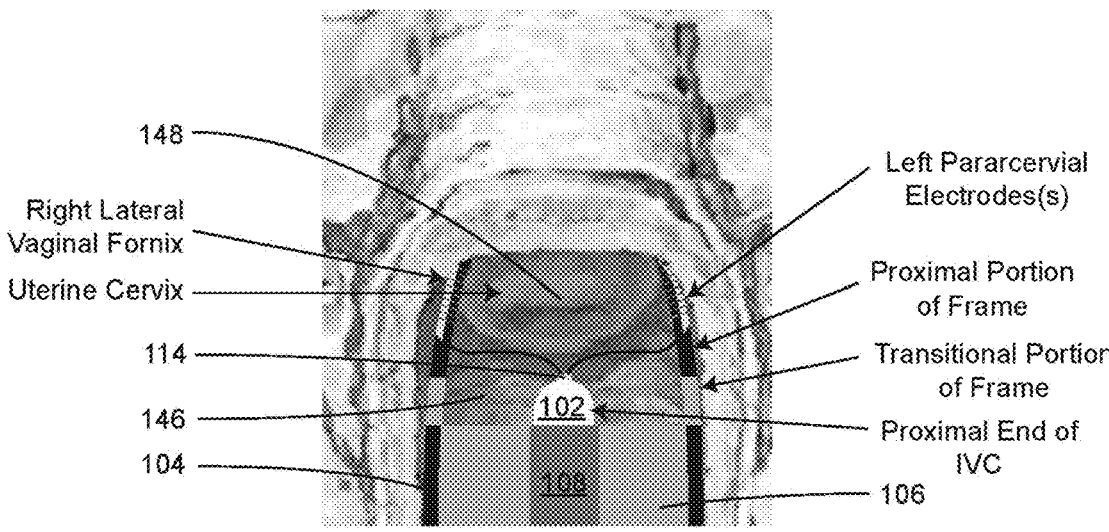

148

Right Lateral
Vaginal Fornix

Uterine Cervix

114

146

104

Left Pararcervial
Electrodes(s)

Proximal Portion
of Frame

Transitional Portion
of Frame

Proximal End of
IVC

Electrode Unit

Single Electrical Stimulation Circuit

Electrical Stimulation Circuit No. 1

Electrical Stimulation Circuit No. 2

Two Electrical Stimulation Units

Components of a pair of electrode units
compromising and electrical stimulation circuit Detailed Cross-Sectional View of the
Electrode Plug and Female Contact Detailed Cross-Sectional View of the Socket with Electrode Plug Inserted Proximal End Positioning of the paracervical electrodes in an embodiment of the IVES device
where one pair of electrode units creates a single electrical stimulation circuit Left Paracervical
Electrode Right Paracervical
Electrode Positioning of the paracervical electrodes when two pairs of electrode units
are used to create two electrical stimulation circuits Location of the paracervical Representation of a woman showing locations of
IVES device components in one embodiment Primary component of an IVES device using an external electrical stimulation generator and a pair of paracervical electrodes Primary components of an IVES device using an external electrical
stimulation generator, a paracervical electrode and a cutaneous electrode Primary components of an IVES device using an intravaginal capsule as the electrical stimulation generator, a paracervical electrode and a cutaneous electrode

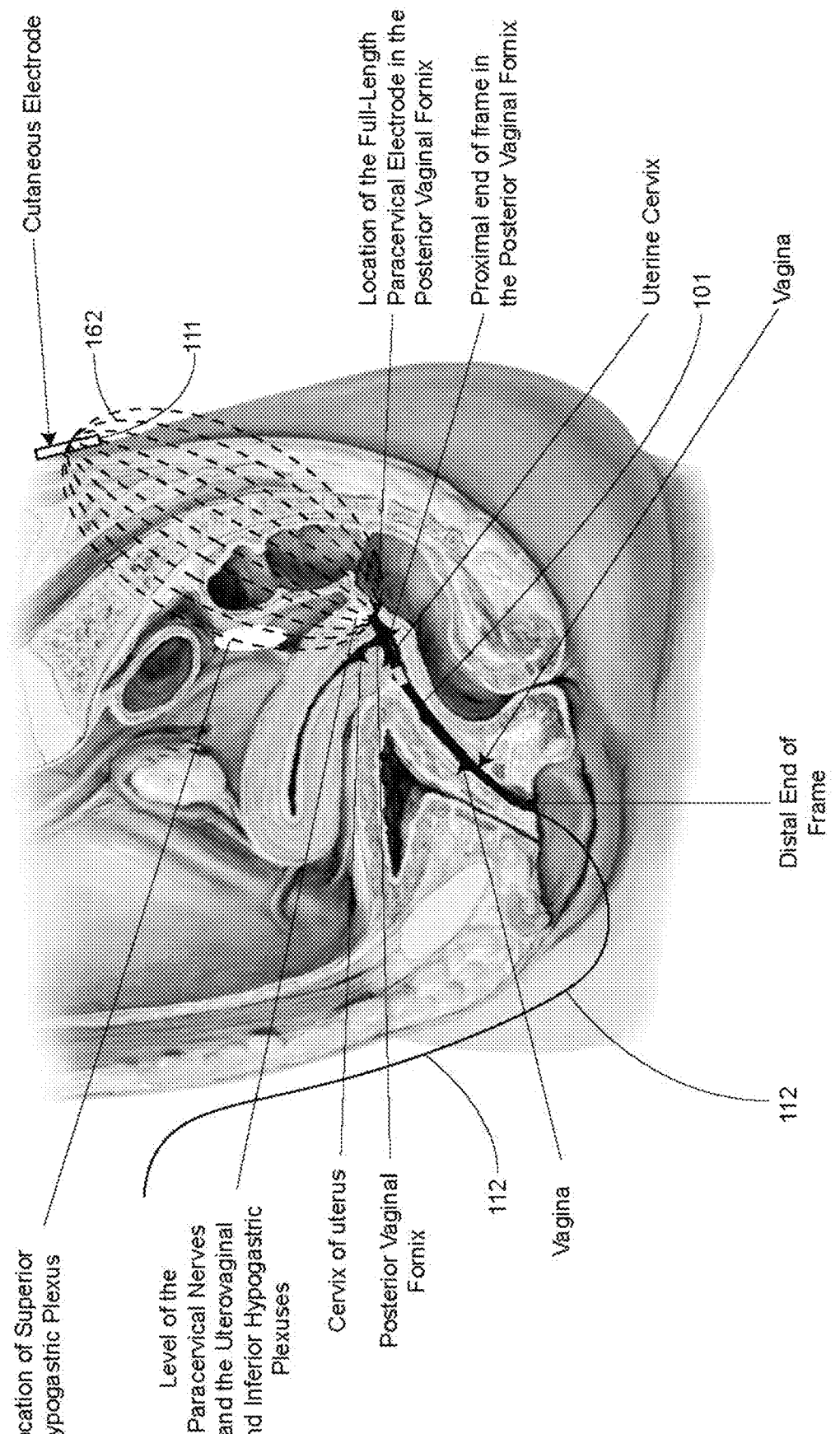

Cutaneous Electrode

Location of the Full-Length
Paracervical Electrode in the
Posterior Vaginal Fornix Proximal end of frame in
the Posterior Vaginal Fornix Uterine Cervix

101

Vagina

162

111

Location of Superior
Hypogastric Plexus

Level of the
Paracervical Nerves
and the Uterovaginal
and Inferior Hypogastric
Plexuses Cervix of uterus Posterior Vaginal
Fornix

112

Vagina

Distal End of
Frame

112

Electrical field created by a full length paracervical electrode ad a cutaneous electrode (side view)

FIG. 35

INTRAVAGINAL ELECTRICAL STIMULATION DEVICE FOR TREATING FEMALE PELVIC PAIN

FIELD OF THE INVENTION

Embodiments of the present invention relate generally to methods and devices for treating pelvic pain in women, and more particularly to methods and devices that provide electrical stimulation to the neural structures in the pelvis.

BACKGROUND OF THE INVENTION

Dysmenorrhea is the medical term for pelvic pain associated with menstruation. There are two types of dysmenorrhea. Primary dysmenorrhea refers to pain that occurs during menstruation that is not associated with an identified disorder of a woman's reproductive organs. Secondary dysmenorrhea is the medical term for pain that occurs during menstruation that is associated with a disorder in a woman's reproductive organs. The principal causes of secondary dysmenorrhea are endometriosis, adenomyosis, and uterine fibroids. Pelvic pain that is provoked or exacerbated by sexual contact or sexual intercourse is called dyspareunia.

In addition, many women suffer from chronic pelvic pain. Causes of chronic pelvic pain in women include, for instance, pelvic adhesions (scarring following surgery or pelvic infection), interstitial cystitis/bladder pain syndrome, neuropathic pain, myofascial or musculoskeletal pain and post-surgical pain. Some women experience idiopathic pelvic pain, which is pelvic pain resulting from unknown and/or undiagnosed causes. When chronic pelvic pain caused by dysmenorrhea, dyspareunia or disorders that cause chronic pelvic pain is severe, many women have significant interruptions to their daily lives, including interference with their ability to work, study, sleep, exercise, relax, travel, engage in sexual intimacy and/or sexual intercourse, and care for themselves and their loved ones. Some women experience long-term problems with their social, sexual, and psychological well-being due to the pain. Some women may also suffer from short-lived episodes of acute pelvic pain following pelvic surgery, pelvic injury or childbirth. For some women, the pain can lead to recurring bouts of depression, anxiety, emotional distress and low self-esteem.

Medicinal treatment therapies for pelvic pain typically involve hormonal therapy, non-addictive and addictive pain relievers, antidepressants, and drugs designed to treat peripheral neuropathy. However, these therapies often can cause drowsiness, dizziness, or a reduction in cognitive function leading to an inability to concentrate, work, drive or use machinery, to name but a few examples. Medicinal treatment therapies also tend to work very slowly, taking hours, days or weeks to deliver the desired pain relief. Non-medicinal therapies may include applying heating pads, hot water bottles or cold compresses to the lower abdomen or lower back. These non-medicinal therapies are typically inconvenient and cumbersome, if not completely immobilizing.

Surgical interventions to relieve pelvic pain may include laparoscopic procedures to diagnose and potentially treat intrapelvic pathology, as well as more invasive treatments, such as removal of the uterus (hysterectomy), removal of the ovaries (oophorectomies), and/or removal of the fallopian tubes (salpingectomies). However, these surgical procedures have related risks of surgical and post-surgical complications.

Transcutaneous electrical nerve stimulation ("TENS") devices, which provide electrical stimulation to the lower abdomen or back via electrodes attached to the skin, have been used to treat dysmenorrhea and pelvic pain. However, the ability of TENS devices to successfully deliver timely and effective relief from pelvic pain on a consistent and reliable basis has been extremely limited because the intrapelvic neural pathways that need to be stimulated to get effective pelvic pain relief are far removed from the areas of the body where the TENS electrodes are attached to the skin.

Accordingly, there is considerable need for devices and methods that provide convenient, faster, more direct and more effective stimulation of the neural pathways associated with pelvic pain, and reduce or avoid some or all of the above-listed disadvantages and side-effects associated with medicinal, non-medicinal and surgical therapies.

BRIEF SUMMARY OF EXEMPLARY EMBODIMENTS OF THE INVENTION

The pain associated with dysmenorrhea, dyspareunia, chronic pelvic pain, and episodes of acute pelvic pain typically originates in the uterus and other organs in the pelvis. The sensation of pelvic pain is transmitted to the central nervous system through sympathetic, parasympathetic, and afferent sensory nerve fibers that traverse neural structures in the pelvis, including the superior hypogastric plexus, the hypogastric nerves and the inferior hypogastric plexus (hereinafter the "pelvic nerves"); the nerves that traverse the cardinal ligaments and the uterosacral ligaments that attach to the lower uterus and upper cervix (hereinafter the "paracervical nerves"); and the pelvic splanchnic nerves and the sacral nerves S2, S3 and S4 (hereinafter the "sacral nerves"). Pain sensations that originate in organs or tissues that are not reproductive organs, such as the bladder, urethra, rectum, is transmitted to the central nervous system via other neural structures and plexuses in the pelvis, such as the vesicular plexus in the rectal plexus. Pain sensations that originate in the external genitalia are transmitted through the sacral nerves by way of the pudendal nerves. Hereinafter, the "pelvic nerves" the "paracervical nerves", the "sacral nerves" and other neural structures and plexuses in the pelvis may be referred to collectively as the "intrapelvic nerves."

Embodiments of the present invention, referred to collectively as intravaginal electrical stimulation devices (or "IVES devices"), overcome the aforementioned problems and disadvantages associated with existing systems and methods of reducing pelvic pain in women by providing targeted, well-controlled, and personalized electrical stimulation (in the form of low-voltage electrical current) to the intrapelvic nerves to reduce or eliminate the sensation of pelvic pain. The electrical stimulation is produced by an electrical stimulation generator (ESG) that may be located within an intravaginal capsule (IVC) that is worn internally, or the ESG may be located in an external electrical stimulation generator (EESG) that is worn externally. Electrical stimulation produced by the ESG is delivered to the tissues in and around the pelvis by one or more pairs of electrodes. Embodiments of the present invention include paracervical electrodes that are positioned inside the vagina of the patient so that they come into direct contact with the vaginal epithelium in the proximal portion of the patient's vagina. Some embodiments, but not all embodiments, also include cutaneous electrodes, which are attached to the surface of the patient's skin.

The following table summarizes configurations of four exemplary embodiments of the present invention.

| Embodiment Number | ESG Location | 1st Electrode Location | 2nd Electrode Location | Representative FIG(S). |
|---|---|---|---|---|
| 1 | Intravaginal IVC | Intravaginal Paracervical Electrode | Intravaginal Paracervical Electrode | 14 |
| 2 | External EESG | Intravaginal Paracervical Electrode | Intravaginal Paracervical Electrode | 33A |
| 3 | External EESG | Intravaginal Paracervical Electrode | External Cutaneous Electrode | 33B |
| 4 | Intravaginal IVC | Intravaginal Paracervical Electrode | External Cutaneous Electrode | 33C |

In a first embodiment of the present invention (as illustrated in FIG. 14), the ESG is located in an intravaginal IVC that is electrically connected to a pair of intravaginal paracervical electrodes. When the ESG is activated, an electrical field is created between the pair of intravaginal paracervical electrodes. The electrical field causes electrical neuromodulation of the intrapelvic nerves, resulting in a reduction or elimination of pelvic pain.

In a second embodiment of the present invention (as illustrated in FIG. 33A), the ESG is located in an externally worn EESG that is electrically connected to a pair of intravaginal paracervical electrodes. When the ESG in the EESG is activated, an electrical field is created between the paracervical electrodes. The electrical field causes electrical neuromodulation of the intrapelvic nerves, resulting in a reduction or elimination of pelvic pain.

In a third embodiment of the present invention (as illustrated in FIG. 33B), the ESG is located in an externally worn EESG that is electrically connected to an intravaginal paracervical electrode and an external cutaneous electrode attached to the surface of the patient's skin. When the ESG is activated, an electrical field is created between the paracervical electrode in the patient's vagina and the cutaneous electrode attached to the patient's skin. The electrical field causes electrical neuromodulation of the intrapelvic nerves, resulting in a reduction or elimination of pelvic pain.

In a fourth embodiment of the present invention (as illustrated in FIG. 33C), the ESG is located in an intravaginal IVC that is electrically connected to an intravaginal paracervical electrode and an external cutaneous electrode attached to the surface of the patient's skin. When the ESG in the intravaginal IVC is activated, an electrical field is created between the paracervical electrode and the cutaneous electrode. The electrical field causes electrical neuromodulation of the intrapelvic nerves, resulting in a reduction or elimination of pelvic pain.

An external controller described in detail below may be utilized in each of the embodiments noted above to send and receive information and control signals to and from the IVC or the EESG to monitor and control the electrical stimulation delivered to the patient during a treatment session.

IVES Device Exemplary Embodiment No. 1

In a first exemplary embodiment of the present invention, the IVES device comprises a set of intravaginal components and an external controller. The intravaginal components include a frame, a sling attached to and suspended from the frame, an intravaginal capsule ("IVC") and an intravaginal capsule pouch ("IVC pouch") molded into the sling and configured to receive and hold the distal end and middle portion of the IVC, a socket in the proximal end of the IVC, an electrode plug configured to be inserted into the socket, a pair of paracervical electrode connecting wires and a pair of paracervical electrodes embedded in the surface material covering the proximal portion of the frame (see FIG. 14).

The socket in the proximal end of the IVC includes a pair of male electrical contacts in its base. These male electrical contacts extend from a pair of electrical contacts on an ESG (described in more detail below) to make electrical contact with a pair of female electrical contacts, respectively, located in an electrode plug that plugs into the socket. The female electrical contacts in the electrode plug are electrically connected to a pair of paracervical electrode connecting wires that connect to a pair of paracervical electrodes embedded in the surface material of the proximal portion of the frame. Thus, electrical current created by the ESG can be transmitted to the paracervical electrodes through electrical connections present on the ESG, in the socket, in the electrode plug and the paracervical electrode connecting wires.

During use, the frame of the IVES device is inserted into the vagina of the user so that the paracervical electrodes are in direct contact with the paracervical vaginal epithelium in the lateral vaginal fornices of the vagina. The IVC contains electronic components, including a microprocessor and an ESG, that together are configured to generate an electrical potential (voltage) that causes low-voltage electrical current to flow through an electrical circuit that includes the pair of paracervical electrodes embedded in the surface material of the proximal portion of the frame. During operation of the ESG, an electrical field is created between the pair of paracervical electrodes. Because the paracervical electrodes are in the direct contact with the paracervical vaginal epithelium, the electrical field created between the paracervical electrodes passes through the vaginal epithelium and the intrapelvic tissues to cause electrical neuromodulation of intrapelvic nerves. This electrical neuromodulation tends to reduce or eliminate pelvic pain.

The external controller preferably comprises a handheld data processing and communication device, such as a tablet computer, a smart phone or remote control device. The external controller may also comprise a personal computer, such as a desktop or laptop computer. The external controller may be operated by the female patient to activate, deactivate and control the electrical profile (e.g., frequency, amplitude and duration) of the electrical stimulation delivered to the user's body by the ESG and the paracervical electrodes. To enable these neuromodulation control functions, the external controller includes a microprocessor, a memory, a computer program (hereinafter referred to as the "IVES device remote control application" or the "IVES app") stored in the memory, and a radio frequency transceiver. The IVES app contains program instructions executable by the microprocessor in the external controller. Operating under the control of the IVES app and the microprocessor, the radio frequency transceiver is configured to establish a wireless data communication channel with a second radio frequency transceiver located inside the IVC of the intravaginal component of the IVES device. The IVES app also comprises program instructions that, when executed by the microprocessor on the external controller, will cause the microprocessor to use the radio frequency transceiver in the external controller to send instructions to, and receive status updates from, the microprocessor inside the IVC via the wireless data communications channel established between the two radio frequency transceivers.

When the ESG is operating to generate the necessary voltage and the electrical field exists between the pair of paracervical electrodes, low voltage electric current flows through a circuit (hereinafter referred to as an electrical stimulation circuit, or "ESC"), the ESC comprising the ESG, a pair of electrical contacts on the ESG, a pair of male electrical contacts in the socket connected to the electrical contacts on the ESG, a corresponding pair of female electrical contacts in the electrode plug, a pair of paracervical electrode connecting wires, a pair of paracervical electrodes, and the electrical field created between the pair of paracervical electrodes. In other words, when the ESG generates the electric potential (i.e., voltage) at one end of the ESC, low-voltage current begins to flow from the ESG into and through the socket, and then into and through the electrode plug, and then into and through one of the paracervical electrode connecting wires, then into a paracervical electrode, then through the tissues of the pelvis (as an electrical field, sometimes referred to as an electromagnetic field), then into and through the other paracervical electrode, then into and through the other paracervical electrode connecting wire, then back through the electrode plug, then back through the socket and finally back into the electrical contacts on the ESG, which completes the circuit. The electrical field created between the paracervical electrodes causes the electrical neuromodulation of the intrapelvic nerves, which tends to reduce or eliminate pelvic pain. Depending on the instructions sent to the ESG from the microprocessor in the IVC, the low-voltage current may be made to flow in only one direction (direct current), or the low-voltage current may be made to alternate between flowing in one direction for a short period of time before being reversed to flow in the opposite direction for a short period of time (alternating current) as it moves through the ESC.

Embodiments of the IVES device may be constructed to allow the ESG to create multiple ESCs at the same time with each ESC being capable of producing an electrical field with unique characteristics when the ESG is activated. In these IVES devices, the IVES app stored in the memory of the IVES device may include program instructions that, when executed by the microprocessor, will cause the ESG to activate the multiple ESCs simultaneously, sequentially or in an alternating pattern, with unique and possibly with differing characteristics, to neuromodulate different sets of intrapelvic nerves, to decrease or eliminate pelvic pain. The use of multiple ESCs will be described in more detail below.

Each ESC in the IVES device includes a pair of electrode units (referred to as "EUs"). An EU comprises an electrical contact that resides inside of the electrode plug, an electrode connecting wire (either a paracervical electrode connecting wire or a cutaneous electrode connecting wire) and an electrode (either a paracervical electrode or a cutaneous electrode). Thus, the components of one EU forms a portion of "one side" of an ESC, and the components of a second EU forms a portion of the "other side" of the ESC. When the electrode plug is inserted into the socket in the IVC and the ESG is activated, low-voltage current flows through a pair of EUs and an electrical field is created between the two electrodes in the pair of EUs, respectively, and a complete ESC is created. In some embodiments of the present invention, the EU could terminate at a cutaneous electrode (instead of a paracervical electrode) that may be affixed to the patient's skin. By way of example, a cutaneous electrode may be attached to the patient's back in the mid-line at the level of the L5-S1 vertebral junction. However, one or more cutaneous electrodes could be placed in other locations on the skin of the pelvis or abdomen. As previously stated, in some embodiments, the ESG could be located in an externally worn external electrical stimulation generator ("EESG") instead of being located in an IVC. In this case, the EESG, contains essentially the same components as the IVC, including an ESG, and a socket to receive the electrode plug.

Suitably, the electrode plug is configured to receive and hold at least a pair of electrical contacts from the electrode connecting wires in a pair of EUs, and the socket in the IVC or EESG is configured to receive and hold (preferably in water-tight fashion) the electrode plug. Inserting the electrode plug into the socket of the IVC or EESG permits the flow of electrical current from the ESG in the IVC or EESG through the socket, and into the plug, the electrode connecting wires, and the paracervical electrodes or cutaneous electrodes making up the two EUs in an ESC. Preferably, the ESG in the IVC or EESG, the socket in the IVC or EESG and the electrode plug are all "multi-channeled," meaning the ESG can be activated to create, maintain and control multiple ESCs and multiple electrical fields possibly with differing characteristics simultaneously, sequentially and/or in alternating fashion to electrically neuromodulate the intrapelvic nerves.

A user interface module in the IVES app is configured to interact with the display screen on the external controller to permit the user to activate, adjust and tune the electrical stimulation generated and delivered to the paracervical electrodes by the ESG. Thus, the program instructions in the user interface module of the IVES app are suitably configured to allow the patient to manipulate controls (such as digital representations of buttons, icons and sliders) displayed on the display screen of the external controller in order to select, personalize, optimize, adjust, save, recall, activate and/or deactivate the settings and/or profile of the electrical stimulation delivered to the intrapelvic nerves by the ESG in the IVC. In addition, the radio frequency transceiver and the microprocessor inside the external controller can request data and status information from the microprocessor and/or the memory of the IVC, and receive the data and status information over the wireless communication channel. The status information and other data may be displayed on the display screen associated with the external controller via the user interface.

Preferably, the user interface may be configured to enable a patient to send information and data to other devices, and/or to organizations or people, such as, for example, the user's personal physician, or an IVES practitioner who may be responsible for monitoring the patient's responses to treatment using various ESPs delivered by her IVES device. The communication of information and data to personal physicians and IVES practitioners not only facilitates developing customized individual therapies for an individual patient, it also permits and supports aggregating the treatment and outcome data for large groups of patients with different pain-causing conditions.

Preferably, the IVES app stored in the memory of the external controller also includes program instructions that permit the external controller to periodically query a remote computer system or server to determine (1) whether any program updates associated with the IVES app running on the external controller are available, and/or (2) whether operating system updates, local program updates or firmware updates associated with the local control program stored in the memory of the IVC 102 are available. If such an update is available, the IVES app may be configured to automatically download and install the update on the external controller, on the IVC, or both. By downloading such updates as they become available, the control application program running on the external controller, as well as the operating system, application program and firmware running on the IVC will automatically remain substantially up-to-date with the latest bug fixes and/or operating system improvements. In some embodiments, the IVES app may be configured to prompt the user for permission or confirmation before downloading and/or installing program, operating system or firmware updates.

Within an IVC there is a circuit board containing an ESG that provides the electrical potential (voltage) to start the flow of the low-voltage current in one or more ESCs, which in turn provides electrical stimulation to the intrapelvic nerves. Each ESC includes a pair of electrical contacts on the ESG, which are the starting point and ending point of the ESC. The electrical current resulting from the application of voltage to the ESC by the ESG passes from an electrical contact on the ESG, to a male electrical contact in the base of the socket, to a female electrical contact in the plug, to a paracervical electrode connecting wire, to a paracervical electrode, through an electrical field, to another paracervical electrode, to another paracervical electrode connecting wire, to another female electrical contact in the plug, to a male electrical contact in the socket and to the corresponding electrical contact on the ESG.

When the ESG is operating to generate the necessary voltage, an electrical field is created between the pair of paracervical electrodes embedded in the surface covering of the proximal portion of the frame. In other words, when the ESG is operating, the ESG generates an electric potential (i.e., voltage) at one end of an ESC where low-voltage current begins to flow from an electrical contact on the ESG into and through the socket, then into and through the electrode plug, then into and through one of the paracervical electrode connecting wires, then into a paracervical electrode embedded in the surface covering of the proximal portion of the frame, then through the tissues of the pelvis (as an electrical field), then into and through the other paracervical electrode embedded in the surface covering of the proximal portion of the frame, then into and through the other paracervical electrode connecting wire, then back through the electrode plug, then back through the socket and finally back to the electrical contact on the ESG, which completes the circuit. The targeted, well-controlled, and personalized electrical stimulation created by this ESC causes electrical neuromodulation of the intrapelvic nerves, resulting in an elimination or reduction of pelvic pain.

IVES Device Exemplary Embodiment No. 2

In a second exemplary embodiment of the present invention, the IVES device is comprised a set of external components including an external controller and an EESG with a socket to receive and connect to an electrode plug and a set of intravaginal components identical to those described in the first embodiment, except the ESG of this IVES device is located in the EESG instead of in the IVC (see FIG. 33A).

When the ESG is operating to generate the necessary voltage, an electrical field is created between one of the pair of paracervical electrodes embedded in the surface covering of the proximal portion of the frame. In other words, when the ESG is operating, the ESG generates an electric potential (i.e., voltage) at one end of an ESC where low-voltage current begins to flow from an electrical contact on the ESG into and through the socket, then into and through the electrode plug, then into and through one of the paracervical electrode connecting wires, then into a paracervical electrode embedded in the surface covering of the proximal portion of the frame, then through the tissues of the pelvis (as an electrical field), then into and through the other paracervical electrode embedded in the surface covering of the proximal portion of the frame, then into and through the other paracervical electrode connecting wire, then back through the electrode plug, then back through the socket and finally back to the electrical contact on the ESG, which completes the circuit. The targeted, well-controlled, and personalized electrical stimulation created by this ESC causes electrical neuromodulation of the intrapelvic nerves, resulting in an elimination or reduction of pelvic pain.

IVES Device Exemplary Embodiment No. 3

In a third exemplary embodiment of the present invention, the IVES device is comprised a set of external components including an external controller, an EESG with a socket to receive and connect to an electrode plug and a cutaneous electrode and a set of intravaginal components identical to those described in the first embodiment, except the ESG of this IVES device is located in an EESG instead of an IVC.

When the ESG is operating to generate the necessary voltage, an electrical field is created between one of the paracervical electrodes embedded in the surface covering of the proximal portion of the frame, and a cutaneous electrode placed on the midline of the patient's back at the level of the L5-S1 vertebral junction. In other words, when the ESG generates the electric potential (i.e., voltage) at one end of the ESC, low-voltage current begins to flow from an electrical contact on the ESG into and through the socket, and then into and through the electrode plug, and then into and through one of the paracervical electrode connecting wires, then into a paracervical electrode embedded in the surface covering of the proximal portion of the frame, then through the tissues of the pelvis (as an electrical field), then into and through the cutaneous electrode, then into and through a cutaneous electrode connecting wire, then back through the electrode plug, then back through the socket and finally back into the ESG, which completes the circuit (see FIG. 33B).

IVES Device Exemplary Embodiment No. 4

In a fourth exemplary embodiment of the present invention, the IVES device is comprised a set of external components including an external controller and a cutaneous electrode and a set of intravaginal components identical to those described in the first embodiment of the present invention.

When the ESG is operating to generate the necessary voltage, an electrical field is created between one of the paracervical electrodes embedded in the surface covering of the proximal portion of the frame, and a cutaneous electrode placed on the midline of the patient's back at the level of the L5-S1 vertebral junction. In other words, when the ESG generates the electric potential (i.e., voltage) at one end of the ESC, low-voltage current begins to flow from an electrical contact on the the ESG into and through the socket, and then into and through the electrode plug, and then into and through one of the paracervical electrode connecting wires, then into a paracervical electrode, then through the tissues of the pelvis (as an electrical field), then into and through the cutaneous electrode, then into and through the other paracervical electrode connecting wire, then back through the electrode plug, then back through the socket and finally back into the ESG, which completes the circuit (see FIG. 33C).

BRIEF DESCRIPTION OF THE DRAWINGS

FIG. 1 shows anatomical diagrams of a woman and a man illustrating the conventional terms used to identify and describe the parts and planes of the human body, and the relationships there between.

FIGS. 11, 12, and 13A show schematic diagrams illustrating the typical placement and orientation of the IVES device within the vagina in accordance with some embodiments of the present invention.

FIG. 13B shows an enlarged view of the upper vagina and uterine cervix with the proximal end of the IVES device in-situ to illustrate the proper positioning of the paracervical electrodes in the lateral vaginal fornices.

FIG. 35 shows side-view of the electrical field created by an ESC comprised of a paracervical electrode in a lateral vaginal fornix and a cutaneous electrode applied to the midline of the lower back at the level of the L5-S1 vertebral junction.

DETAILED DISCUSSION OF EXEMPLARY EMBODIMENTS

Anatomical Terminology

For purposes of the discussions that follow, "proximal" means nearer to the central portion of the body and distal means farther from the central portion of the body. The proximal portion of the vagina is the innermost and uppermost portion of the vagina near the uterine cervix. The distal portion of the vagina is the lowermost portion of the vagina near the vaginal orifice. Anterior means toward the front of the body and posterior means toward the back of the body. Medial means at, near or approaching the vertical midline of the body, when viewed from the front or rear, and lateral means at some distance away from the vertical midline of the body, as in at, near or approaching the sides of the body, when viewed from the front or rear.

Figure 1:
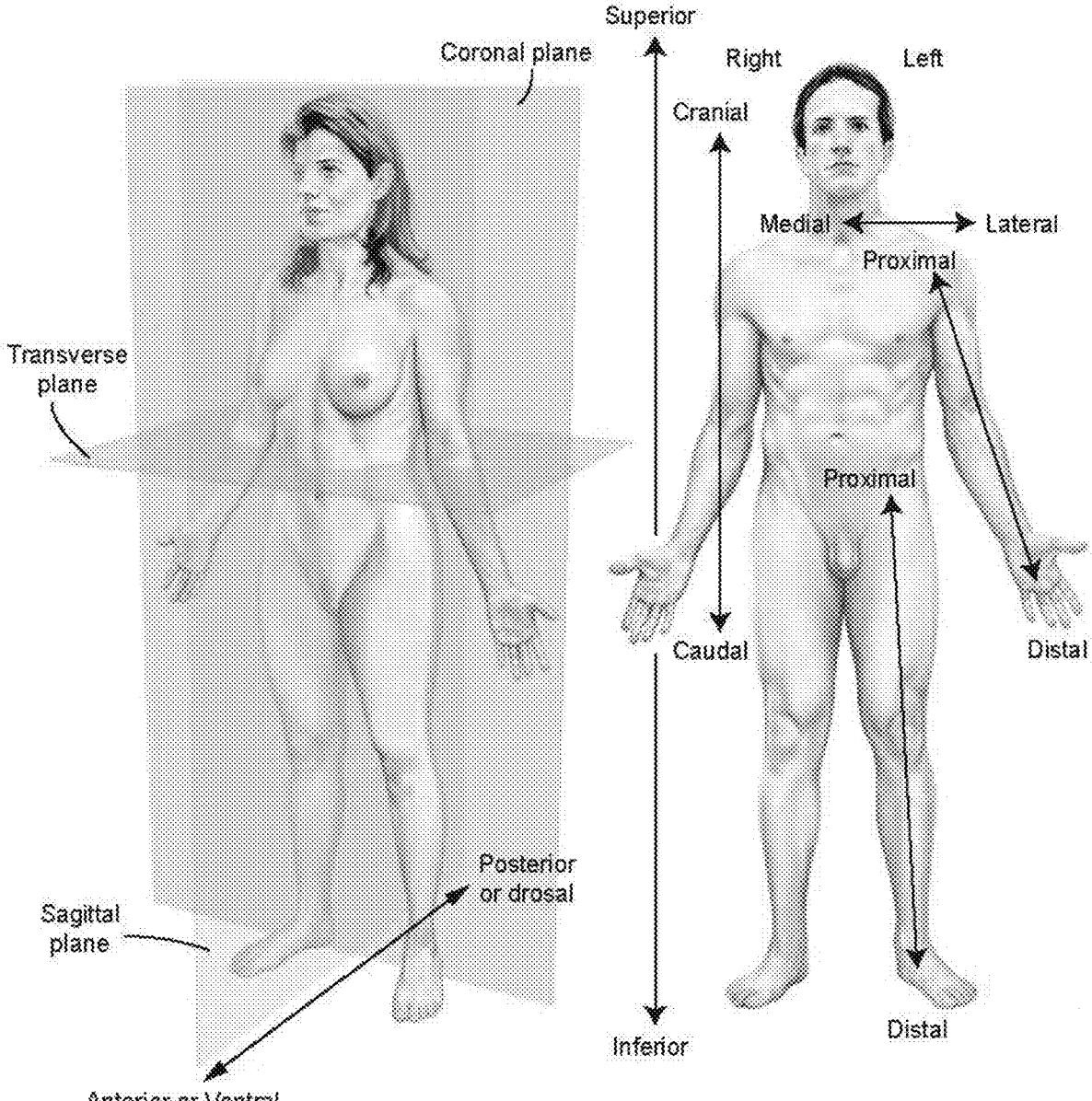

FIG. 1 shows anatomical diagrams of a woman and a man illustrating the conventional terms used to identify and describe the relationship of body parts to one another and planes of the human body. An anatomical plane (or anatomical section) refers to a view of anatomical structures in reference to a certain plane. For example, the median plane (or midline section) is a vertical plane that passes through the body longitudinally, front to back, dividing the body into equal right and left halves. A sagittal plane is any vertical plane passing through the body that is parallel to the median plane. Sagittal planes divide the body into right and left parts. Therefore, the midline plane is a sagittal plane, but a sagittal plane need not be the midline plane. The coronal planes, also called the frontal planes, are vertical planes passing through the body, from one side to the opposite side, dividing the body into an anterior (front) portion and a posterior (back) portion. These vertical coronal planes are at right angles (90°) to the median and sagittal planes. Transverse planes are horizontal planes passing through the body, dividing it into superior (upper) and inferior (lower) parts. These horizontal transverse planes are at right angles (90°) to the median, sagittal and coronal planes.

Pelvic Anatomy

Figure 2:
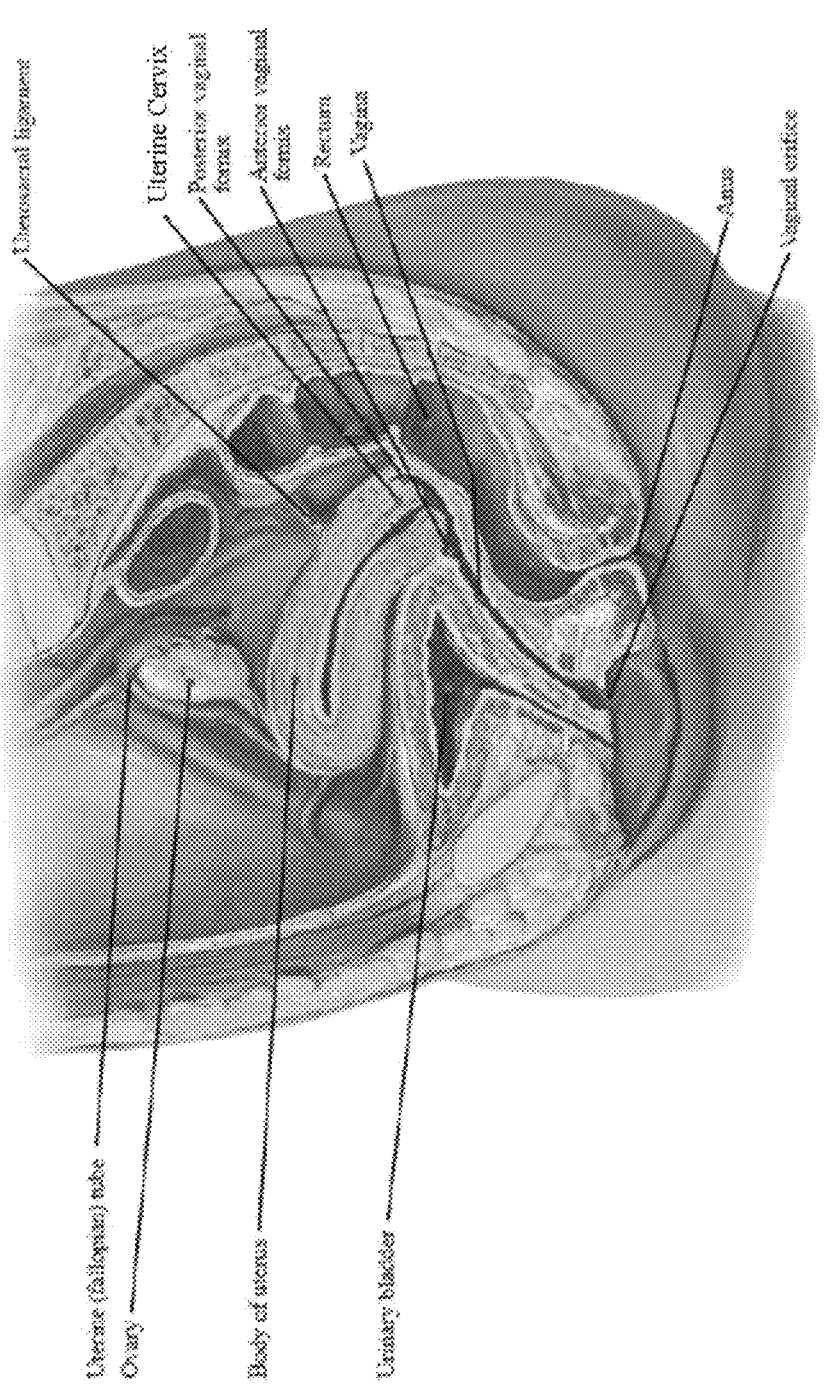
FIG. 2 shows an illustration of a midline sectional view of a human female pelvis and the location of female anatomical structures within the pelvis.

FIG. 2 shows an illustration of a midline sectional view of a human female pelvis. The pelvis is the lower part of the abdomen that is below the rim of the pelvic bones.

Figures 3A, 3B:
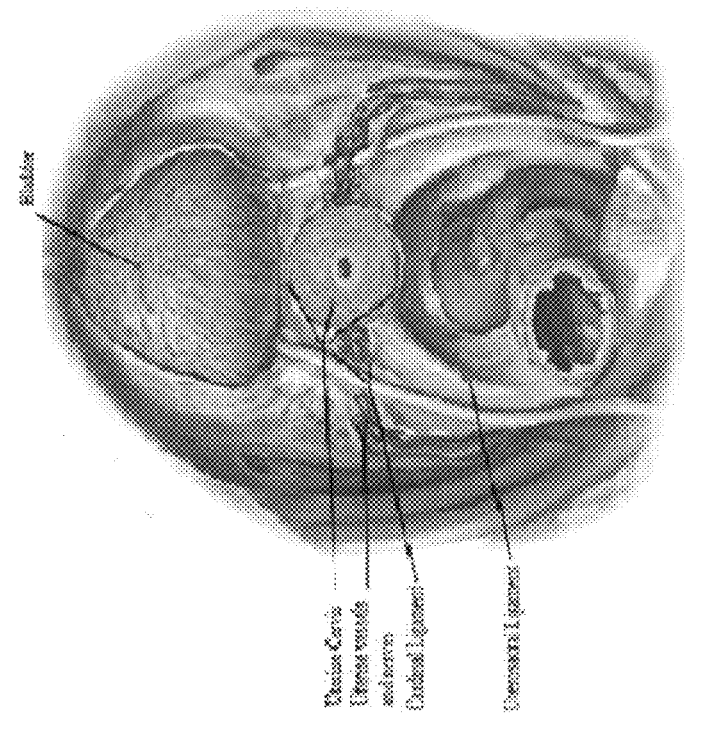
FIG. 3A shows an illustration of a superior view of the pelvic viscera (as visualized from within the abdomen)
FIG. 3B shows an illustration of a superior view of the pelvic viscera and the pelvic floor with the peritoneum and uterus removed (as visualized from within the abdomen).
Figure 4:
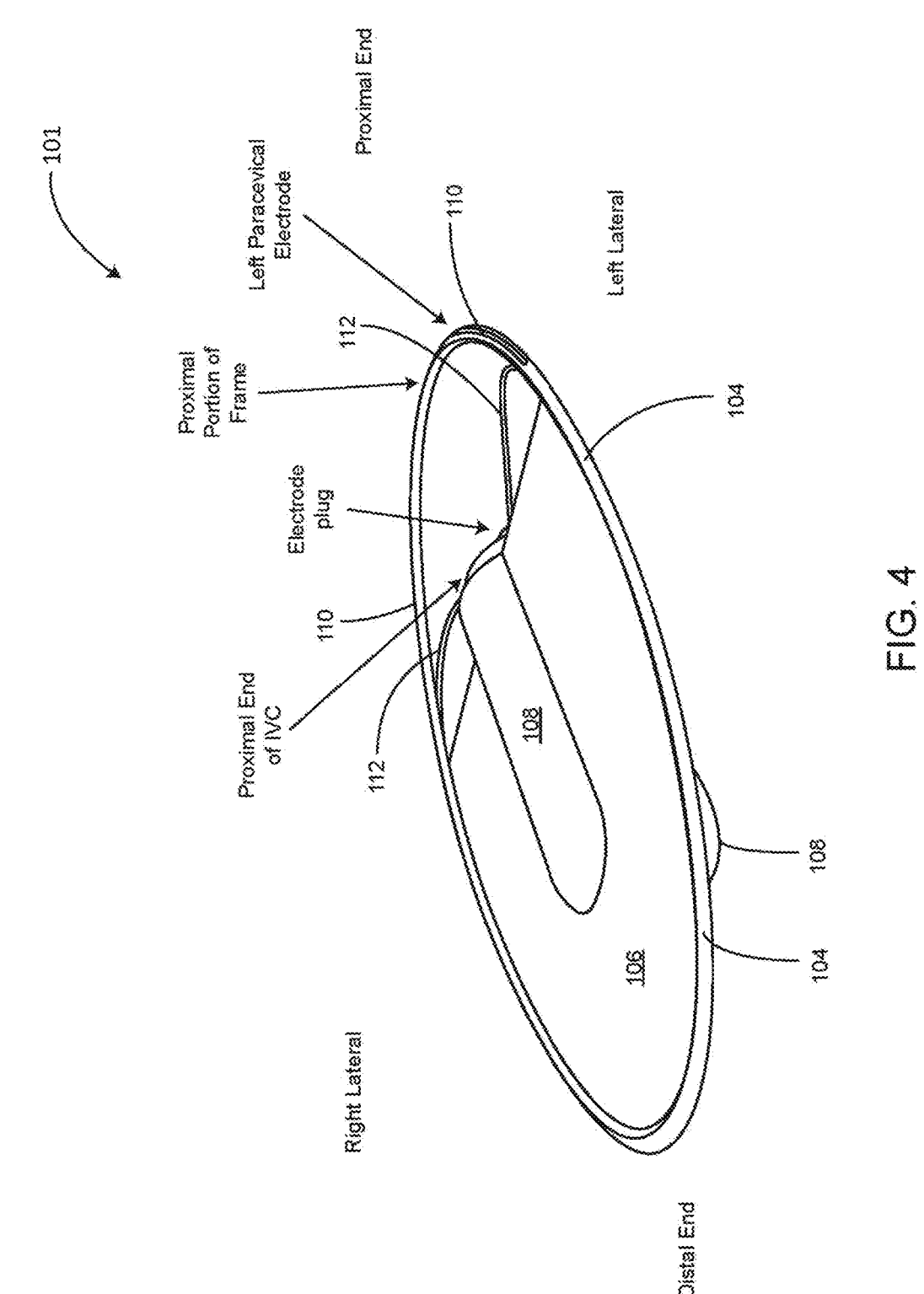
FIG. 4 shows a perspective view of an exemplary IVES device constructed in accordance with one embodiment of the present invention as seen from a left, distal and anterior-lateral point of view.

FIG. 3A shows an illustration of a superior view of the pelvic viscera (as visualized from within the abdomen), and FIG. 3B shows an illustration of a superior view of the pelvic floor with the peritoneum and uterus removed (as visualized from within the abdomen). As shown in FIGS. 2, 3A and 3B, the female pelvic viscera (or organs) that lie within the pelvis are the uterine fundus (the upper portion of the uterus), fallopian tubes, ovaries, bladder and rectum. These organs are located above, and supported by, the endopelvic fascia and ligaments that create the pelvic floor. The female viscera that lie below the pelvic floor include the uterine cervix, vagina, urethra, and the lowermost part of the rectum. FIG. 4 shows a perspective view of an exemplary IVES device 101 constructed in accordance with one embodiment of the present invention, as it would appear if observed from a left, distal and anterior-lateral point of view.

Figure 5:
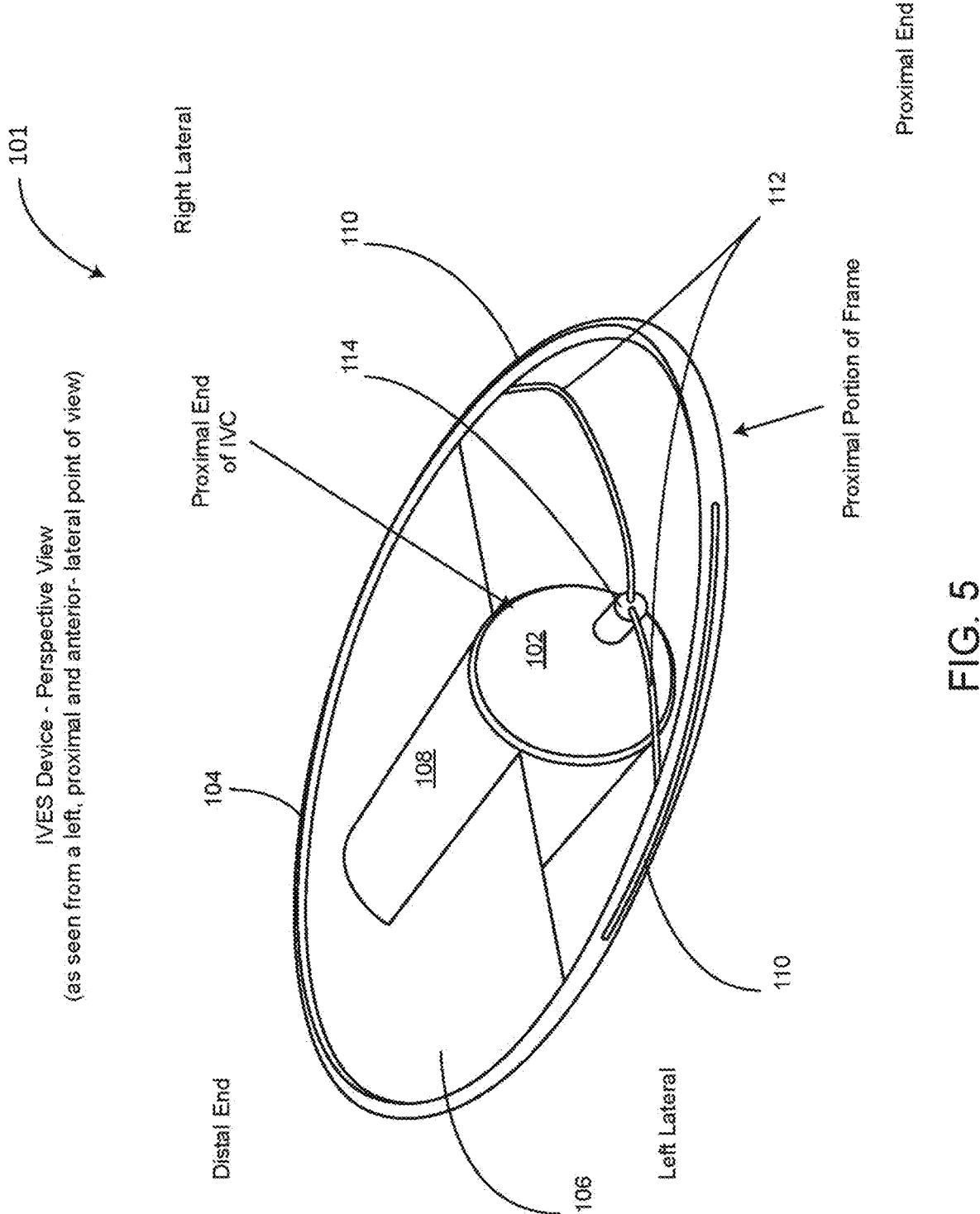
FIG. 5 shows a perspective view of the IVES device constructed in accordance with one embodiment as seen from a left, proximal and anterior-lateral point of view.
Figure 6:
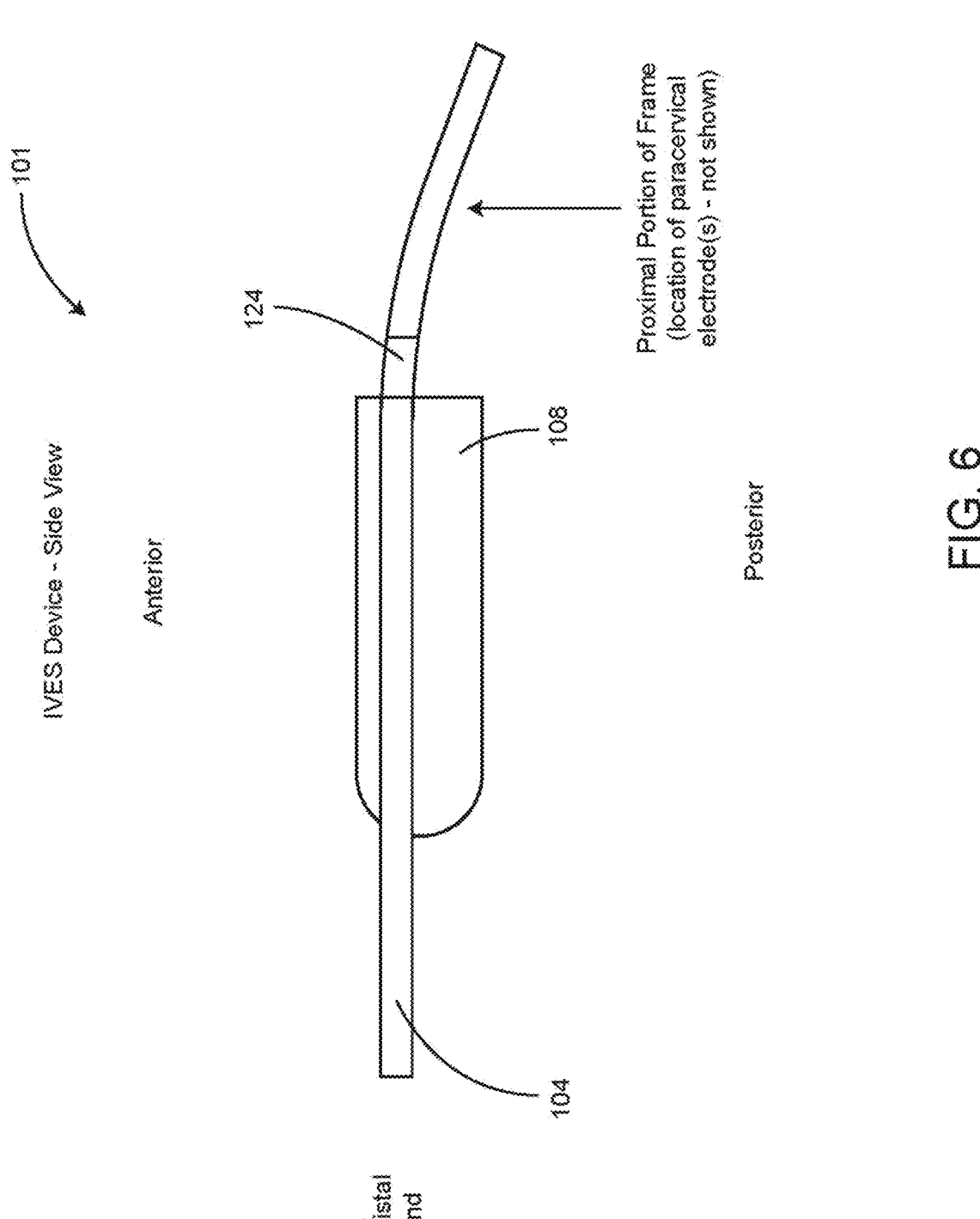
FIGS. 6, 7, 8, and 9 show a side view, a top view, a transverse cross-section view (viewed from the distal end of the IVES device), and a longitudinal cross-section view of one embodiment of the present invention, respectively.
Figure 7:
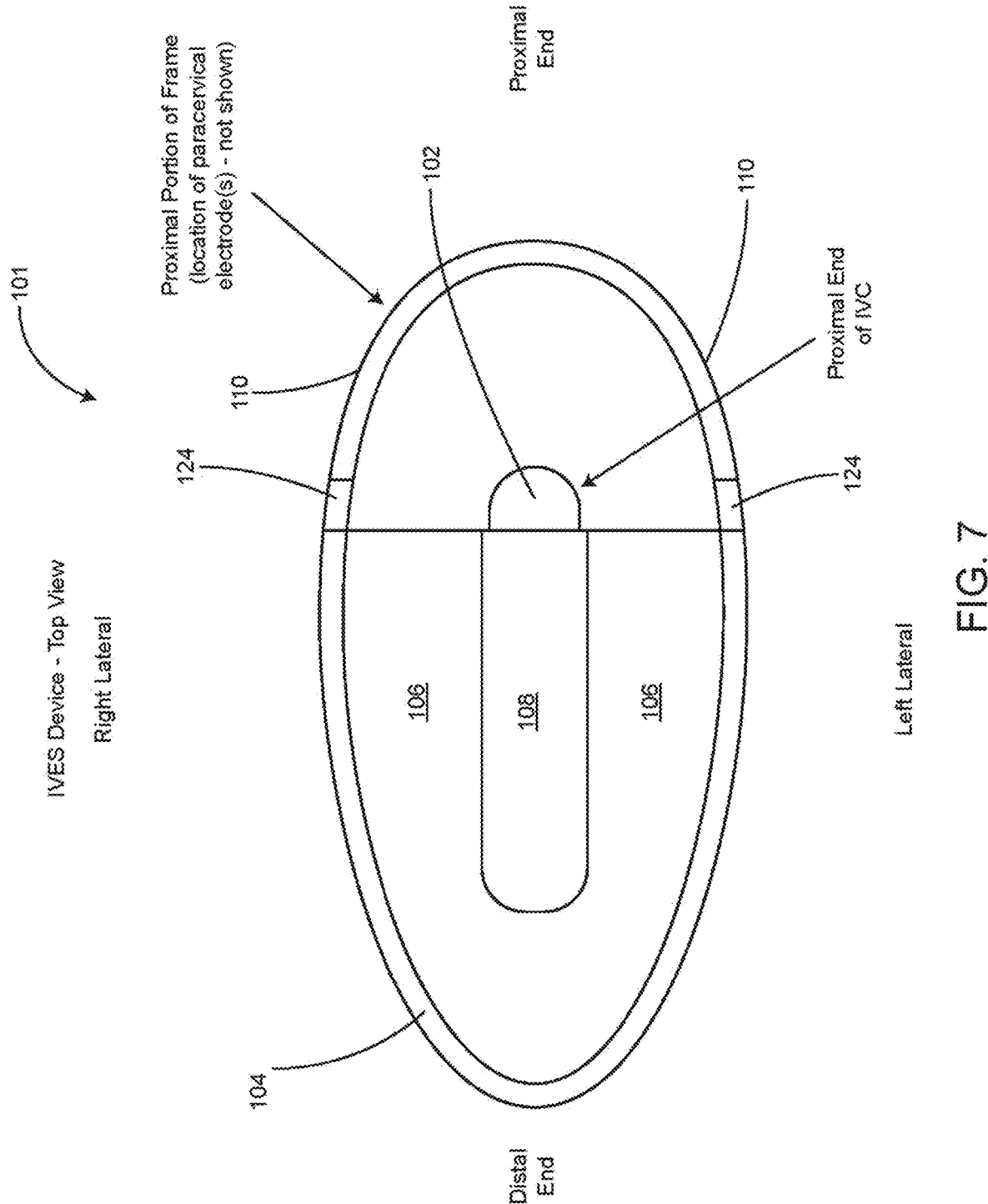
Figure 8:
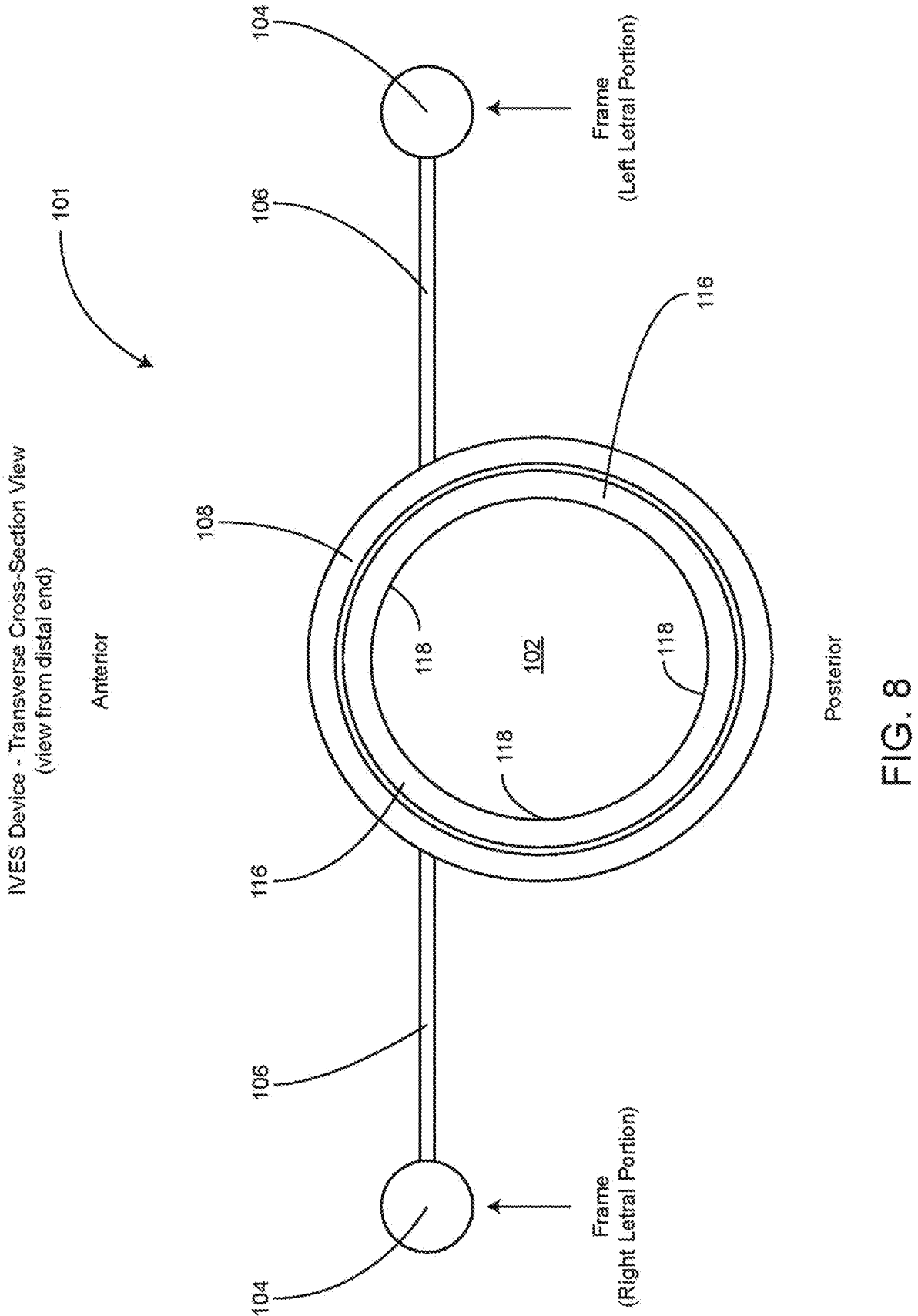
Figure 9:
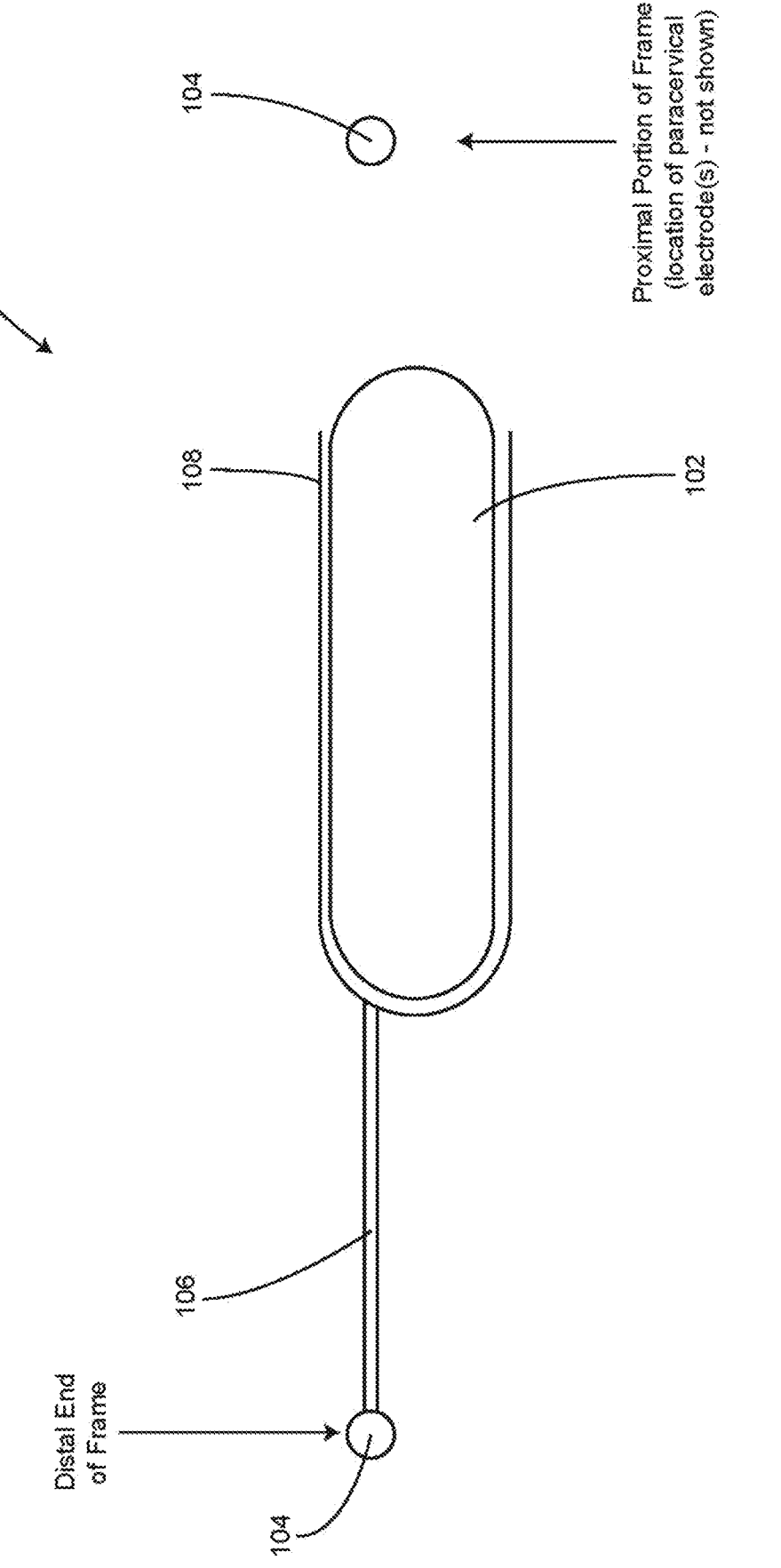

FIG. 5 shows a perspective view of the IVES device 101 as it would appear if observed from a left, proximal and anterior-lateral point of view. FIGS. 6, 7, 8, and 9 show a side view, a top view, a transverse cross-sectional view (viewed from the distal end of the IVES, and a longitudinal cross-section view, respectively. As shown in FIGS. 4, 5, 6, 7, 8 and 9, an IVES device generally comprises an intravaginal capsule (IVC) 102, a socket in the IVC 122, a frame 104, a sling 106, an IVC pouch 108 a pair of paracervical electrode connecting wires 112, and a pair of paracervical electrodes 110.

The Paracervical Electrode

The paracervical electrode 110 comprises one or more wires, capable of carrying or conducting electrical current, which are embedded in the covering of the proximal portion of the frame 104. In one embodiment, the surface area of a paracervical electrode 110 may be increased by attaching a thin "wafer" of electrode material (that might be round, square or rectangular, for example) to the paracervical electrode 110 embedded in the covering of the proximal portion of the frame 104. The wire and wafer comprising the paracervical electrode 110 may be uninsulated, or minimally insulated, so that the electrical stimulation generated by the electrical stimulation generator and transmitted to the paracervical electrodes 110 is delivered to the paracervical vaginal epithelium, and hence, the pelvic nerves, paracervical nerves and sacral nerves.

The Frame

The frame 104 is a structural element that is designed to reside comfortably in a woman's vagina when the set of the IVES device 101 is in use. Its core may be made of a semirigid, yet flexible material, such as a coiled spring made of metal or plastic, a rod made of metal, plastic or fiberglass, or a combination of several of these materials. In addition, the material or materials used in the frame 104 may have different configurations and properties in different areas of the frame 104 to achieve the semi-rigidity or flexibility desired for that area of the frame 104. Notably, those skilled in the art will recognize and appreciate that a variety of alternative construction materials may be suitably substituted for the aforementioned materials without departing from the scope of the present invention.

The shape of the frame 104 in its uncompressed state is substantially elliptical. However, the frame 104 forms a posteriorly directed curvilinear shape when its lateral portions are compressed toward each other. The frame 104 is configured so that it has a propensity to return to its original shape when compressive forces are released. The compressive forces are introduced, for example, when the user squeezes the lateral portions of the frame 104 toward each other with the thumb and fingers of one hand prior to its insertion into the vagina. The compressive forces are reduced after the IVES device 101 passes entirely into the vagina 146 and the patient stops compressing together the lateral portions of the frame 104.

Suitably, the proximal and distal ends of the frame 104 are typically the most flexible portions of the frame 104, allowing significant compression of the frame 104 along its longitudinal axis. Compression of the frame 104 along its longitudinal axis and the resulting posterior curvature of the frame 104 make insertion of the intravaginal components 101 into the vagina easier to accomplish. When the IVES device 101 is completely inserted into the vagina and the compression forces on the lateral portions of the frame 104 are removed, the frame 104 returns to its original configuration, at which point the distal end of the frame 104 rests upon the anterior vaginal wall behind the synthesis pubis and the proximal end of the frame 104 rests upon the vaginal epithelium in the posterior vaginal fornix (refer to FIG. 12, discussed in more detail below). In this configuration inside the vagina, the paracervical electrodes 110 embedded in the surface of the covering of the proximal portion of the frame 104, will come into contact with the vaginal epithelium in the lateral vaginal fornices. The lateral portions of the frame 104 are configured to gently press against the lateral walls of the vagina, keeping the frame 104 and the rest of the intravaginal components 101 of the IVES device 100 in the proper position within the vagina.

In another embodiments of the present invention, a "transitional" portion 124 (shown best in FIGS. 6 and 7) may be located in both of the lateral portions of the frame 104 between the point where the attachment of the sling 106 to the lateral portions of the frame 104 terminates and the distal end of paracervical electrodes 110 embedded in the covering of the proximal portion of the frame 104. The transitional portion 124 of the frame 104 may be curved slightly posteriorly and may be more flexible than the other portions of the frame 104 to facilitate the positioning of the proximal portion of the frame 104 in the posterior and lateral vaginal fornices when the IVES device 101 is introduced into the vagina. The propensity of the transitional portion 124 of the frame 104 to return to its original configuration after any pressure applied to it is released will cause the proximal portion of the frame 104 to apply gentle pressure superiorly and posteriorly to the vaginal epithelium in the posterior and lateral vaginally fornices, keeping the paracervical electrodes 110 in contact with the paracervical vaginal epithelium in the lateral fornices and properly positioned to deliver electrical stimulation to the intrapelvic nerves.

The Sling and IVC Pouch

As shown best in FIGS. 4 through 8, the sling 106 is a thin membrane of a flexible, medical grade material, such as silicone rubber, for example, which is attached to the inner aspect of the distal and lateral portions of the frame 104. The IVC pouch 108 is a cylindrically shaped pouch, bag, sack or pocket in the sling 106 that is suitably aligned longitudinally with the midline of the IVES device 101. The IVC pouch 108, which is typically made from the same medical grade material used to make the sling 106, has a closed end distally and an open end proximally. The open end of the IVC pouch 108 is aligned with the proximal edge of the sling 106. Notably, those skilled in the art will recognize and appreciate that a variety of alternative construction materials may be suitably substituted for the aforementioned silicone rubber in the sling 106, the IVC pouch 108 and the covering of the frame 104 without departing from the scope of the present invention.

The Intravaginal Capsule

Figure 14:
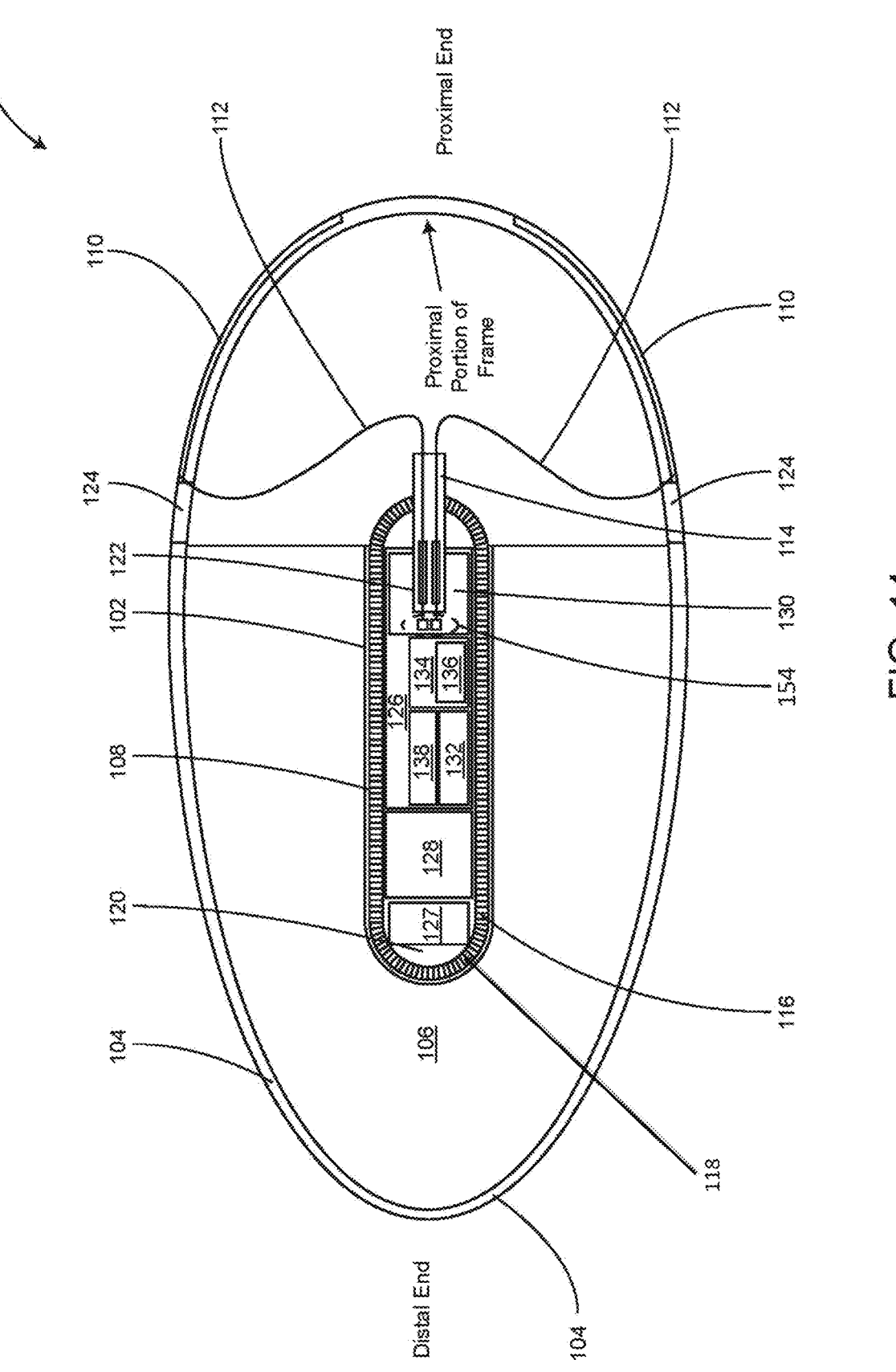
FIG. 14 shows a more detailed view of one embodiment of the IVES device.

As shown best in FIG. 14, the IVC 102 typically comprises a hard-plastic cylindrical shell 116 with rounded ends. The shell 116 has interior walls 118 that define an interior cavity 120 for housing most of the electronic parts of the IVES device 101. The electronic components inside the shell 116 of the IVC 102 may include, for example, a printed circuit board 126, a rechargeable battery 128, an inductive charging coil 127 for charging the rechargeable battery 128, an electrical stimulation generator (ESG) 130, a microprocessor 132, a memory 134, a local control program 136 in the memory 134, and a radio frequency transceiver 138. These electronic components are discussed in more detail below with references to FIG. 14.

Notably, although the IVC 102 of the exemplary embodiments described herein and shown in the accompanying figures has a longitudinal cross section that is cylindrical and a transverse cross section that is round, it will be understood that in other embodiments, the shape of the IVC 102 may be different. It should also be understood that the frame 104 may be manufactured in several different sizes and with materials that allow modifications to the manufactured shape so that they can be "custom fit" for individual users having a variety of different body sizes, body shapes and body conditions.

Figure 10A:
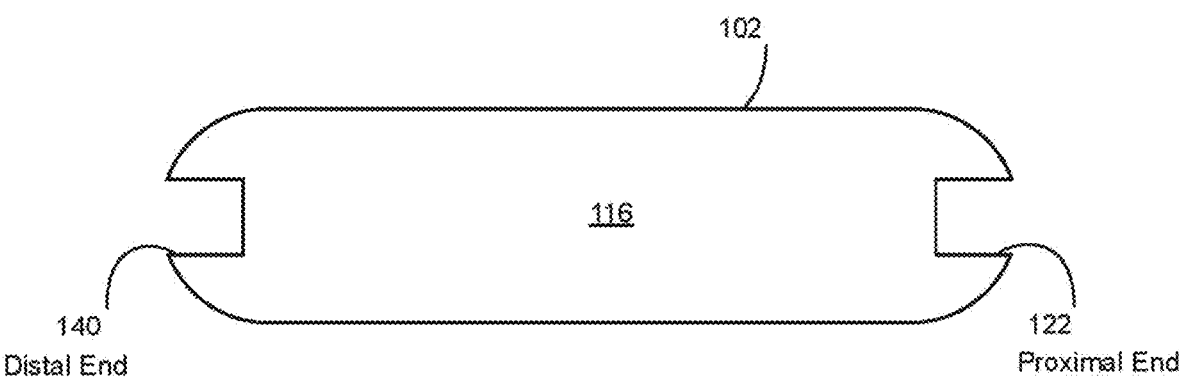
FIGS. 10A, 10B and 10C show, respectively, an orthogonal view of the IVC, a distal end on view of the IVC, and a proximal end on view of the IVC.
Figure 10B:
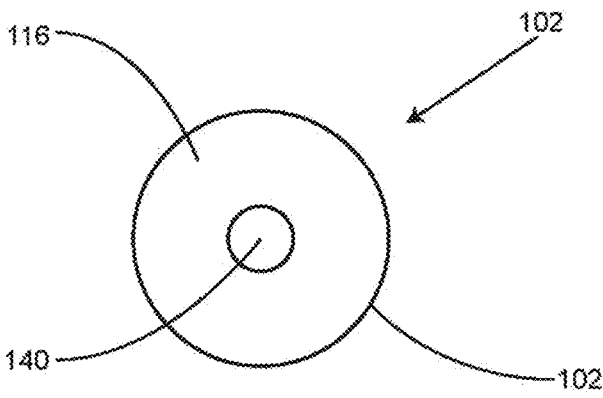
Figure 10C:
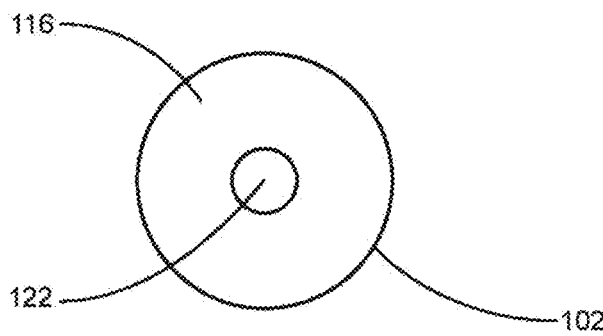

FIGS. 10A, 10B and 10C show, respectively, an orthogonal view of the IVC 102, a distal end on view of the IVC 102, and a proximal end on view of the IVC 102. The IVC 102 comprises a hard-plastic cylindrical shell 116 with rounded ends. The IVC shell 116 may (or may not) be permanently sealed to protect its contents from moisture and so that it cannot be opened by the user. As shown best in FIG. 10B, molded into the distal end of the shell 116 of the IVC 102 is an alignment pin receiving location 140 configured to receive the tip of an alignment pin (not shown) on an external wireless battery charger (also not shown in the figures). This alignment pin receiving location 140 facilitates proper alignment of the inductive charging coil 127 for the rechargeable battery 128 inside the IVC 102 and the charging coil of the external wireless battery charger. As shown best in FIG. 10C, molded into the proximal end of the shell 116 of the IVC 102 is a IVC socket 122, which is configured to receive an electrode plug 114 (described in more detail below). Optionally, heating elements may be embedded in the walls 118 of the cylindrical shell 116 of the IVC 102. Operating under the control of the external controller 103 and the IVES app 160 running on the external controller 103, these optional heating elements may be activated by the user via the external controller 103 to provide heat therapy for additional pain relief.

Figure 11:
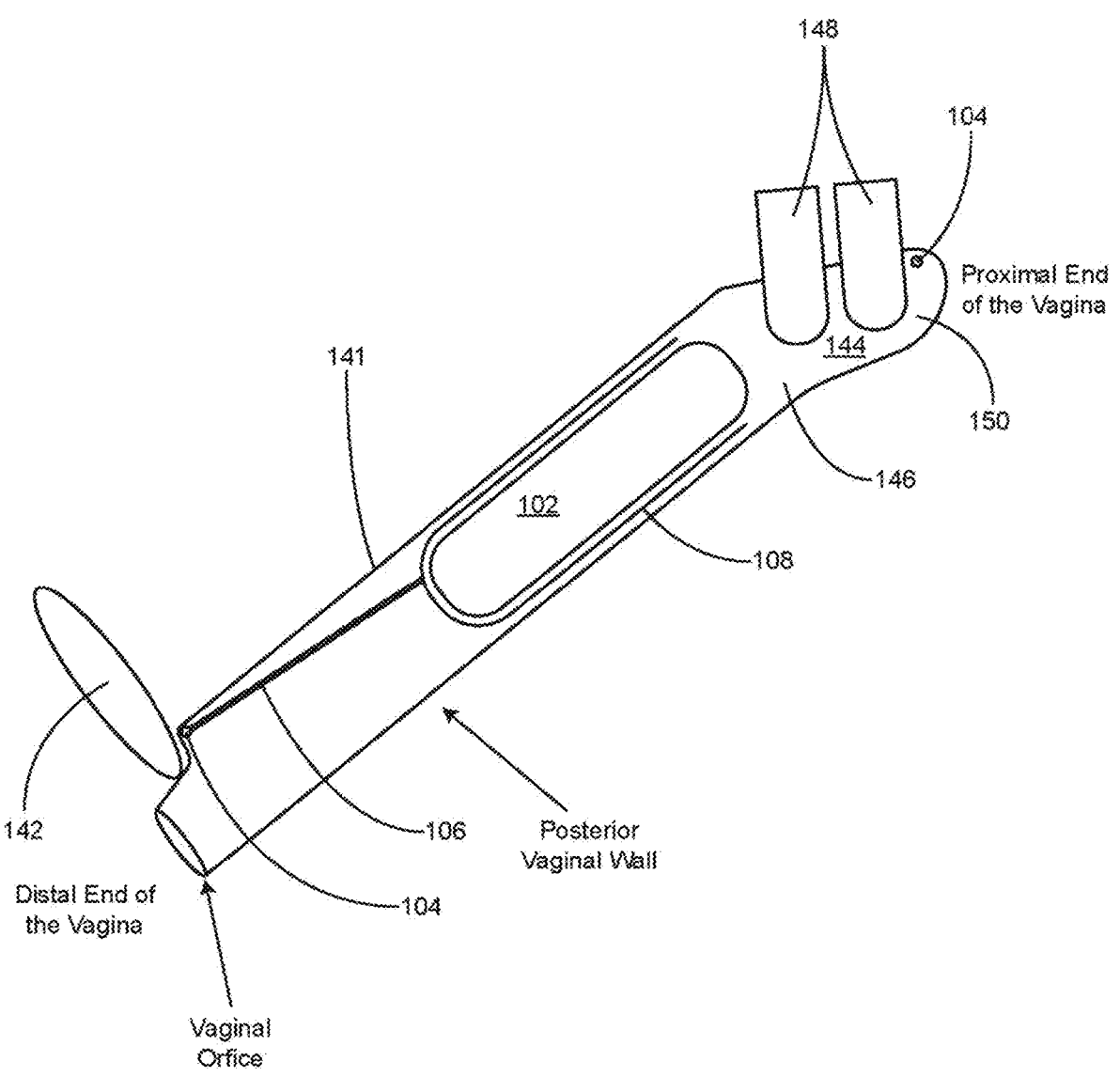
Figure 12:
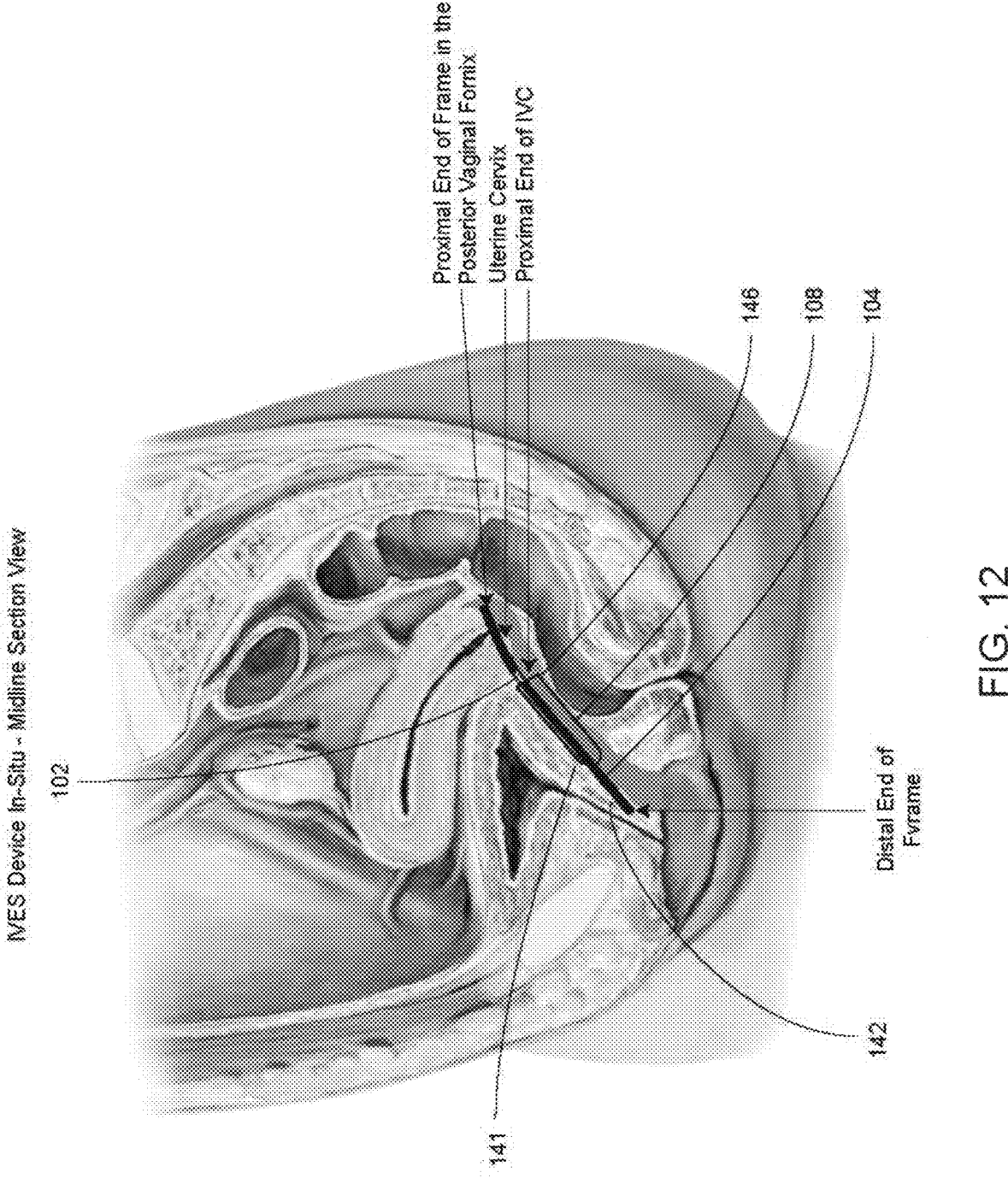

FIGS. 11, 12, and 13A show schematic diagrams illustrating the typical placement and orientation of the IVES device 101 within the vagina in accordance with some embodiments of the present invention. As shown best in FIGS. 11 and 12, the distal end of the frame 104 rests against the anterior vaginal wall 141 behind the symphysis pubis 142. The proximal end of the frame 104 rests against the vaginal epithelium in the posterior vaginal fornix. The proximal portion of the frame 104 and the paracervical electrodes 110 residing thereon rests in the lateral vaginal fornices 144. And the lateral portions of the frame 104 press gently on the lateral walls of the vagina 146 to help keep the intravaginal components 101 of the IVES device 100 in the proper position within the vagina 146. When the IVES device 101 is in the proper position inside the vagina 146, the IVC 102 will sit substantially in the middle portion of the vagina 146 and have a longitudinal orientation.

FIG. 13A shows an anterior transverse sectional view of the female pelvis with the intravaginal components in-situ within the vagina 146. FIG. 13B shows an enlarged view of the portion of FIG. 13A enclosed by the focus rectangle drawn over the upper vagina 146 and uterine cervix 148 in FIG. 13A. The upper vagina 150 and uterine cervix 148 are shown with the proximal end of the intravaginal components 101 in-situ to illustrate the proper positioning of the paracervical electrodes 110 in the lateral vaginal fornices 144.

Embodiments of the present invention may be manufactured in a variety of different sizes, and have a variety of longitudinal lengths for the frame 104 (for example from 6.5 to 8.5 centimeters, in increments of 5 millimeters) in order to accommodate the various vaginal depths of the women who may use the IVES device. The lateral flexibility of the frame 104 increases the IVES device's ability to address and accommodate differences in vaginal caliber among different women. The increased flexibility of the transitional portion 124 of the frame 104 and its propensity to return to its original configuration, when pressure placed upon it is released helps maintain the proper positioning of the paracervical electrodes 110 in the lateral vaginal fornices 144. The malleable sling 106 allows the intravaginal components 101 of the IVES device 100 to accommodate the overall shape of the vagina 146 for the women who may use the IVES device 100.

Figure 16:
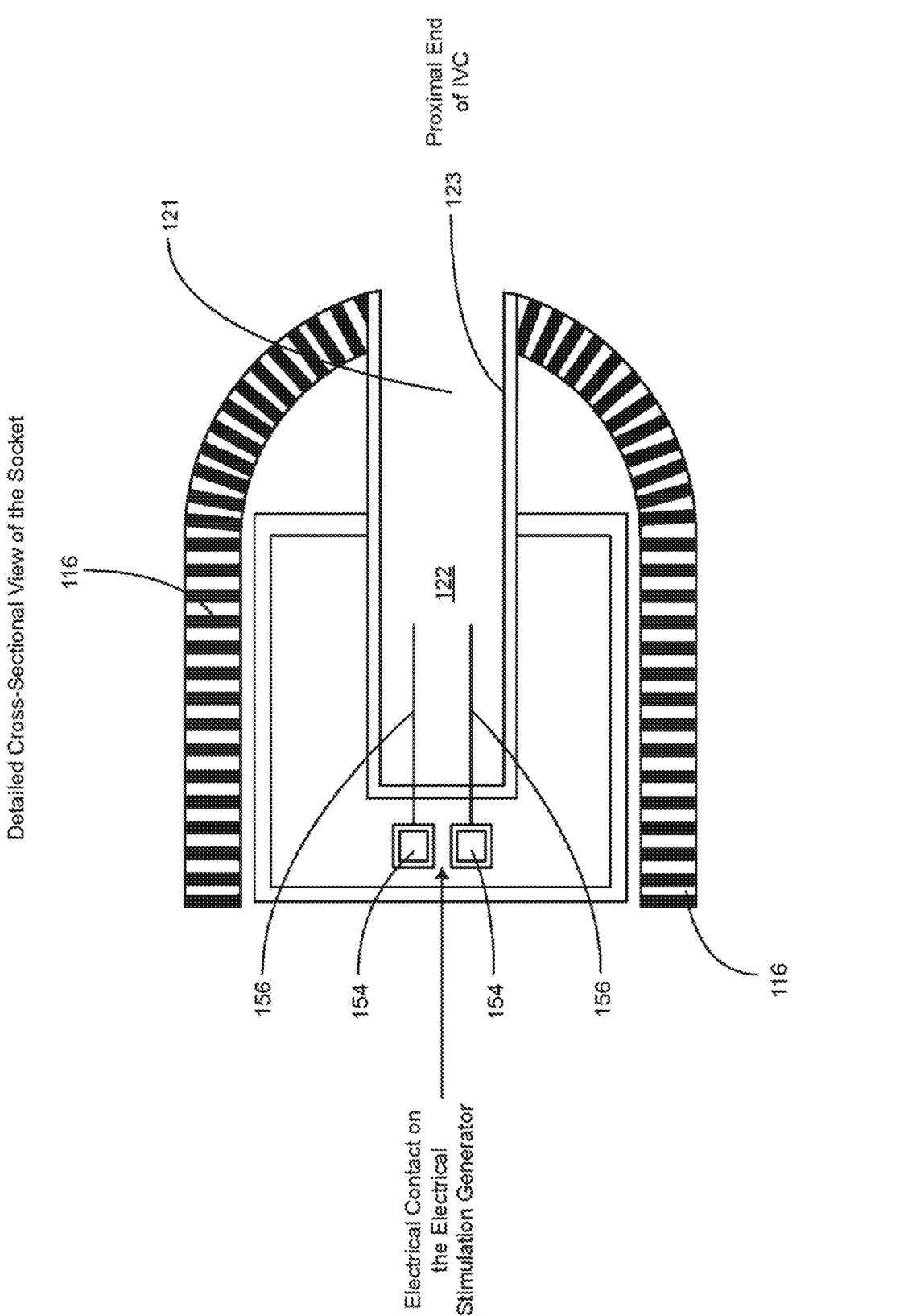
FIG. 16 shows a detailed cross-sectional view of the IVC socket in the proximal end of the IVC without the electrode plug inserted into the IVC socket.
Figure 18:
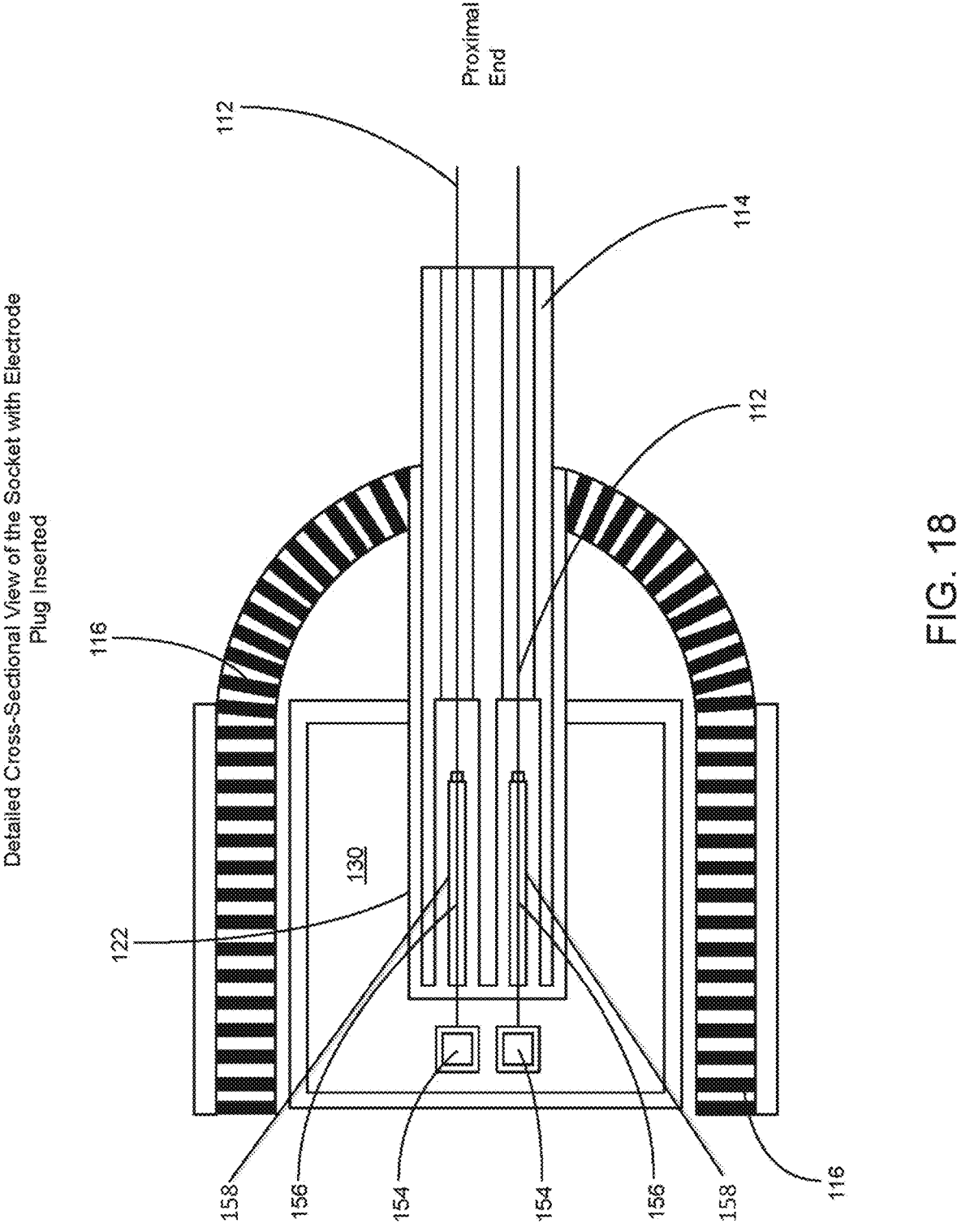
FIG. 18 shows a detailed cross-sectional view of the IVC socket with the electrode plug inserted into it in some embodiments of the present invention.

FIG. 14 shows a more detailed view of the IVES device 101, including the frame 104, the sling 106, the IVC pouch 108, the IVC 102, the IVC socket 122 in the IVC 102 (which is configured to receive the electrode plug 114). The IVES device 101 also includes one or more pairs of EUs 152. As shown in FIGS. 14, 16 and 18, the shell 116 of the IVC 102 comprises a hollow space defining an intravaginal cavity 120 that houses a number of electronic components, including the rechargeable battery 128, the inductive charging coil 127 that can be energized by placing it within range of an operating external inductive charger (not shown in the figures), a printed circuit board 126 and an electrical stimulation generator (ESG) 130. The printed circuit board 126 carries a radio frequency transceiver 138, a microprocessor 132, a memory 134, a local control program 136 in the memory 134 and an ESG 130.

The printed circuit board 126 is typically affixed to an interior wall 118 of the shell 116. The rechargeable battery 127, ESG 130, microprocessor 132, memory 134, local control program 136 and radio frequency transceiver 138 are all attached to the printed circuit board 126 to form an electrical circuit. The local control program 136 stored in the memory 134 comprises one or more programming modules having programming instructions that, when executed by the microprocessor 132, will cause the microprocessor 132 to perform certain functions herein described, including sending electronic signals to the ESG 130, and thereby control the output of the ESG 130. The characteristics (or profile) of the electrical stimulation produced by the ESG 130 may be varied by using, for example, constant current versus constant voltage, low frequency versus high frequency stimulation, tonic stimulation versus burst stimulation and by altering the pulse width, frequency and amplitude of the electrical stimulation being produced.

The radio frequency transceiver 138, operating under the control of the microprocessor 132 and the local control program 136, establishes a wireless data communications channel (typically using Bluetooth®, or some other near field communication protocol) with an application program (the "IVES remote control application or IVES app") 160 running on an external data communications device (the "external controller"), such as a smart phone, tablet computer or personal computer. The radio frequency transceiver uses the established wireless communication channel to receive data comprising operating instructions and other parameters for the IVES device 100 from the IVES app 160 on the external controller. The radio frequency transceiver 138 sends these incoming data, operating instructions and other parameters to the microprocessor, which executes programming instructions in the local control program 136 stored in the memory 134 to cause the ESG 130 to generate and send to the paracervical electrodes 110 electrical stimulations to stimulate the intrapelvic nerves in accordance with the instructions and parameters received from the IVES app 160 operating on the external controller 103 (which is discussed in more detail below). In preferred embodiments, the components of the IVC 102 can be configured to receive operating instructions and parameters over the wireless communications channel both before and after intravaginal components are placed inside the vagina 146. Suitably, the radio frequency transceiver 138 connected to the printed circuit board 126 of the IVC 102 may also be used to transmit status information (e.g., remaining battery charge) to the IVES app 160.

The ESG 130 operates under the control of the microprocessor 132 and the local control program 136, which tells the ESG 130 how to convert the current from the battery 128 into the appropriate electrical stimulation patterns ("ESP's") to be delivered to the intrapelvic nerves by way of the one or more ESCs, which are each comprised of a pair of related EUs 152. Preferably, a variety of different ESP's may be created, saved, recalled and activated by the patient by manipulating controls in the user interface of the IVES application program running on the external controller. Some of the features implemented in the user interface of the IVES application program 160 are discussed in more detail below.

The memory 134 on the printed circuit board 126 stores the programming instructions that comprise the local control program 136. When executed by the microprocessor 132, the programming instructions will cause the microprocessor 132 to carry out the steps of one or more predefined algorithms. These algorithms are typically executed in response to operating instructions and parameters input by the user via the user interface of the IVES app 160 running on the external controller 103. For example, the algorithms are typically arranged to allow the user to select and adjust the electrical stimulation patterns (ESP's) output by the ESG 130 in accordance with either pre-installed ESPs, or ESPs created by the user via the user interface. Preferably, the memory 134 also stores historical data regarding the operations and performance of the IVES device 100, which is periodically uploaded to the external controller 103 via the radio frequency transceiver 138 on the printed circuit board 126 of the IVC 102. Preferably, but not necessarily, IVES App 150 on the external controller 103 further includes program instructions that, when executed by the microprocessor 132, will cause the microprocessor 132 to use the radio frequency transceiver 126 in the external controller to wirelessly transmit historical data uploaded to the external controller 103 to other computing devices and made available to the patient's practitioner and/or others to improve the use of the IVES device 100 by the patient and others. The memory 134 may also store programming instructions that, when executed by the microprocessor, will cause the microprocessor to run a self-diagnostic test prior to sending electrical stimulation signals to the paracervical electrodes 110, and automatically generate a message for the user and then turn off the IVES device 100 should a fault be detected during the self-diagnostic test.

The Electrode Plug

The electrode plug 114 is suitably configured to be removably connected to the IVC 102 by insertion into the IVC socket 122 (shown best in FIGS. 14, 16 and 18). The electrode plug 114 is comprised of an electrode plug (see FIG. 17) made from a semi-firm compressible medical grade material surrounding one or more pairs of female electrical contacts 158 configured to receive corresponding male electrical contacts 156 at the distal end of the IVC socket 122 whenever the electrode plug 114 is inserted into the IVC socket 122. In some embodiments, the electrode plug 114 may have a slightly larger cross-section than the cross-sectional dimensions of the inside walls of the IVC socket 122. In such embodiments, the propensity of semi-firm compressible material used to make the electrode plug to return to its original shape once compressive forces place upon it are released make the connection between the IVC socket 122 and the electrode plug substantially moisture proof. In other embodiments, the electrode plug 114, the IVC socket 122, or both, may have detents holding O-rings to provide moisture protection for the electrical contacts or other elements of the electrode plug 114 and/or IVC socket 122. The shape of the perimeter walls of the electrode plug 114 and IVC socket 122 are designed so that corresponding male contacts at the distal portion of the IVC socket 122 and female contacts in the electrode plug are in alignment when the electrode plug 114 is inserted into the IVC socket 122. The electrode plug 114 may be removed from the IVC socket 122 in the IVC 102 and the IVC 102 may be removed from the IVC pouch 108 in order to completely separate the IVC 102 from the other components of the IVES device 100 for cleaning or replacement and to place the IVC 102 on the charging station to charge the battery in the IVC 102, for instance. It should be appreciated by one skilled in the art that, in an alternative embodiment, the male electrical contacts could be located in the electrode plug 114 and the female electrical contacts could be located in the IVC socket 122.

The electrode plug 114 is configured to receive and hold at least a pair of electrical contacts 158, connected to the electrode connecting wires 112 from the respective pair of EUs in the ESC, and the IVC socket 122 in the ESG 130 is configured to receive and hold (preferably in water-tight fashion) the electrode plug. Connecting the electrode plug 114 into the socket 122 in the IVC 102 permits the flow of electrical current between the ESG 130 in the IVC 108 and the paracervical electrodes 110 connected to the electrode plug 114.

Preferably, the ESG 130 in the IVC 102, the socket 122 in the IVC 102, and the electrode plug 114 are "multi-channeled," meaning the ESG 130 can be activated to create, maintain and control multiple ESCs and multiple electrical fields with differing characteristics, simultaneously, sequentially and/or in alternating fashion with current that may be direct current or alternating current to electrically neuro-modulate the intrapelvic nerves.

The Electrode Unit

Figure 15A:
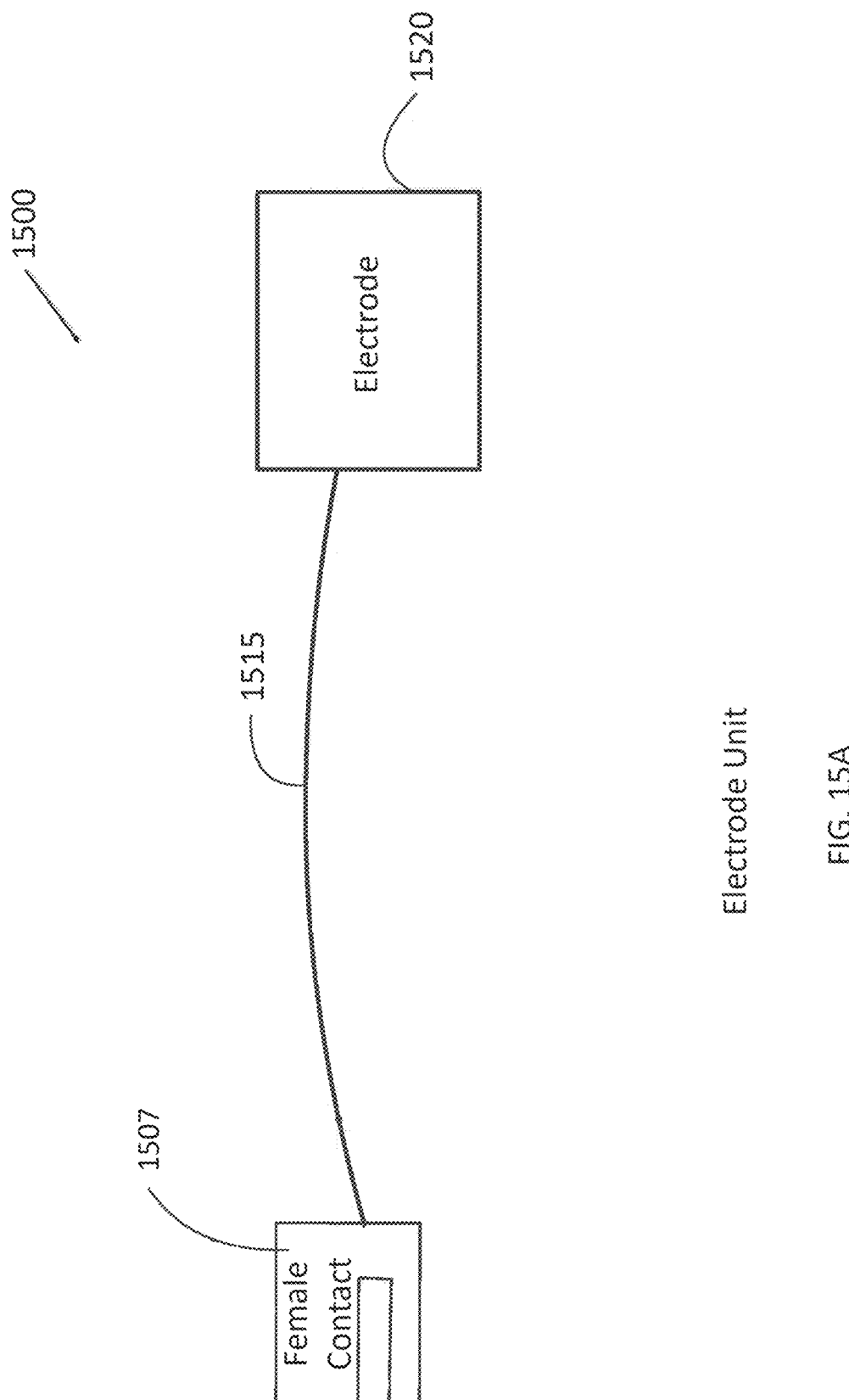
FIG. 15A shows a block diagram illustrating by way of example the components of an EU according to certain embodiments of the present invention.

FIG. 15A shows a block diagram illustrating by way of example the components of an electrode unit (EU) 1500 according to certain embodiments of the present invention. As shown in FIG. 15A, the EU 1500 comprises a female contact 1507, an electrode connecting wire 1515 and an electrode 1520. The female contact 1507 is configured to be located inside the electrode plug 1505 (shown in FIG. 15B) and to receive and electrically engage with a corresponding male contact 156 located in the socket 122 of an IVC 102 or an EESG (not shown in FIG. 15A).

Figure 15B:
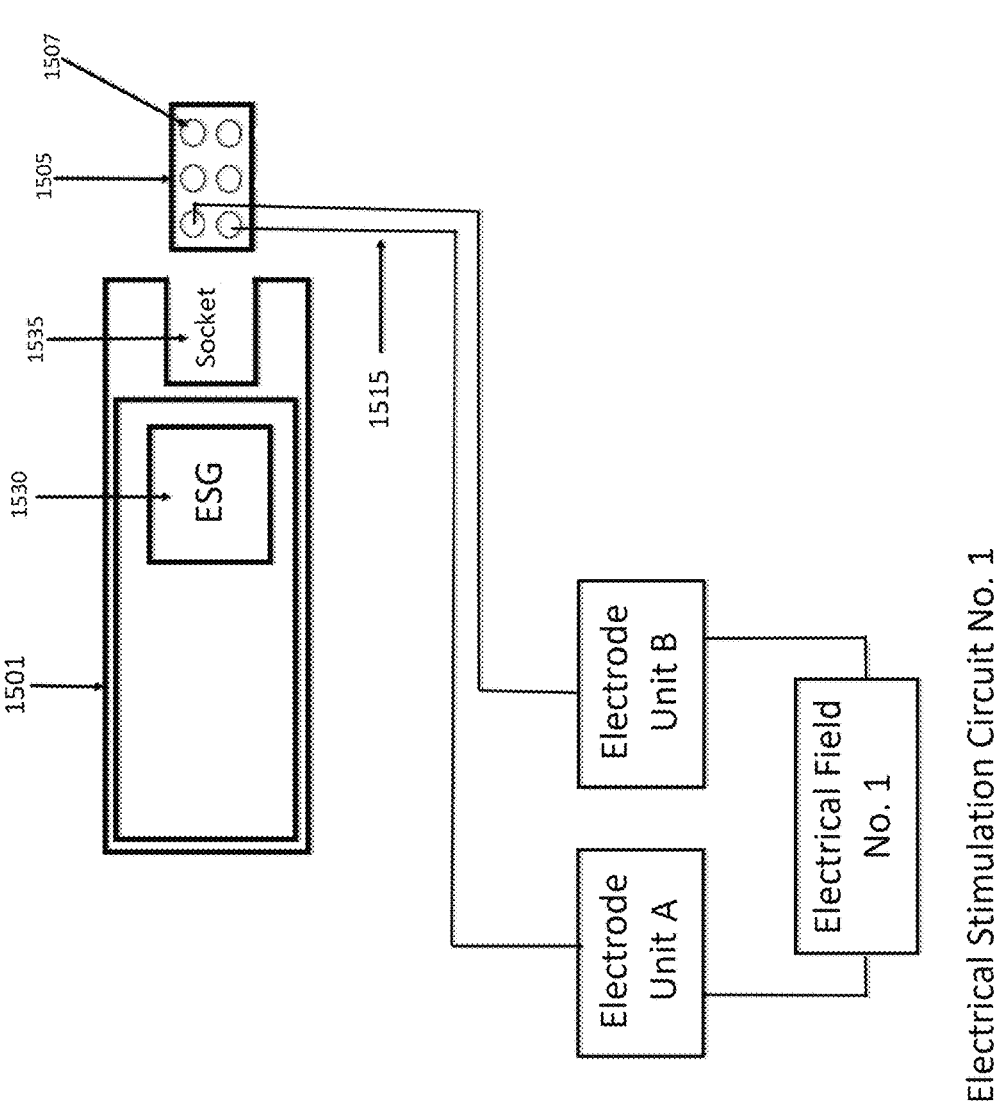
FIG. 15B shows a block diagram illustrating by way of example the components of an embodiment of the IVES device comprising a single ESC comprising a pair of EUs.

FIG. 15B shows a block diagram illustrating by way of example, the components of an embodiment of an IVES device where the ESG 1530 is contained in either an IVC or an EESG indicated by the reference numeral 1501. This embodiment has a single ESC (ESC No. 1) comprising a pair of EUs, EU-A and EU-B. Each individual electrode in the EU is electrically connected to the female contact 1507 in the electrode plug (1505), which makes an electrical connection with a corresponding male contact (not shown) in the socket 1535 when the electrode plug 1505 is inserted into and engaged with the socket 1530 in the IVC or EESG 1501.

Although the electrical contacts 1507 in the electrode plug 1505 are described above as a "female" contacts configured to be electrically engaged with corresponding "male" contacts 156 in the socket 1535, it will be recognized and appreciated by those skilled in the art that the particular kinds and shapes of the electrical contacts are not a critical aspect of the claimed invention. For example, instead of putting female electrical contacts in the electrode plug and male electrical contacts in the socket, the electrical connections in embodiments of the invention may be suitably implemented by putting male electrical contacts in the electrode plug and female electrical contacts in the socket without negatively impacting the performance of the IVES device or departing from the scope of the claimed invention. Similarly, instead of using what are generally considered to be male to female electrical contacts, embodiments of the present invention may successfully implement the electrical connections using, for example, button-to-button electrical contacts, spring-to-button electrical contacts, ring-to-ring contacts, or any other kind of electrical contact, so long as the kind of electrical contacts selected are capable of passing electrical current from one segment of an electrical circuit to another segment of the electrical circuit.

Figure 15C:
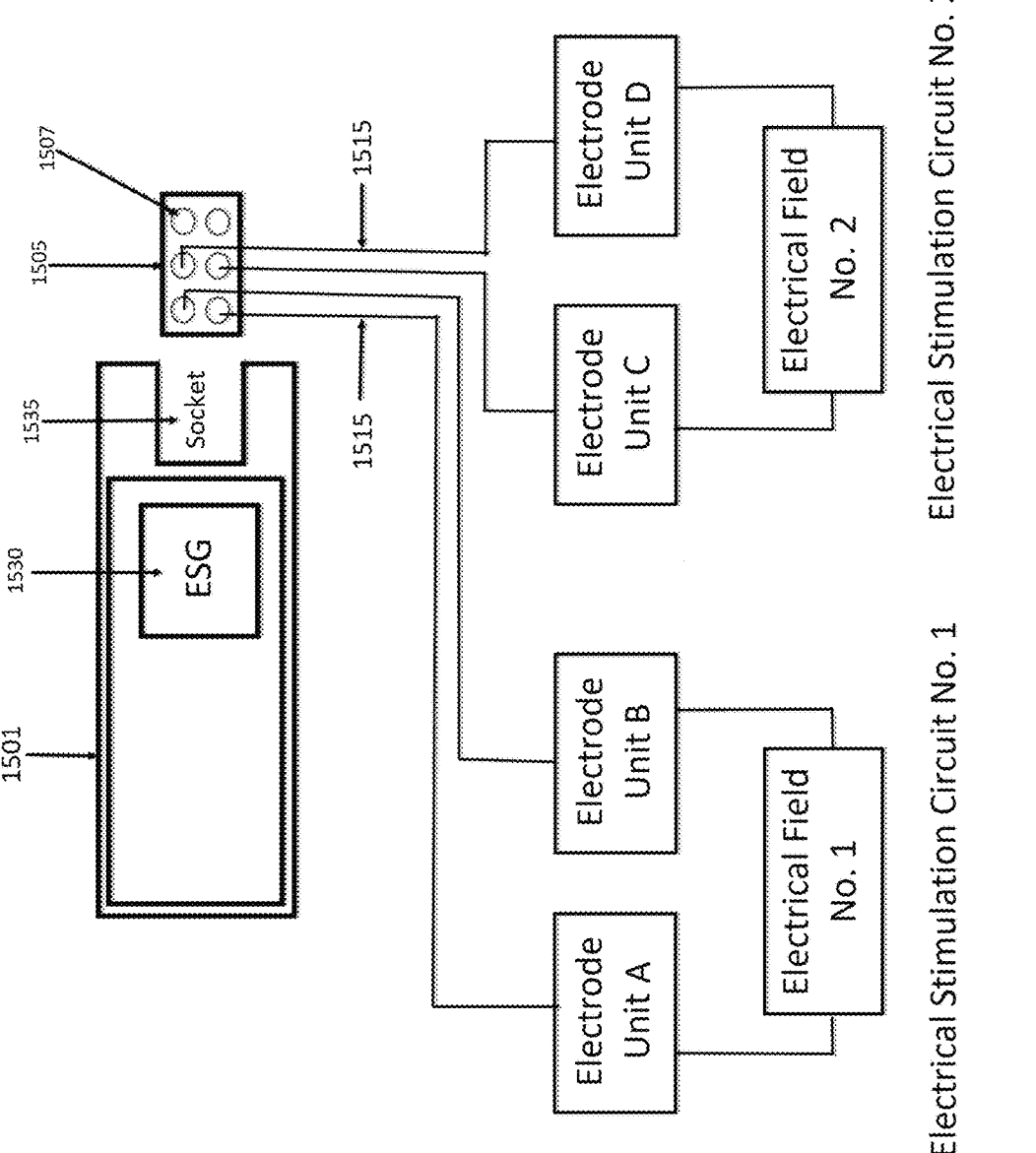
FIG. 15C shows a block diagram illustrating by way of example the components of an embodiment of the IVES device comprising two ESCs comprising two pairs of EUs.
Figure 15D:
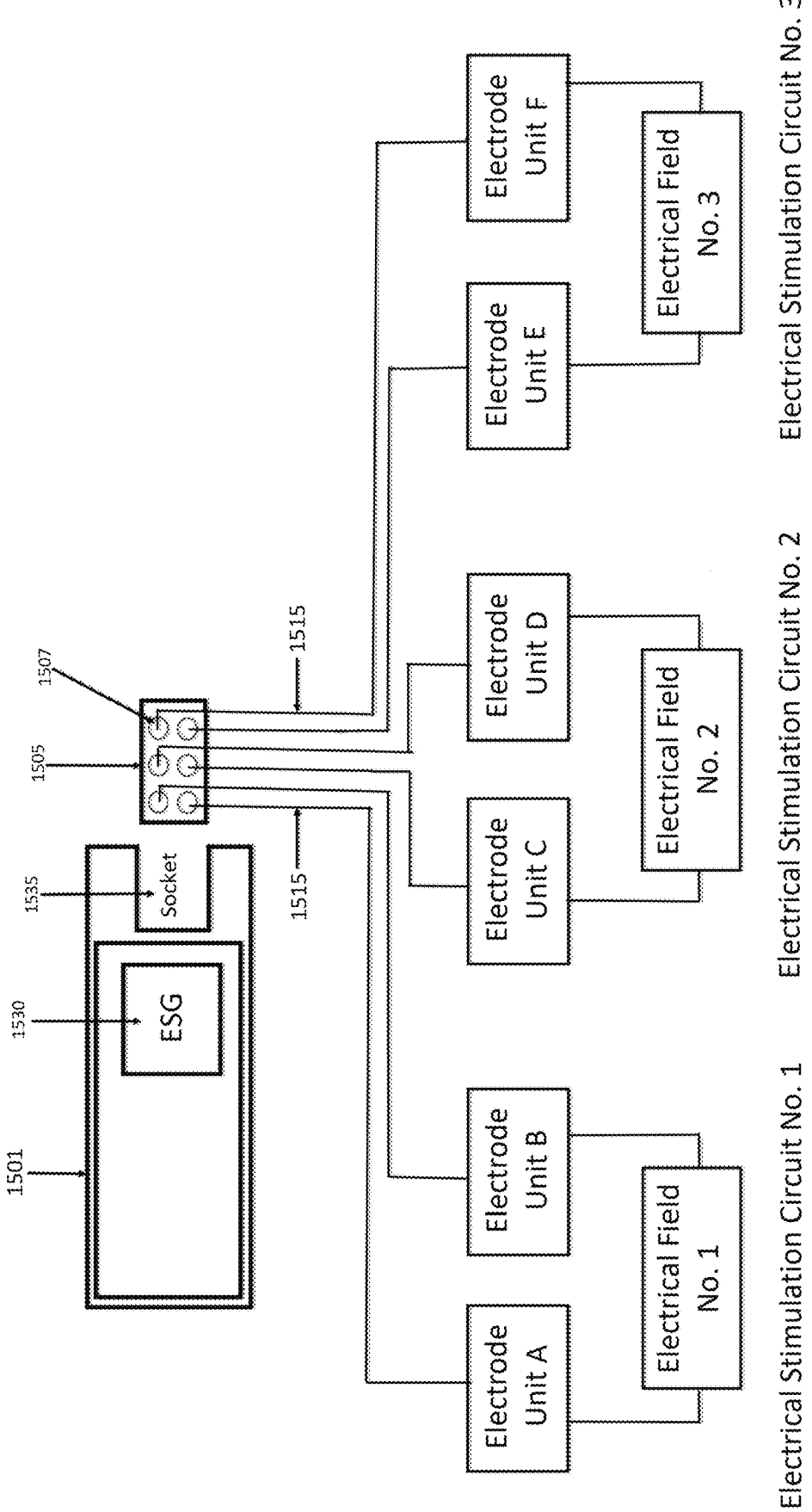
FIG. 15D shows a block diagram illustrating by way of example the components of an embodiment of the IVES device comprising three ESCs comprising three pairs of EUs.

To accommodate a multiplicity of EUs, the electrode plug 1505 is configured to receive multiple electrode connecting wires 1515, (each connected to an individual electrode in an EU), that are electrically connected to the female electrical connection 1507 in the plug 1505. In FIGS. 15B, 15C and 15D, for example, the electrode plug 1505 has 6 female electrical connections 1507 that can connect to six electrode connecting wires 1515 in six EUs (associated with three different ESCs, respectively). These female electrical connections 1507 in the electrode plug 1505 connects to the corresponding male electrical connections (not shown) in the socket 1535 present in an IVC or EESG 1501.

In the example of FIG. 15B, the electrode connecting wires 1515 of EU-A and EU-B are connected to the two female electrical connections 1507 shown on the left portion of the electrode plug 1505, leaving four additional female electrical connections 1507 in the electrode plug 1505 open and available to create four additional EUs (corresponding to two more ESCs). When the ESG 1530 is activated, the electric field No. 1 created between EU-A and EU-B completes the electrical circuit and permits the low-voltage current to flow between the ESG and the electrical field No. 1 by way of the socket 1535, the electrode plug 1505, EU-A and EU-B.

FIG. 15C shows a block diagram illustrating by way of example, the components of an embodiment of an IVES device where the ESG 1530 is contained in either an IVC or an EESG indicated by the reference numeral 1501. This embodiment has two ESCs (ESC No. 1 and ESC No. 2), each comprised of a pair of EUs, with ESC No. 1 being comprised of EUs A and B to generate electrical field No. 1, and ESC No. 2 being comprised of EUs C and D to generate electrical field No. 2. All of the electrode connecting wires in EUs A-D are electrically connected to a female contact (1507) in the electrode plug (1505), which makes an electrical connection with the male contact (not shown) in the socket 1535 when the electrode plug 1505 is inserted into and engaged with the socket 1530.

FIG. 15D shows a block diagram illustrating by way of example the components of an embodiment of the IVES device where the ESG 1530 is contained in either an IVC or an EESG indicated by the reference numeral 1501. This embodiment has three ESCs (ESC No. 1, ESC No. 2 and ESC No. 3) and three pairs of EUs. ESC No. 1 comprises EUs A and B to generate electrical field No. 1, ESC No. 2 comprises EUs C and D to generate electrical field No. 2, and ESC No. 3 comprises EUs E and F to generate electrical field No. 3. All of the electrode connecting wires for EUs A-F are electrically connected to a female contact (1507) in the electrode plug (1505), which makes an electrical connection with the male contact (not shown) in the socket 1535 when the electrode plug 1505 is inserted into and engaged with the socket 1530. Those skilled in the art will recognize and appreciate that the electrode plug 1505 and the socket 1535 in an IVC or EESG 1501 may be built with multiple EUs and ESCs, some of which may not be activated during the treatment of a patient.

Figure 15E:
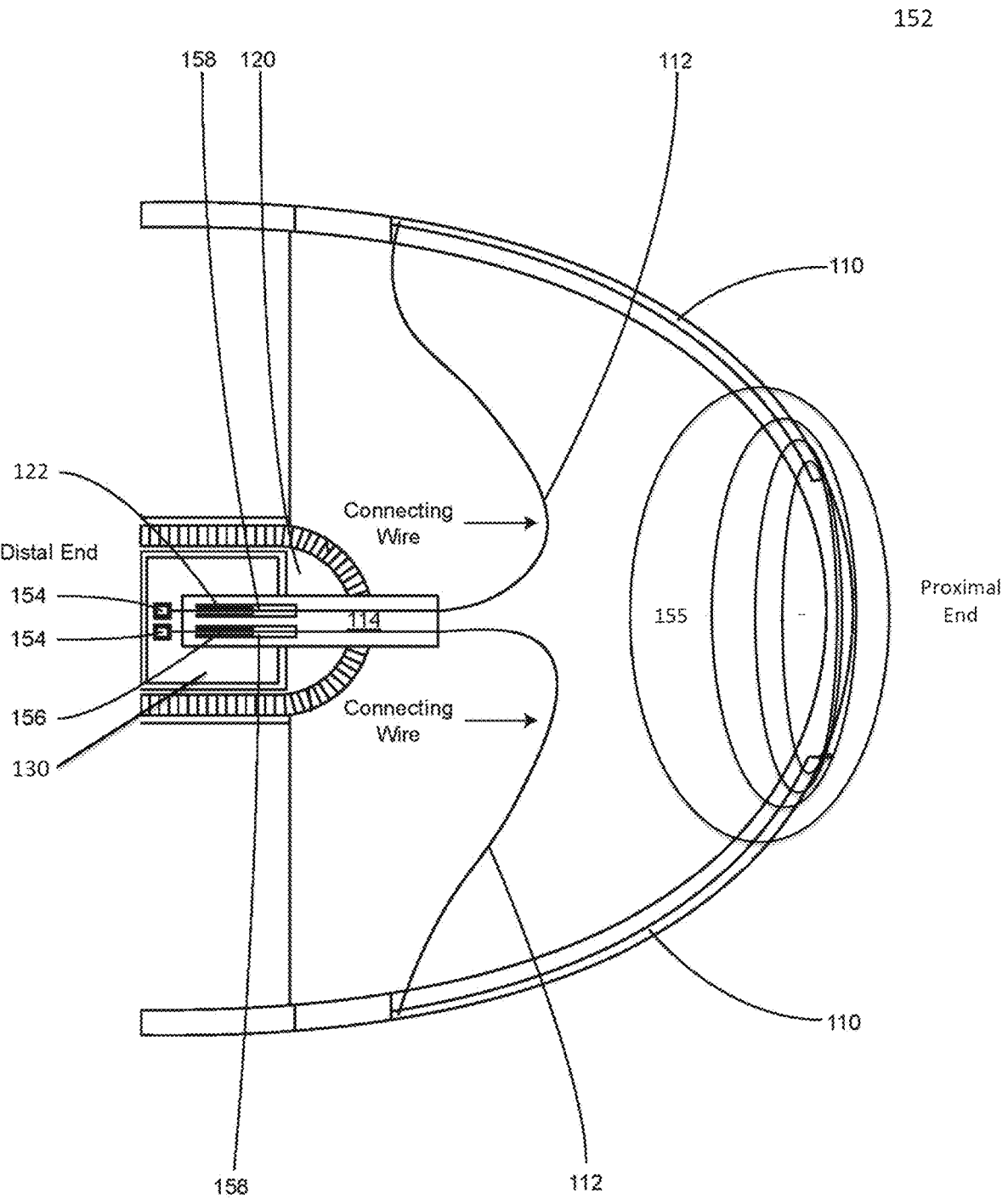
FIG. 15E shows the components of an embodiment of the IVES device with a single ESC used create a single electrical field with a pair of paracervical electrodes.

FIG. 15E shows the components of an embodiment of the IVES device with a pair of paracervical electrodes 110 electrically connected to an ESG 130 located in an IVC 120 via an electrode plug 114 a socket 122 and a pair of paracervical electrode connecting wires 112. In this embodiment a single electrical field 155 is created between the pair of paracervical electrodes 110 when the ESG 130 is activated.

The characteristics of the electrical field 155 may be customized to deliver a specific electrical stimulation pattern to the intrapelvic nerves. Multiple pairs of EUs can create multiple electrical fields to deliver multiple electrical stimulation patterns to the intrapelvic nerves at the same time. Thus, the electronic signals sent to the ESG 130 by the microprocessor 132 operating under the control of the local control program 136 running in the memory 134 may be programmed to cause the ESG 130 to transmit one or more electrical stimulation patterns through one or more pairs of EUs AB, CD or EF, causing neuromodulation of the pelvic, paracervical nerves and sacral nerves, which results in the decrease or elimination of pelvic pain.

FIG. 16 shows a detailed cross-sectional view of the IVC socket 122 in the proximal end of the IVC 102 without the electrode plug 114 inserted into the IVC socket 122. The IVC socket 122 includes two male electrical connections in its base in the form of protruding pins 156, extending from two electrical contacts 154, respectively, located on the ESG 130 in the IVC 102. The two protruding pins 156 are configured to engage the female electrical contacts 158 located in the electrode plug 114.

Figure 17:
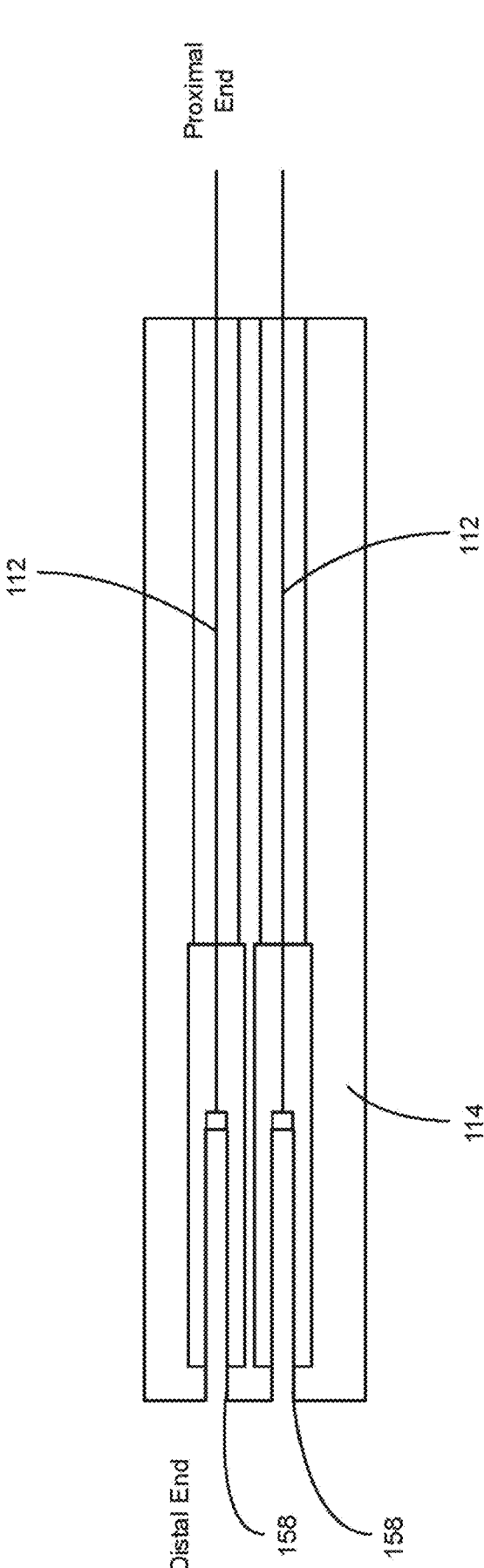
FIG. 17 shows a detailed cross-sectional view of the electrode plug with a pair of female electrical contacts in its distal end when the electrode plug has not been inserted into the IVC socket.

FIG. 17 shows a detailed cross-sectional view of the electrode plug 114 surrounding a pair of female electrical contacts 158. The female electrical contacts 158 are configured to mate with corresponding male contacts (not shown) located in the IVC socket 122 shown in FIG. 16. A pair of electrodes connecting wires 112 electrically couple the female contacts 158 to a pair of paracervical electrodes (not shown in FIG. 17).

FIG. 18 shows a detailed cross-sectional view of the IVC socket 122 with the electrode plug 114 inserted into it in some embodiments of the present invention.

As shown in FIGS. 16, 17 and 18, the IVC 102 has in its proximal end an IVC socket 122 configured to receive and removably hold the electrode plug 114. In some embodiments, the IVC socket 122 defines a cylindrical space 121 with the sidewalls 123 of the cylindrical space 121 and the base of the cylindrical space 121 at its distal end forming a physical barrier between the interior cavity 120 of the IVC 102 and the environment outside the IVC 102 to protect the printed circuit board 126 and other electronic components within the IVC 102 from moisture. In other embodiments, the sidewalls 123 of the IVC socket 122 may instead define a space having a different geometric shape, such as, for example, a half-cylinder shape, a rectangular solid or a triangular solid. In any case, the electrode plug 114 is suitably configured to have a size and shape that complements the inner space defined by the sidewalls 123 of the IVC socket 122 so as to enable easy insertion of the electrode plug 114 into the IVC socket 122, and is designed to create a moisture proof seal between it and the IVC socket 122. Located at the distal end of the IVC socket 122 are male electrical contacts 156 that are electrically coupled to electrical contacts 154 on the ESG 130 on the printed circuit board 126 inside the interior cavity 120 of the IVC shell 116. Built into the electrode plug 114 are female electrical contacts 158 configured to engage the corresponding male electrical contacts 156 at the distal end of the socket 122 in the IVC 102.

As has been previously described, the paracervical electrodes 110 embedded in the surface of the covering of the proximal portion of the frame 104 are positioned so they will remain in contact with the paracervical vaginal epithelium of the lateral vaginal fornices while the IVES device is in use. When the male electrical contacts 156 at the distal end of the socket 122 in the IVC 102 are engaged with the female contacts 158 in the electrode plug 114, and the IVES device is switched on and operating, the ESG 130 (under the control of the microprocessor 132 and local control program 136) generates an electrical potential (voltage) that causes low-voltage electrical current to flow through an ESC with a pair of paracervical electrodes. The electric field created between the electrodes causes neuromodulation of the intrapelvic nerves, resulting in a reduction or elimination of pelvic pain.

Responding to instructions from the external comptroller 103 and under the control of the local control program 136 in the memory 134 of the IVC 102, the characteristics of the electrical stimulation produced by the ESG 130 may be varied by using, for example, direct-current or alternating current, constant current or constant voltage, low frequency or high frequency stimulation, tonic versus burst stimulation and by altering the pulse width, frequency and amplitude of the electrical stimulation being produced. Neuromodulation of the intrapelvic nerves due to the electrical stimulation they receive will reduce or eliminate the pain associated with dysmenorrhea, dyspareunia and chronic pelvic pain originating in the uterus and other organs in the pelvis.

Figure 19A:
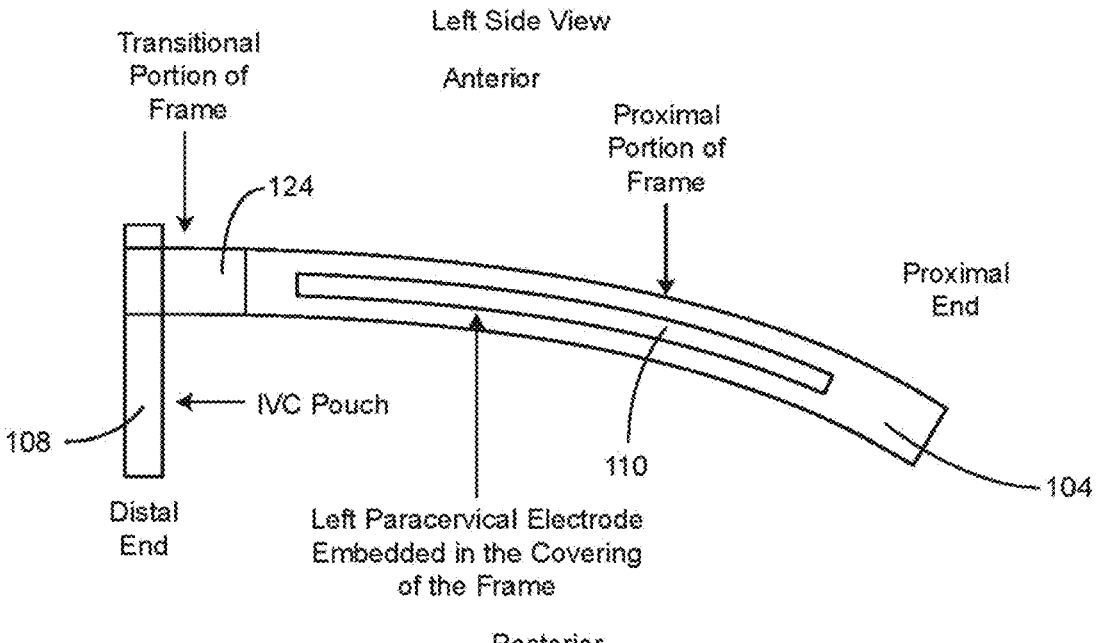
FIGS. 19A and 19B shows the positioning of a pair of paracervical electrodes embedded in the surface covering of the proximal portion of the frame with one electrode embedded on each side of the frame.
Figure 19B:
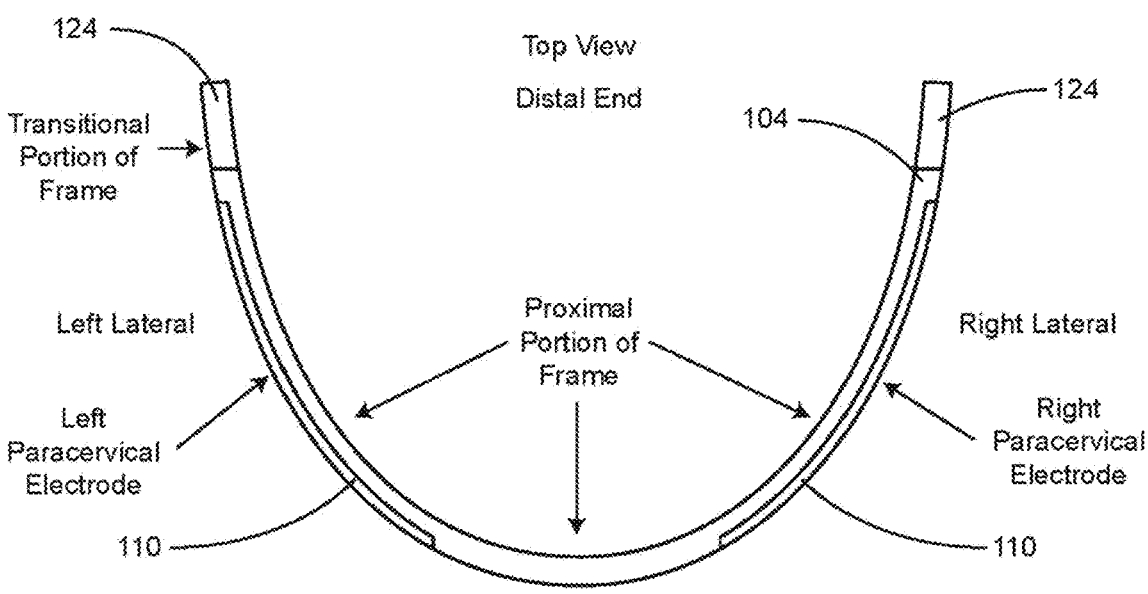

FIGS. 19A and 19B. show the positioning of the paracervical electrodes 110 embedded in the surface covering of the proximal portion of the frame 104 in an embodiment of the IVES device 100 where one pair of EUs are being used to create a single ESC to produce a single electrical field between the paracervical electrodes 110.

Figure 20:
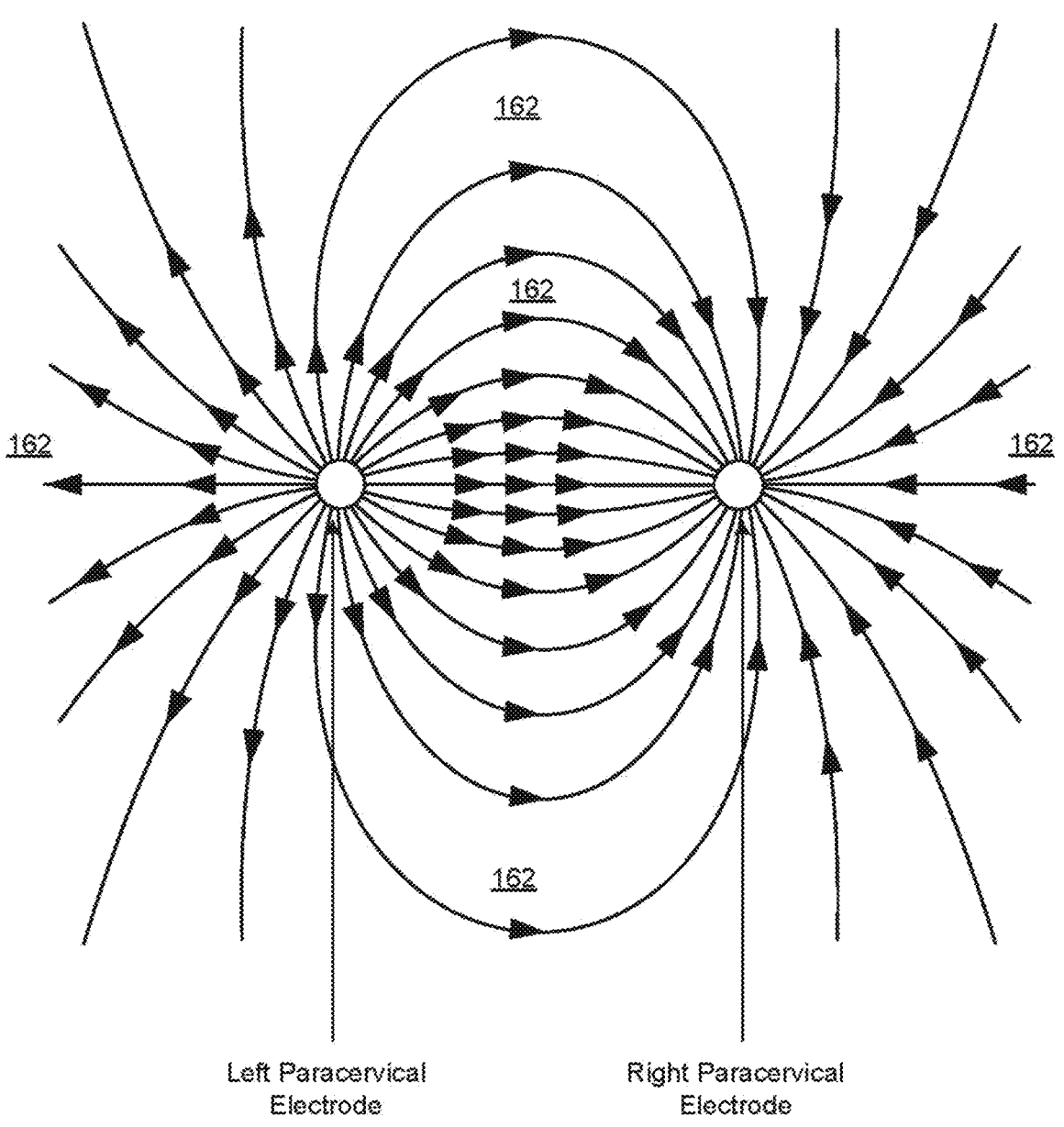
FIG. 20 shows a schematic representation of the electrical field generated by a single ESC with a pair of paracervical electrodes positioned as shown in FIGS. 19A and 19B.

FIG. 20 shows a schematic representation of the electrical field 162 generated by a single ESC with a pair of paracervical electrodes 110 positioned as shown in FIGS. 19A and 19B.

Figure 21A:
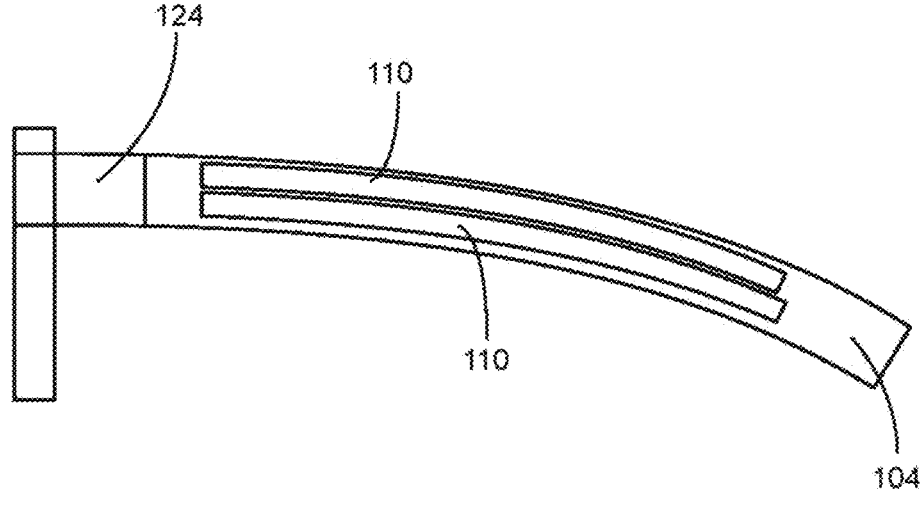
FIGS. 21A and 21B show the positioning of two pairs of paracervical electrodes embedded in the surface covering of the proximal portion of the frame in an embodiment of the IVES device where two pairs of EUs are used to create two ESCs.
Figure 21B:
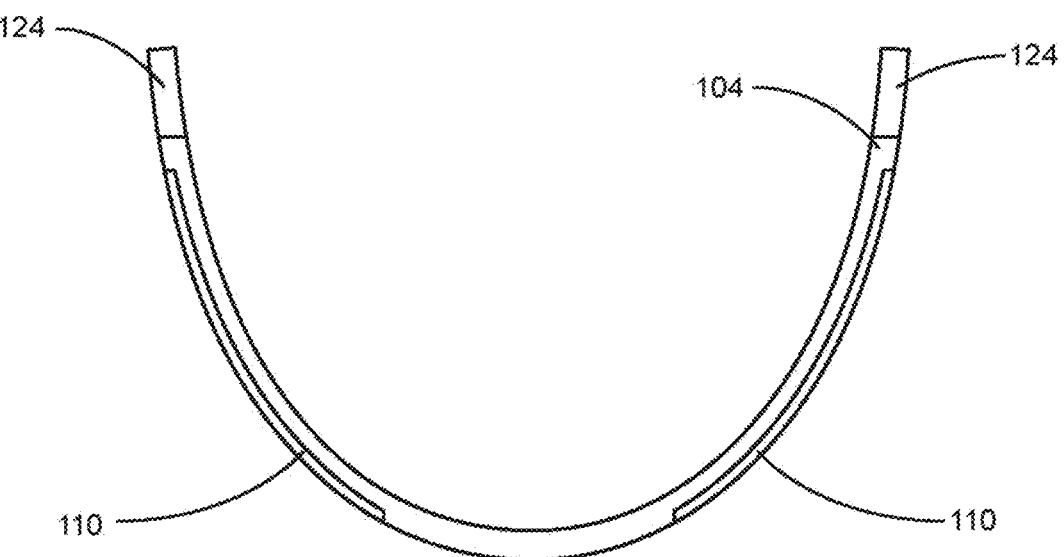

FIGS. 21A and 21B shows the positioning of two pairs of paracervical electrodes 110 embedded in the surface covering of the proximal portion of the frame 104 in an embodiment of the IVES device 100 where two pairs of EUs are used to create two ESCs.

Figure 22:
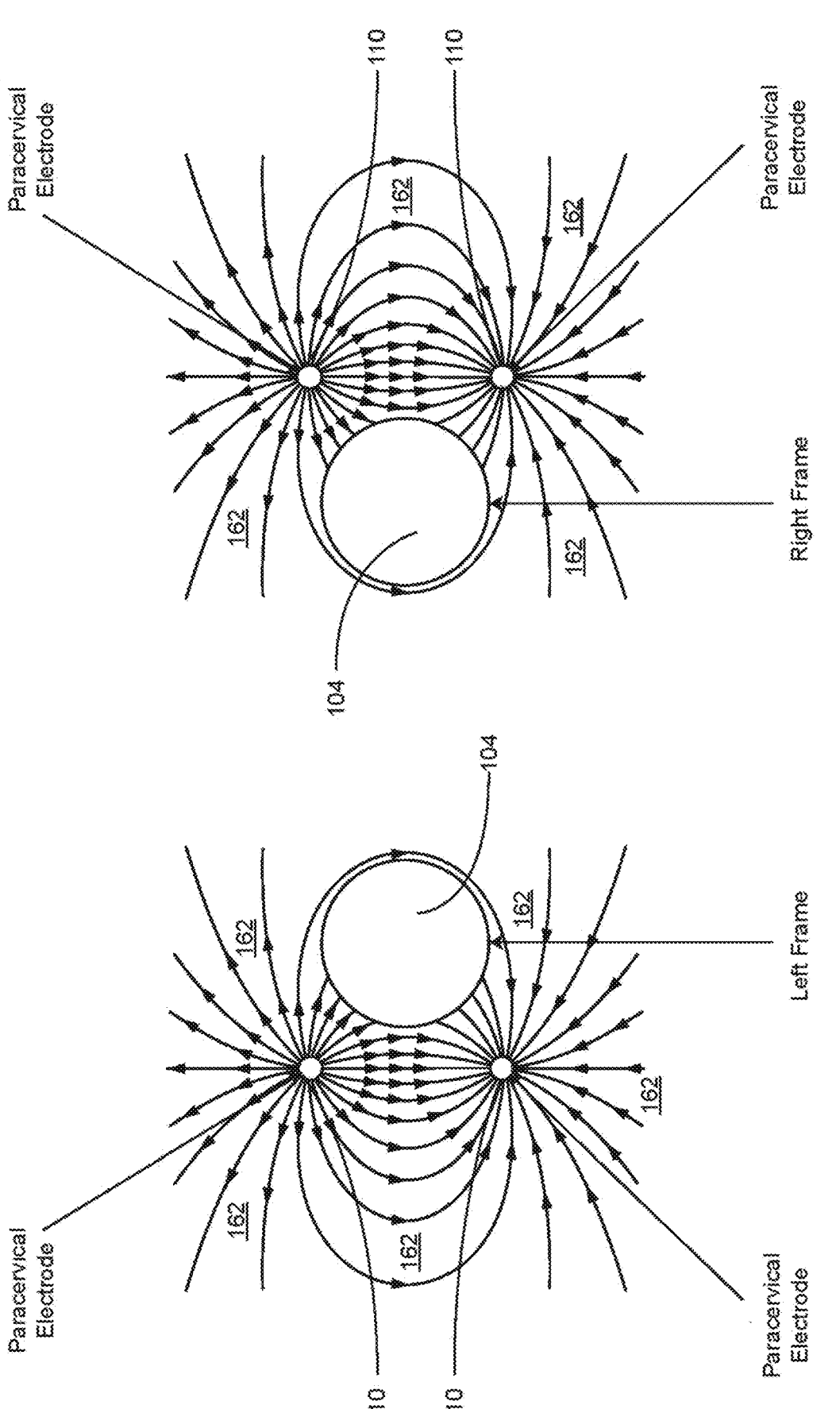
FIG. 22 shows a schematic representation of the electrical fields generated by two ESCs with two pairs of paracervical electrodes positioned as shown in FIGS. 21A and 21B if the paracervical electrodes of each ESC are located on the same side of the frame.

FIG. 22 shows a schematic representation of the electrical fields 162 generated by two ESCs with two pairs of paracervical electrodes 110 positioned as shown in FIGS. 21A and 21B if both of the paracervical electrodes in each ESC are located on the same side of the frame 104.

Figure 23:
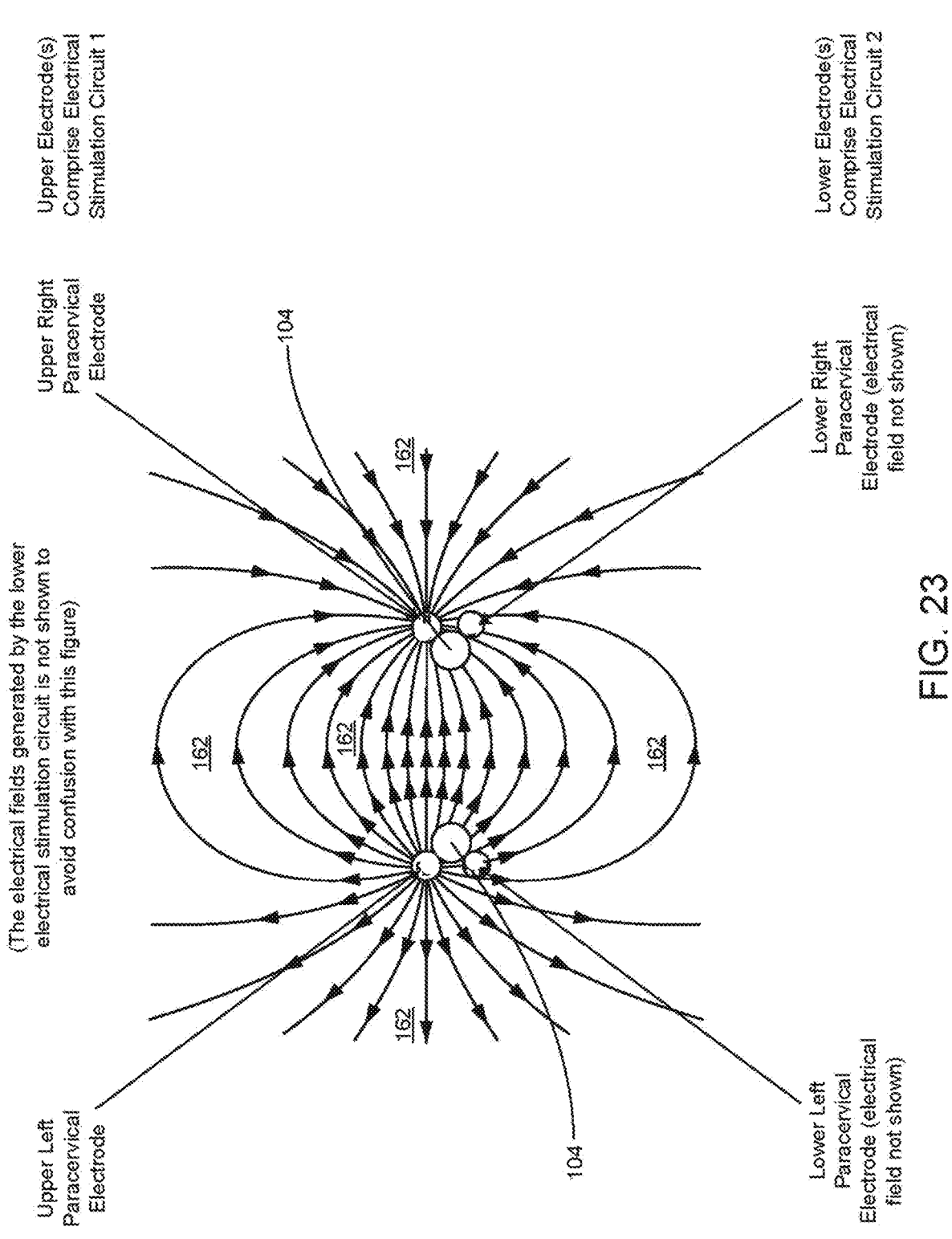
FIG. 23 shows a schematic representation of one of the two electrical fields generated by two ESCs with two pairs of paracervical electrodes positioned as shown in FIGS. 21A and 21B if the paracervical electrodes of each ESC are located on opposite sides of the frame.

FIG. 23 shows a schematic representation of one of the two electrical fields generated by two ESCs with two pairs of paracervical electrodes 110 positioned as shown in FIGS. 21A and 21B if the paracervical electrodes in each ESC are located on opposite sides of the frame 104. A representation of the second electrical field generated by the second ESC is not shown to avoid confusion within the figure.

The External Controller and the IVES Control Application (the "IVES App")

Figure 24:
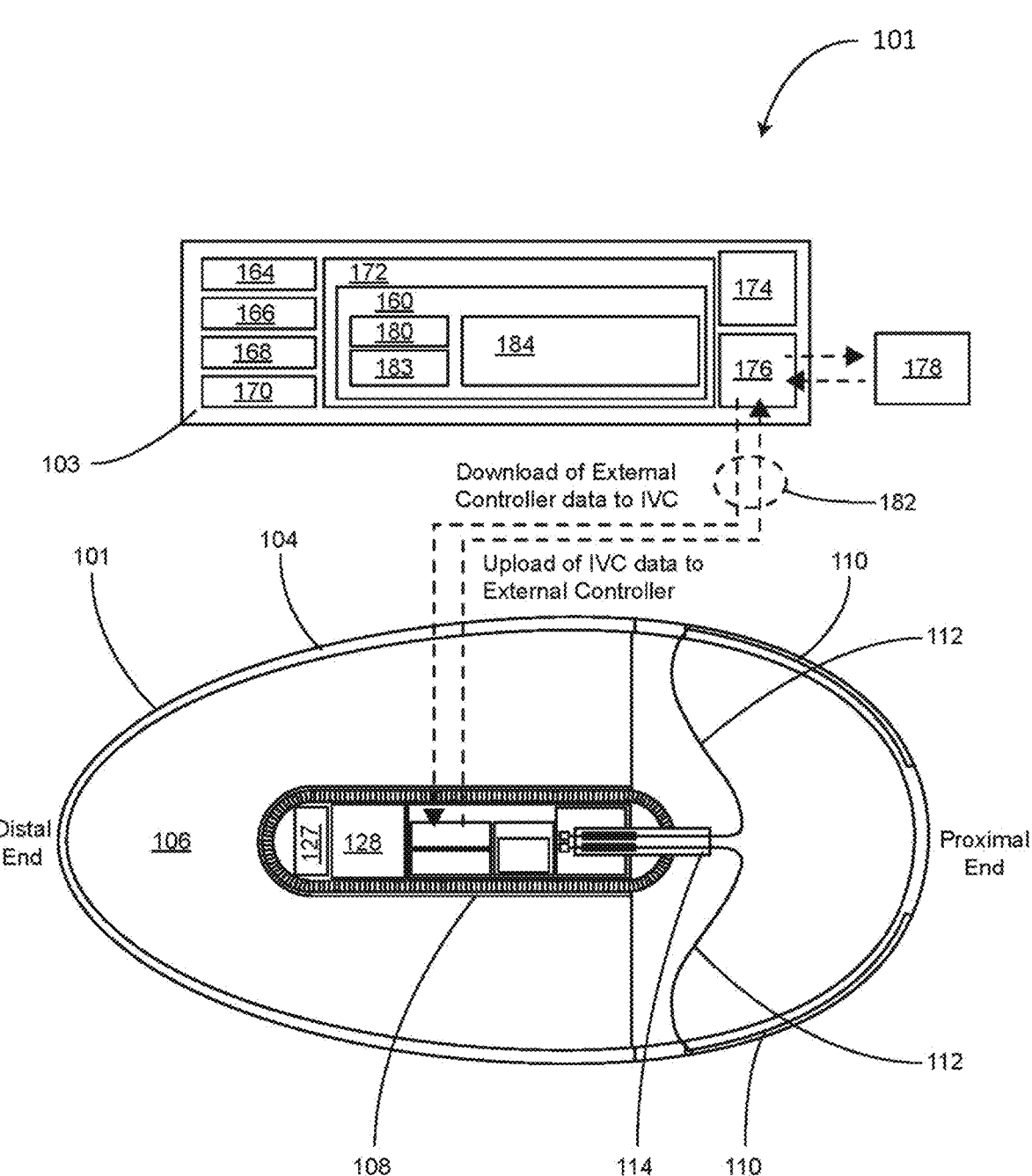
FIG. 24 shows a high-level block diagram, illustrating by way of example, both the intravaginal components and the external controller in an IVES device configured to operate in accordance with embodiments of the present invention.

FIG. 24 shows a high-level block diagram, illustrating by way of example, both the intravaginal components 101 and the external controller 103 according to certain embodiments of the present invention. As shown in FIG. 24, the external controller 103, which may comprise a tablet computer, a smart phone, a personal computer or any other type of computing or data communications device, includes a microprocessor 164, a volatile memory storage area for temporary storage of compiled and executable program instructions suitable for execution on the microprocessor 164, a display screen 168, an input device 170, such as a keyboard or touchscreen, a static memory 172 for storing an application program, a battery 174 and a radio frequency transceiver 176. The radio frequency transceiver 176 is configured to establish a wireless communication channel 182 with the radio frequency transceiver 138 inside the IVC 102. The static memory 172 stores the programming instructions for the IVES app 160. When executed by the microprocessor 164 on the external controller 103, the programming instructions in the IVES app 160 will cause the microprocessor 164 on the external controller 103 to communicate with the microprocessor 132 inside the IVC 102 via the wireless data communications channel 182 established between the two radio frequency transceivers.

The User Interface

A user interface module 180 in the IVES app 160 is configured to receive operating instructions from the user, which permits the user to activate, adjust and tune the electrical stimulation being delivered by ESG 130 to the paracervical electrodes 110, as well as other settings 184 available for changing using the user interface module 180. Thus, the user can manipulate controls on a display screen 168 of the external controller 103 (such as digital representations of buttons, icons and sliders) in the user interface on the external controller 103 to select, personalize, optimize, adjust, activate and/or deactivate the electrical stimulation provided to the intrapelvic nerves by the IVES device 100. In addition, the radio frequency transceiver 176 and the microprocessor 164 inside the external controller 103 can receive over the wireless communication channel 182 status indicators 183 and other data generated by the microprocessor 132 connected to the printed circuit board 126 inside the shell 116 of the IVC 102, and/or data stored in the memory 134 on the printed circuit board 126 inside the shell 116 of the IVC 102. The status information 183 and other data may be displayed on the display screen 168 associated with the external controller 103 via the user interface. Preferably, the user interface module 180 of the IVES app 160 running on the external controller 103 also includes program instructions configured to permit the external controller 103 or the user to use email, text messages and/or another data or information transmitting processes to send the status information 184 and other data retrieved from the memory 134 of the IVC 102 to other devices, organizations or people, such as, for example, the user's personal physician or other health care provider.

Preferably, the IVES app 160 stored in the memory storage area 172 of the external controller 103 also includes program instructions that permit the external controller 103 to periodically query a remote computer system or server 178 to determine (1) whether any program updates associated with the IVES app 160 running on the external controller 103 are available, and/or (2) whether operating system updates, local program updates or firmware updates associated with the local control program 136 stored in the memory 134 of the IVC 102 are available. If such an update is available, the IVES app 160 is configured to automatically download and install it on the external controller 103, on the IVC 102, and/or both. By downloading such updates as they become available, the IVES app 160 running on the external controller 103, as well as the operating system, local control program 136 and firmware running on the IVC 102 will automatically remain substantially up-to-date with the latest bug fixes and/or improvements. In some embodiments, the IVES app 160 may be configured to prompt the user for permission or confirmation before downloading and/or installing program, operating system or firmware updates.

In preferred embodiments, the user may also select and activate a previously saved electrical stimulation profile (ESP) or a newly created ESP, which can then be saved to the memory 134 of the IVC 102. Once these operating instructions and parameters and preferred settings have been entered and saved on the external controller 103 using the user interface module 180, the microprocessor 164, still operating under the control of the IVES app 160, activates the radio frequency transceiver 176 to establish a wireless data communications link 182 with the radio frequency transceiver 138 inside the cylindrical shell 116 of the IVC 102. Then the microprocessor 164 uses the wireless data communications link 182 to transmit the operating parameters and preferred settings to the memory 134 inside the IVC 102. The IVES app 160 may also contain program instructions that, when executed by the microprocessor 164, will cause the microprocessor 164 to upload the status information 183 from the IVC 102 and show the status information 183 on the display screen 168. The status information 183 may include, for example, the amount of battery power remaining on the rechargeable battery 128 attached to the printed circuit board 126 of the IVC 102.

FIGS. 25A, 25B, 26A, 26B, 27A, 27B, 28A, 28B, 29A and 29B show, by way of example, a collection of user interface screenshots that might be used to operate, control and modulate IVES devices in accordance with an embodiment of the present invention. As shown in these figures, the display screen 168 communicatively connected to the user interface module 180 comprises a multiplicity of icons, buttons and sliders configured to control the operation of the IVES device 100 by sending the appropriate control signals over the wireless communication channel via the radio frequency radios inside the external controller and the IVC 102

Figure 25B:
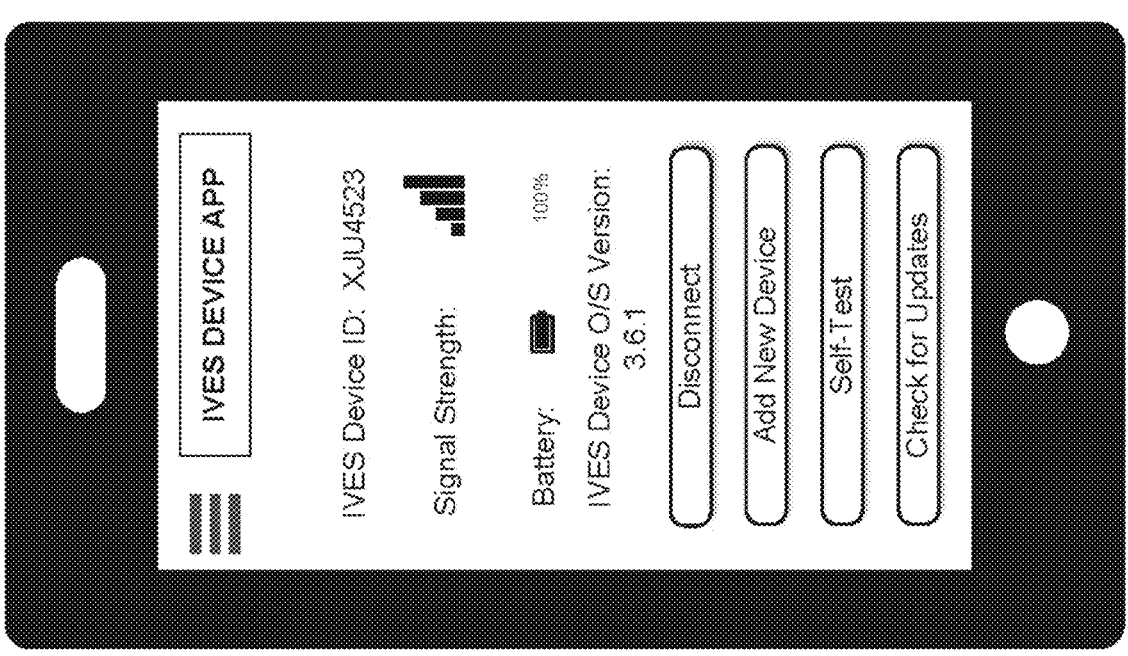
FIGS. 25A, 25B, 26A, 26B, 27A, 27B, 28A, 28B, 29A and 29B show, by way of example, a collection of user interface screenshots that might be used to activate, deactivate, operate, control and modulate the output of IVES devices constructed in accordance with an embodiment of the present invention.
Figure 25A:
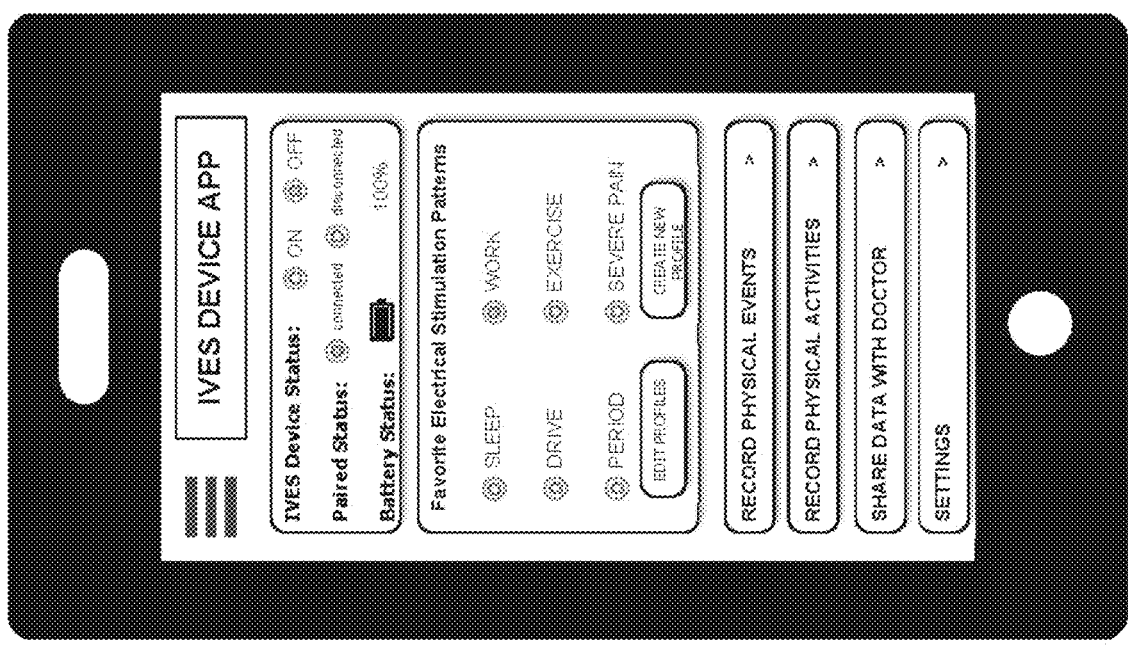

Among other things, the user interface may be programmed to provide a variety of useful functions, including but not limited to:

[1] Switching the IVES device on and off (FIG. 25A— "on/off" radio buttons).

[2] Displaying the current operating status and battery charge level for the IVES device (FIGS. 25A and 25B).

[3] Warning the patient when the battery charge level is low (FIGS. 25A and 25B).

Figure 26B:
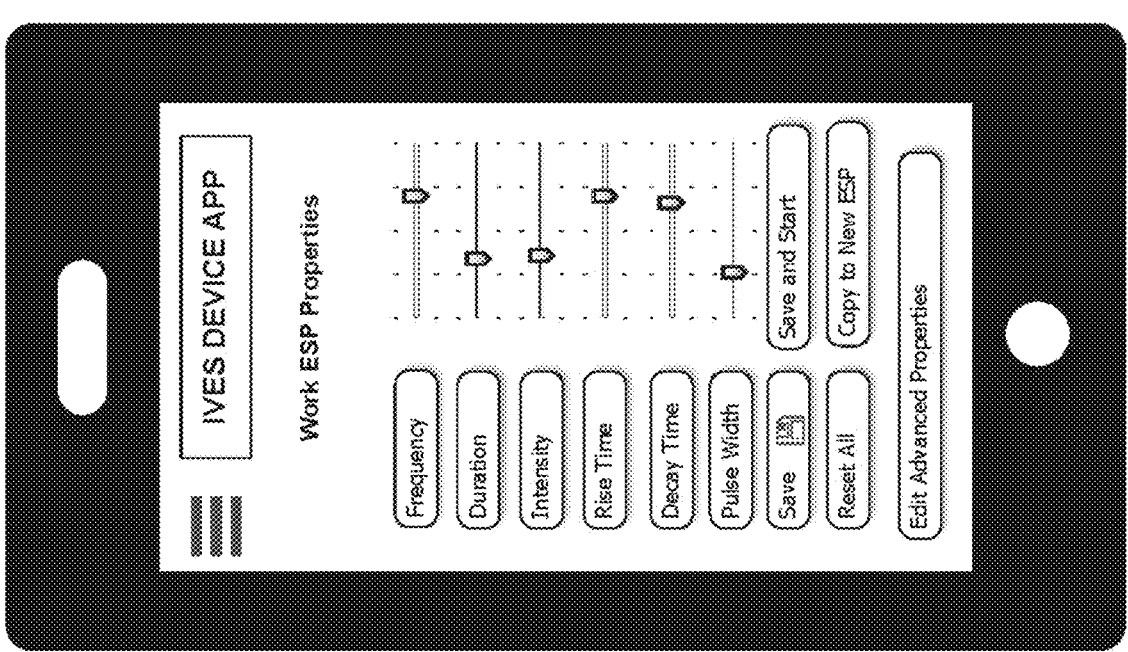
Figure 26A:
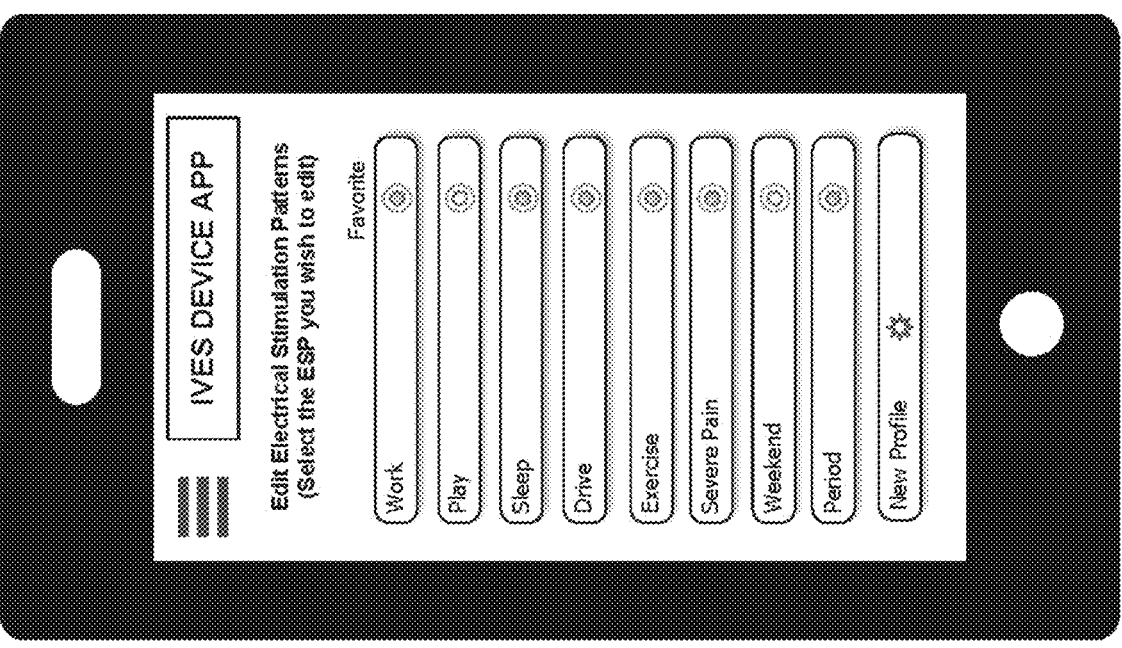
Figure 27B:
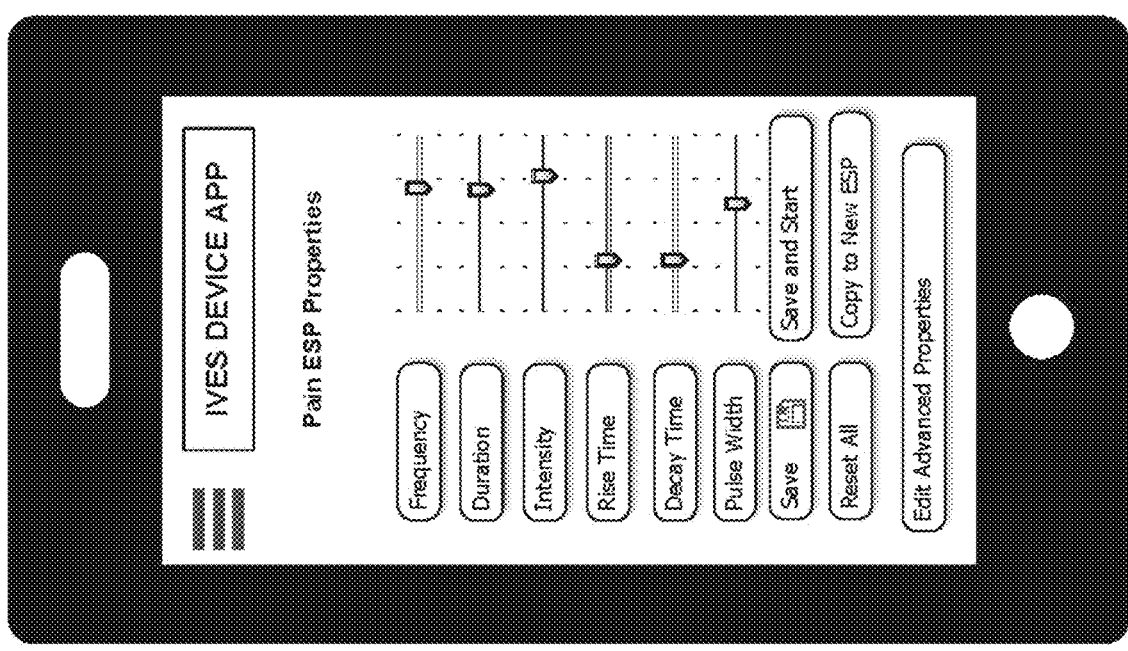
Figure 27A:
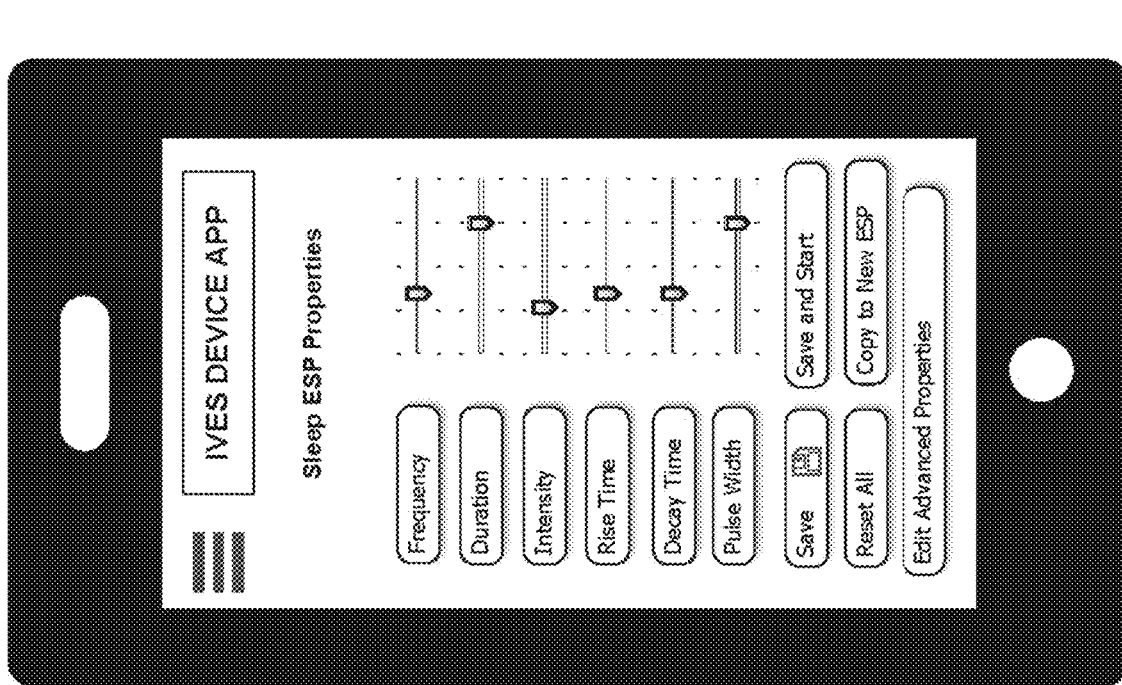

[4] Permitting the patient to choose an electrical stimulation profile (ESP) from a number of "favorited" profiles, which may be (i) pre-loaded into the app during her initial consultation with her IVES practitioner based upon the patient's medical history and the prior treatment experiences of a multiplicity of other users, (ii) loaded into the app following consultations with her IVES practitioner based on her experiences using the IVES device, or (iii) self-created and saved by the patient (FIG. 26A). Each ESP is a predefined combination of specific setting values. The patient may choose her desired ESP with the touch of a button or icon. For example, the patient may have learned that one ESP works best for her while she is at work, a second ESP works best for her when she is at home in the evenings, a third ESP works best for her when she goes to bed, and yet another ESP works best for her when she's exercising. In some embodiments, the data defining the patterns for the ESP's are stored only in the memory of the external controller. In other embodiments, the data defining the patterns for the ESP's may be stored only in the memory of the IVC 102, where they are indexed so that they can be activated by reference to the index number. In still other embodiments, the data defining the patterns for the ESP's are stored in the memories of both the external controller and the IVC 102.

[5] Permitting the patient to create, select, edit and save a variety of different operating properties, such as frequency, intensity, duration, intensity, rise time, decay time and stimulation width of an electrical stimulation session. (FIGS. 26A, 26B, 27A and 27B). Optionally, the patient may also be allowed to adjust advanced settings, such as voltage, amperage and/or waveform to be used during an electrical stimulation session, and anonymously upload her saved ESP properties to a community server, where they may be anonymously accessed and/or downloaded by other users.

Figures 28A, 28B:
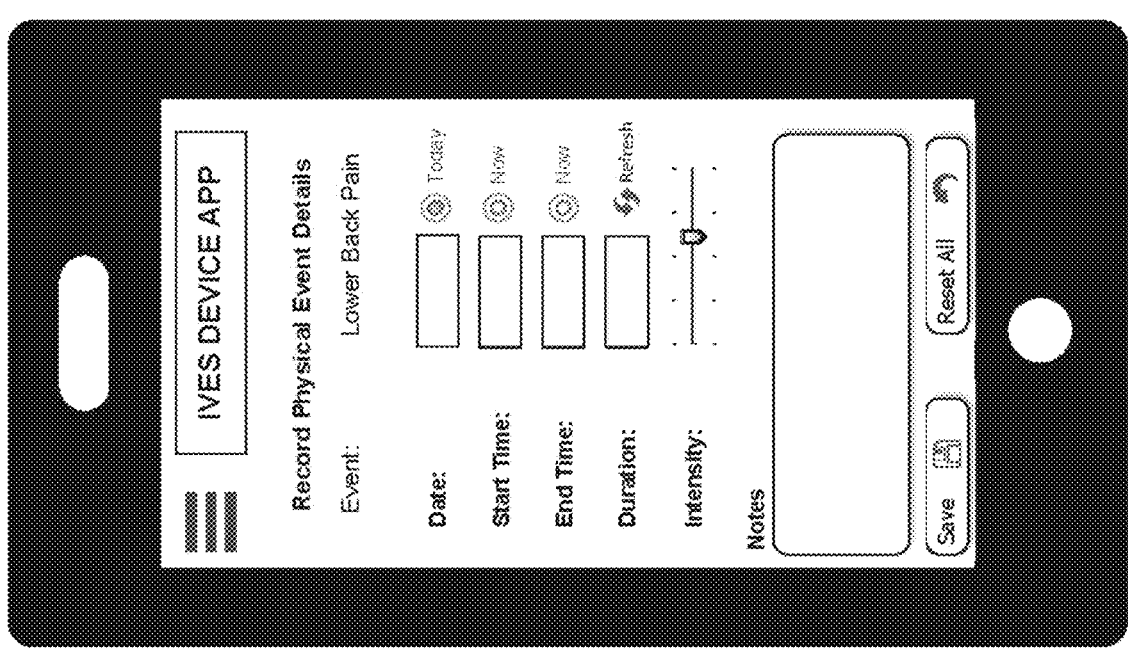

[6] Permitting the patient to track the starting times and ending times of certain physical events in her body, such as the beginning and end of a menstruation period, the beginning and end of menstruation cramps or backaches, the beginning and end of hot flashes or chills, etc., as well as potential side effects or complications that may be associated with the use of the IVES device. (FIGS. 28A and 28B). Suitably, all of the physical event information is stored in the memory of the external controller, automatically synced with the starting and ending times of electrical stimulation sessions (as well as all the settings and properties associated with the sessions), and subsequently uploaded to a computer system operated by herself or her physician or other healthcare provider for subsequent detailed analysis and evaluation of the performance and effectiveness of the IVES device during those events.

Figures 29A, 29B:
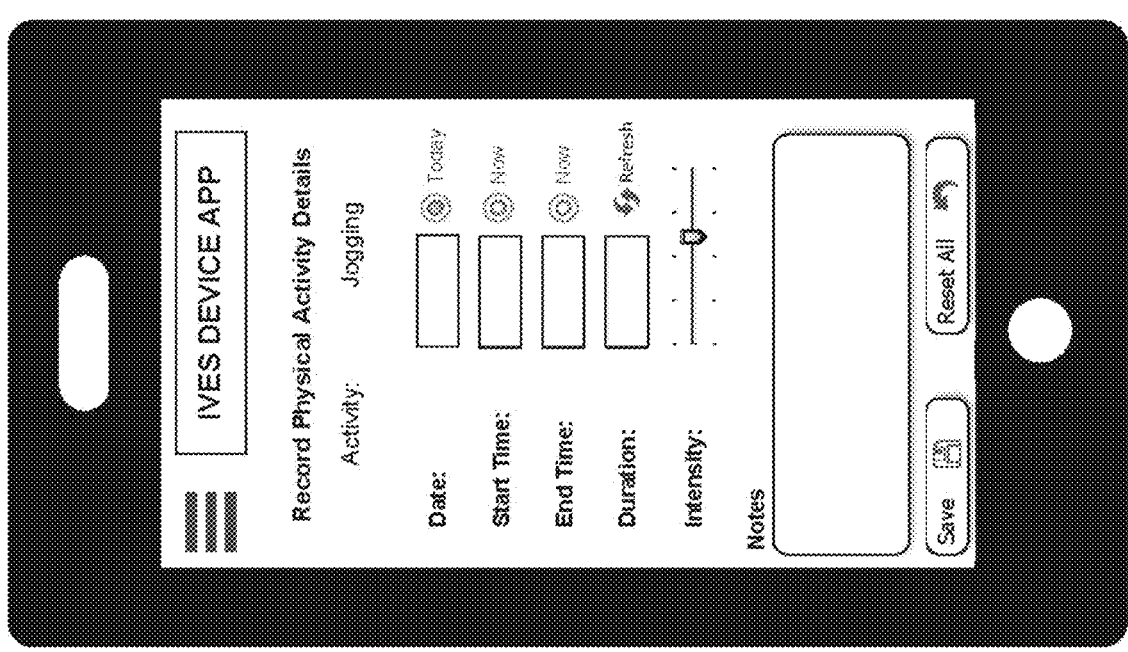

[7] Permitting the patient to track the starting times and ending times of certain physical activities, such as the beginning and end of a physical workout, the beginning and end of intercourse, etc. (FIGS. 29A and 29B). Suitably, all of the physical activity information is also saved in the memory of the external controller, automatically synced with the starting and ending times of electrical stimulation sessions (as well as all the settings and properties associated with the sessions) and the patients response to IVES treatment, and subsequently uploaded to a computer system operated by herself or her physician or other healthcare provider for subsequent detailed analysis and evaluation of the performance and effectiveness of the IVES device during those events.

[8] Permit the patient to automatically send physical event data and physical activity data to her practitioner. (FIG. 25A—"Share Data with Doctor" button).

[9] Permitting the patient to set up and transmit to the local control program on the circuit board of the IVES device a predefined schedule for the IVES device to automatically start and stop a series of electrical stimulation sessions (not shown in the figures).

[10] Whenever an electrical stimulation session is about to begin, providing an audible or visual alert on the patient's external controller or smart phone so that the patient is not surprised by unexpected pelvic stimulation, if any, and will have sufficient time to cancel the session or deactivate the IVES device if the timing of the session is inappropriate for whatever activity in which the patient is currently engaged (not shown in the figures).

[11] At the beginning, during and after an electrical stimulation session, providing an audible or visual alert on the patient's external controller or smart device, along with a prompt to the patient to use a slider or button on the user interface to rate on a scale her current level of pelvic pain and/or discomfort, so that this information can also be tracked, stored and subsequently uploaded to another computer system for detailed analysis and evaluation (not shown in the figures).

[12] Permitting the patient to update the IVES app by checking for available updates on remote computer system and, if any such updates are available, automatically downloading and installing those updates on the external controller (FIG. 25B— "Check for Updates" button.

Figure 30:
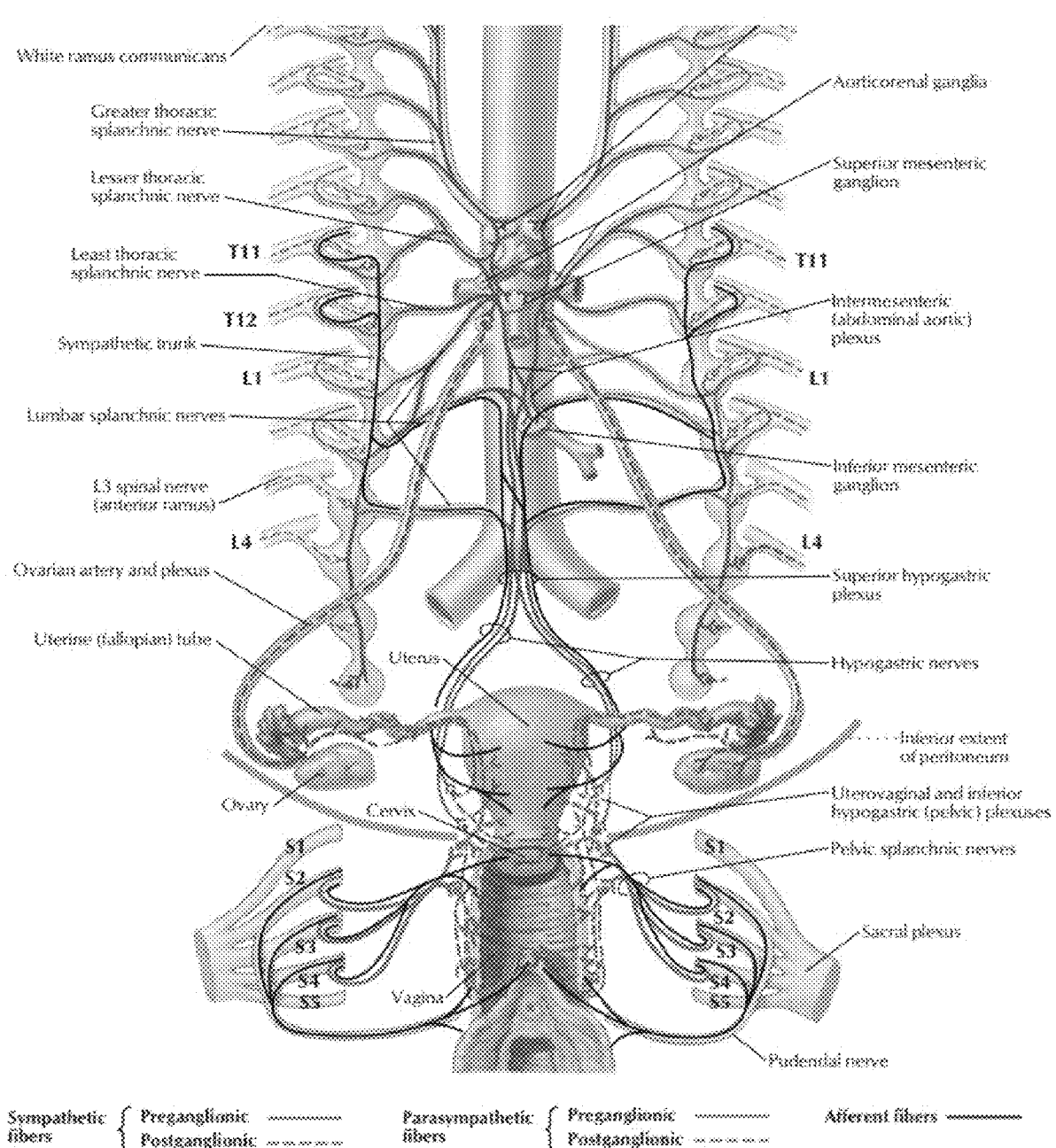
FIG. 30 shows a schematic representation of the nervous innervation of the female reproductive organs.

FIG. 30 shows a schematic representation of the nervous innervation of the female reproductive organs.

Figure 31:
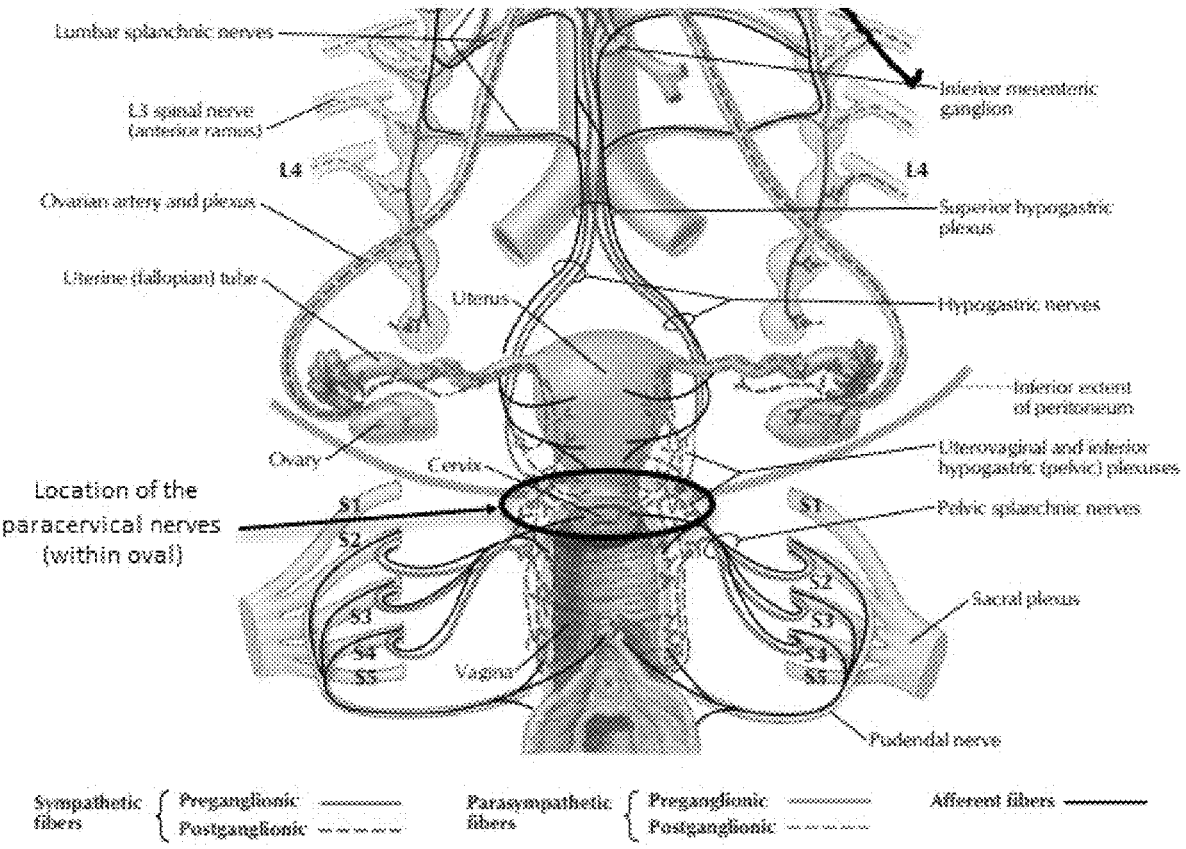
FIG. 31 shows the location of the paracervical nerves on each side of the cervix within the oval surrounding the cervix.

FIG. 31 shows the location of the paracervical nerves on each side of the cervix within the oval surrounding the cervix.

Figure 32:
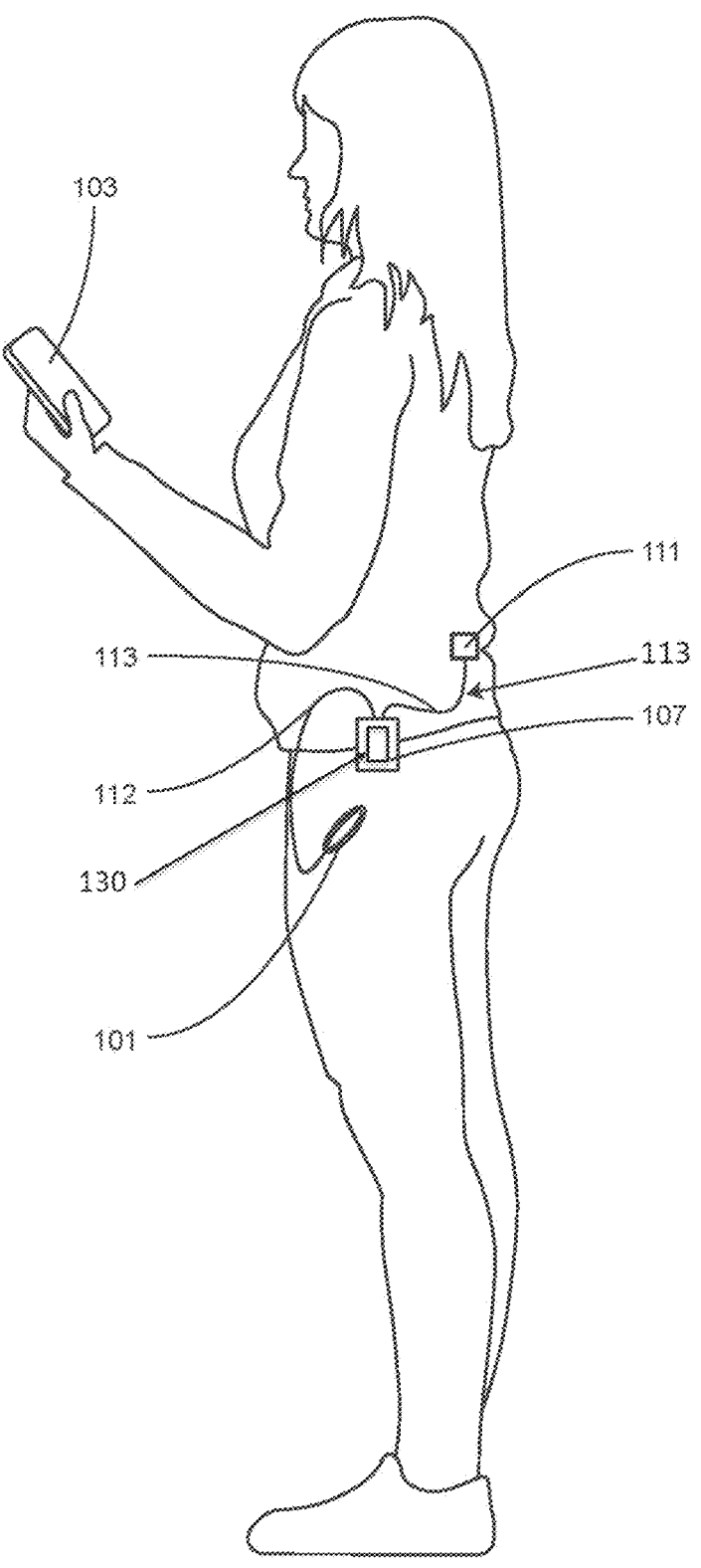
FIG. 32 is a representation of a woman showing the locations of the components of an IVES device in an embodiment in which the ESG is located within an EESG worn externally and a paracervical electrode and a cutaneous electrode are used to create an ESC.

FIG. 32 shows a woman using an embodiment of the present invention in which the ESG 130 is contained inside an EESG 107 that is worn externally on the woman's hip. In this embodiment, the ESC comprises the ESG in the EESG 107, a paracervical electrode 101, a paracervical electrode connecting wire 112 that connects the ESG inside the EESG 107 to the paracervical electrode 101, a cutaneous electrode 111, and a cutaneous electrode connecting wire 113 that connects the cutaneous electrode 111 to the ESG 130 inside the EESG 107. The operation of the EESG 107 is controlled by an external controller 103 in the woman's left hand.

The External Electrical Stimulation Generator

Figure 33A:
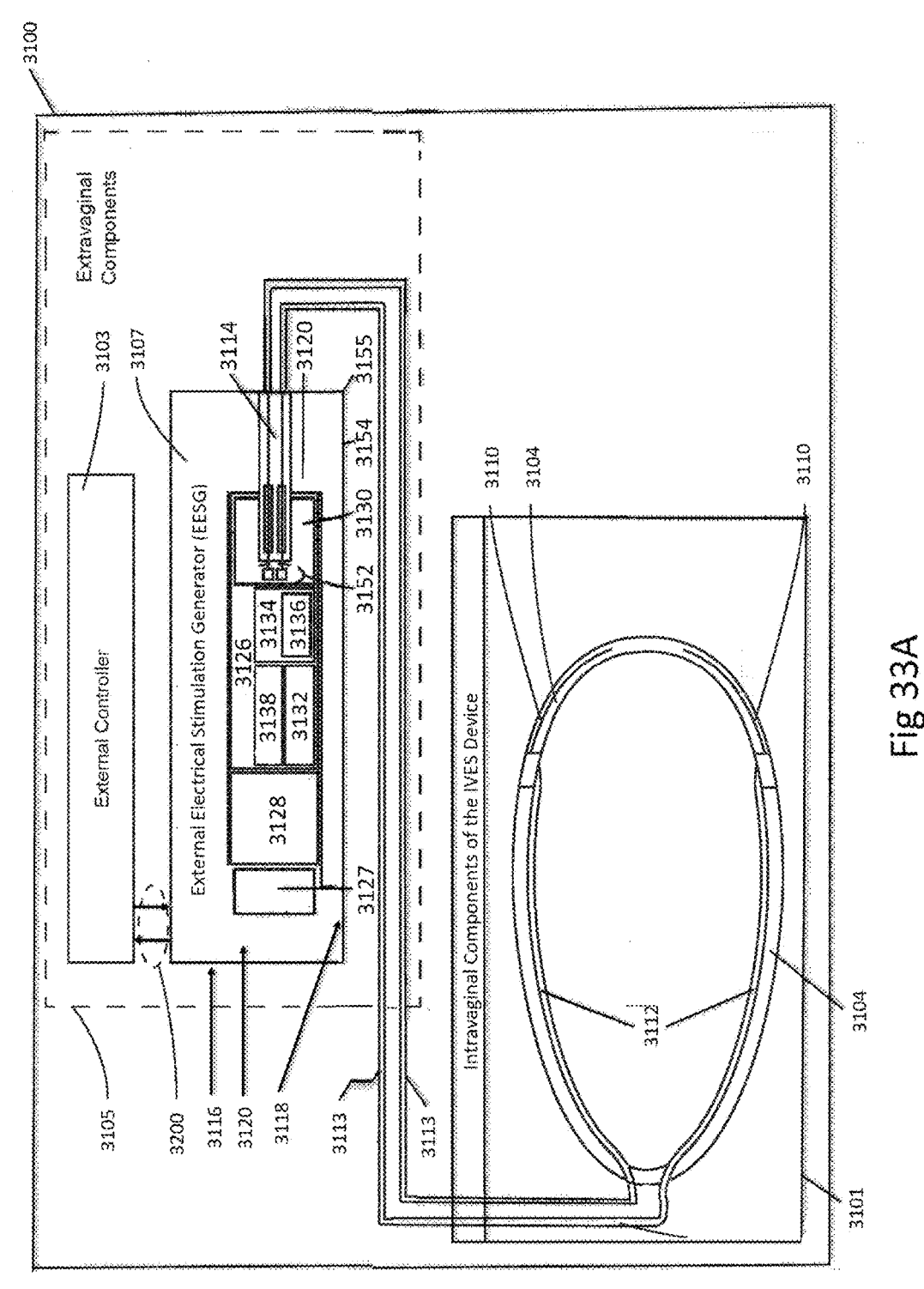
FIG. 33A is an illustration of the components of an embodiment of an IVES device in which an EESG and a pair of paracervical electrodes are used to create an ESC.

FIG. 33A is an illustration of the components of an embodiment of an IVES device 3100, in which the ESG 3130 is contained inside an externally worn EESG 3107. As shown in FIG. 33A, the IVES device 3100 uses a pair of paracervical electrodes 3110 positioned in the lateral vagina fornices (not shown in FIG. 32) to create an electrical field that neuromodulates the pelvic, paracervical and sacral nerves.

The IVES device 3100 comprises a set of intravaginal components 3101 and a set of extravaginal components 3105. The intravaginal components 3101 include the frame 3104, one or more pairs of paracervical electrodes 3110 embedded in the surface material covering the proximal portion of the frame 3104, and one or more pairs of paracervical electrode connecting wires 3112 that exit the vagina through the vaginal orifice. The external components 3106 include, among other things, the external controller 3103, the EESG 3107, and the portion of the paracervical electrode connecting wires 3113 that extend beyond the vaginal orifice and connect to the electrode plug 3114 that is inserted into the socket of the EESG 3107.

The EESG 3107 typically comprises a hard-plastic case 3116 with interior walls 3118 that define an interior cavity 3120 for housing most or all of the electronic parts of the EESG 3107. The electronic components inside the case 3116 of the EESG 3107 may include, for example, a printed circuit board 3126, a rechargeable battery 3128, an inductive charging coil 3127 for charging the rechargeable battery 3128 (or alternatively a location for a commercially available non-rechargeable battery), an electrical stimulation generator 3130, a microprocessor 3132, a memory 3134, a local control program 3136 in the memory 3134, and a radio frequency transceiver 3138. The EESG 3107 is controlled by the external controller 3103.

The Cutaneous Electrodes and Cutaneous Electrode Wires

In other embodiments of the present invention, one of the EUs may terminate at a cutaneous electrode rather than a paracervical electrode. A cutaneous electrode is an electrode that can conduct an electrical current that is attached to the patient's skin. Typically, cutaneous electrodes would be placed on the midline of a woman's lower back in the area of the L5-S1 vertebral junction, but some women may find that they get pain relief by placing cutaneous electrodes in other areas of their pelvis or lower abdomen. A cutaneous electrode connecting wire is an insulated wire that electrically connects a cutaneous electrode to the electrode plug. If an IVES device is configured to use multiple cutaneous electrodes, then that device will suitably require multiple cutaneous electrode connecting wires.

Figure 33B:
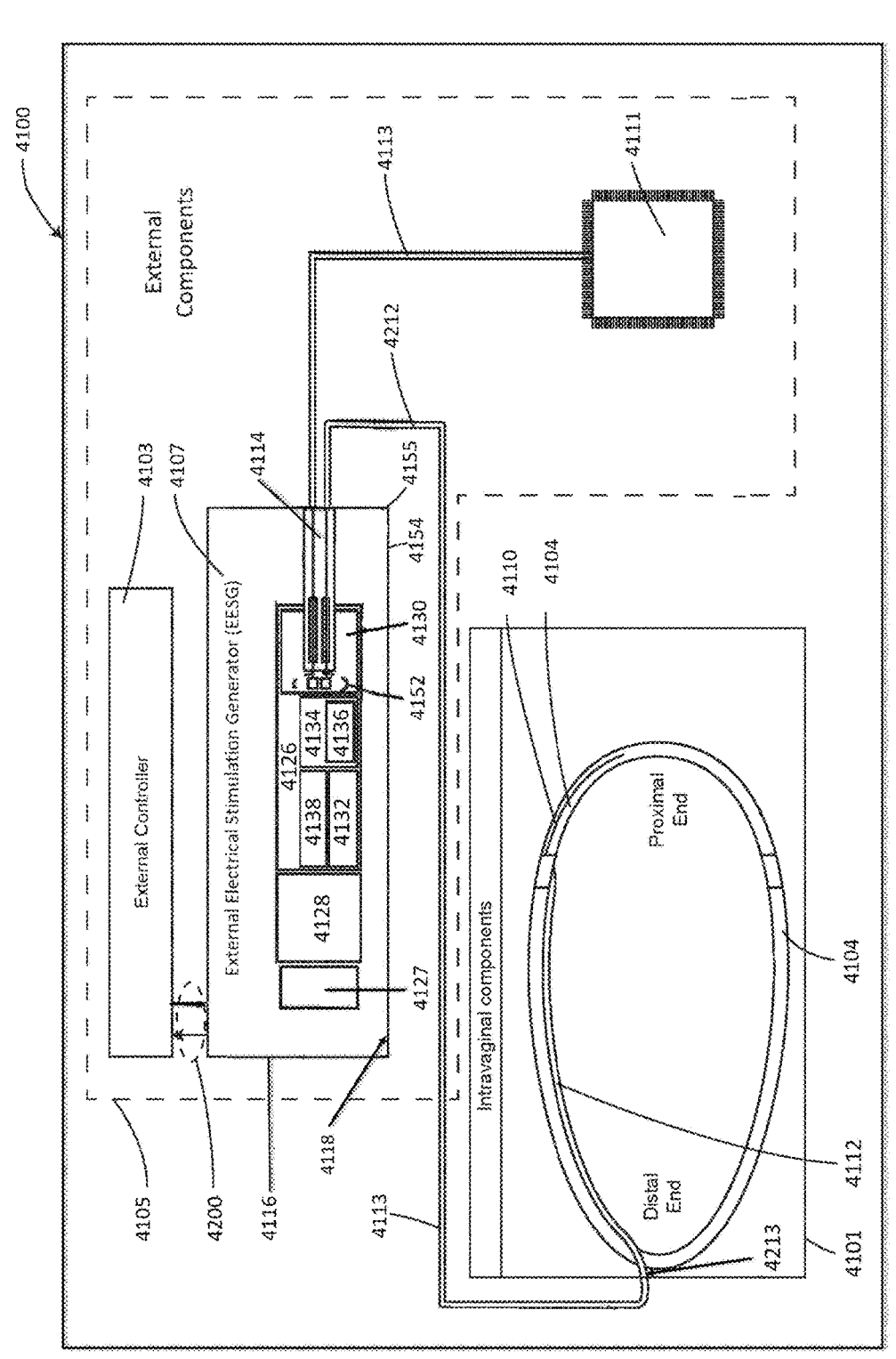
FIG. 33B is an illustration of the components of an embodiment of an IVES device in which an EESG, a paracervical electrode and a cutaneous electrode are used to create an ESC.

FIG. 33B is an illustration of the components of an embodiment of an IVES device 4100, in which the ESG 4130 is contained inside an externally worn EESG 4107. As shown in FIG. 33B, The IVES device 4100 uses an ESC in which one of the EUs in the ESC terminates at a paracervical electrode 4110 positioned in the woman's vagina and the second EU in the ESC terminates at a cutaneous electrode 4111 attached to the woman's skin. When the ESG 4130 is activated an electrical field (not shown in FIG. 33B) is created between the paracervical electrode 4110 and the cutaneous electrode 4111 that neuromodulates the intrapelvic nerves.

The IVES device 4100 comprises a set of intravaginal components 4101, a set of external components 4105. The intravaginal components 4101 include the frame 4104, a paracervical electrode 4110 embedded in the surface material covering the proximal portion of the frame 4110, and a paracervical electrode connecting wire 4212 that exits the vagina through the vaginal orifice (not shown). The external components 4105 include, among other things, and an external controller 4103, the EESG 4107, and the portion of the paracervical electrode connecting wire 4212 that extends beyond the vaginal orifice and connects to the electrode plug 4114 that is inserted into the socket of the EESG 4107.

The EESG 4107 typically comprises a hard-plastic case 4116, and the case 4116 has interior walls 4118 that define an interior cavity 4120 for housing most or all of the electronic parts of the EESG 4107. The electronic components inside the case 4116 of the EESG 4107 may include, for example, a printed circuit board 4126, a rechargeable battery 4128, an inductive charging coil 4127 for charging the rechargeable battery 4128 (or alternatively a location for a commercially available nonchargeable battery), an electrical stimulation generator 4130, a microprocessor 4132, a memory 4134, a local control program 4136 in the memory 4134, and a radio frequency transceiver 4138.

The EESG 4107 is controlled by the external controller 4103.

Figure 33C:
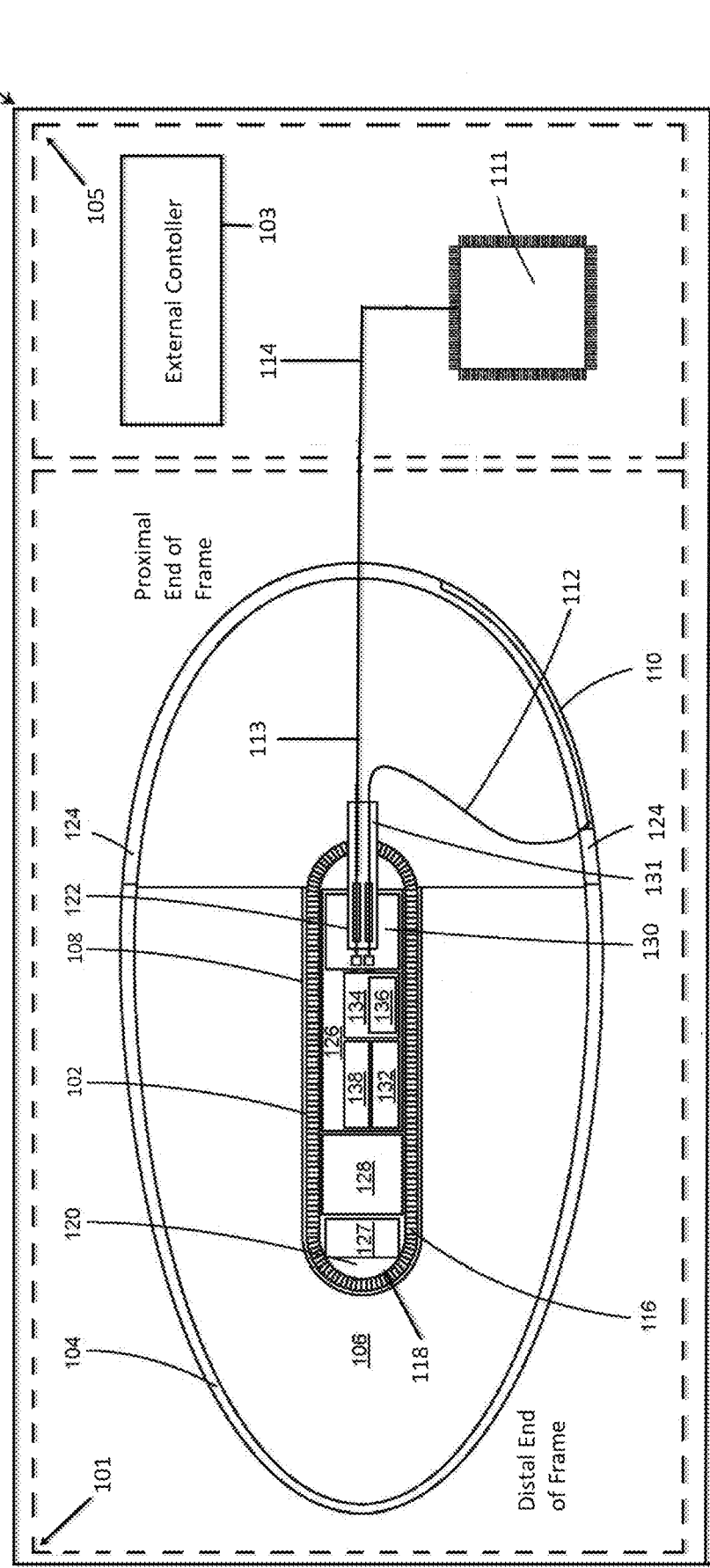
FIG. 33C is an illustration of the components of embodiments of an IVES device in which an IVC, a paracervical electrode and a cutaneous electrode are used to create an ESC.

FIG. 33C is an illustration of the components of an embodiment of an IVES device 100, in which the ESG 130 is contained inside an IVC 102. As shown in FIG. 33C, the IVES device 100 uses an ESC in which one of the EUs in the ESC terminates at a paracervical electrode 110 positioned in the woman's vagina and the second EU in the ESC terminates at a cutaneous electrode 111 attached to the woman's skin. When the ESG 130 is activated an electrical field (not shown in FIG. 33C) is created between the paracervical electrode 110 and the cutaneous electrode 111 that neuromodulates the intrapelvic nerves.

The IVES device 100 comprises a set of intravaginal components 101 and a set of external components 105. The intravaginal components 101 include the frame 104, a paracervical electrode 110 embedded in the surface material covering the proximal portion of the frame 124, and a paracervical electrode connecting wire 112 and the intravaginal portion of a cutaneous electrode connecting wire 113 that connects to the electrode plug 131 and exits the vagina through the vaginal orifice. The external components 105 include, among other things, an external controller 103, a cutaneous electrode and the portion of the cutaneous electrode connecting wire 114 that extend beyond the vaginal orifice to the cutaneous electrode 111.

The IVC 102 typically comprises a hard-plastic shell 116 having interior walls 118 that define an interior cavity 120 for housing most or all of the electronic parts of the IVC 102. The electronic components inside the shell 116 of the IVC 102 may include, for example, a printed circuit board 126, a rechargeable battery 128, an inductive charging coil 127 for charging the rechargeable battery 128, an electrical stimulation generator 130, a microprocessor 132, a memory 134, a local control program 136 in the memory 134, and a radio frequency transceiver 138. The operation of the IVC 102 is typically monitored and controlled by the external controller 103.

Figure 34:
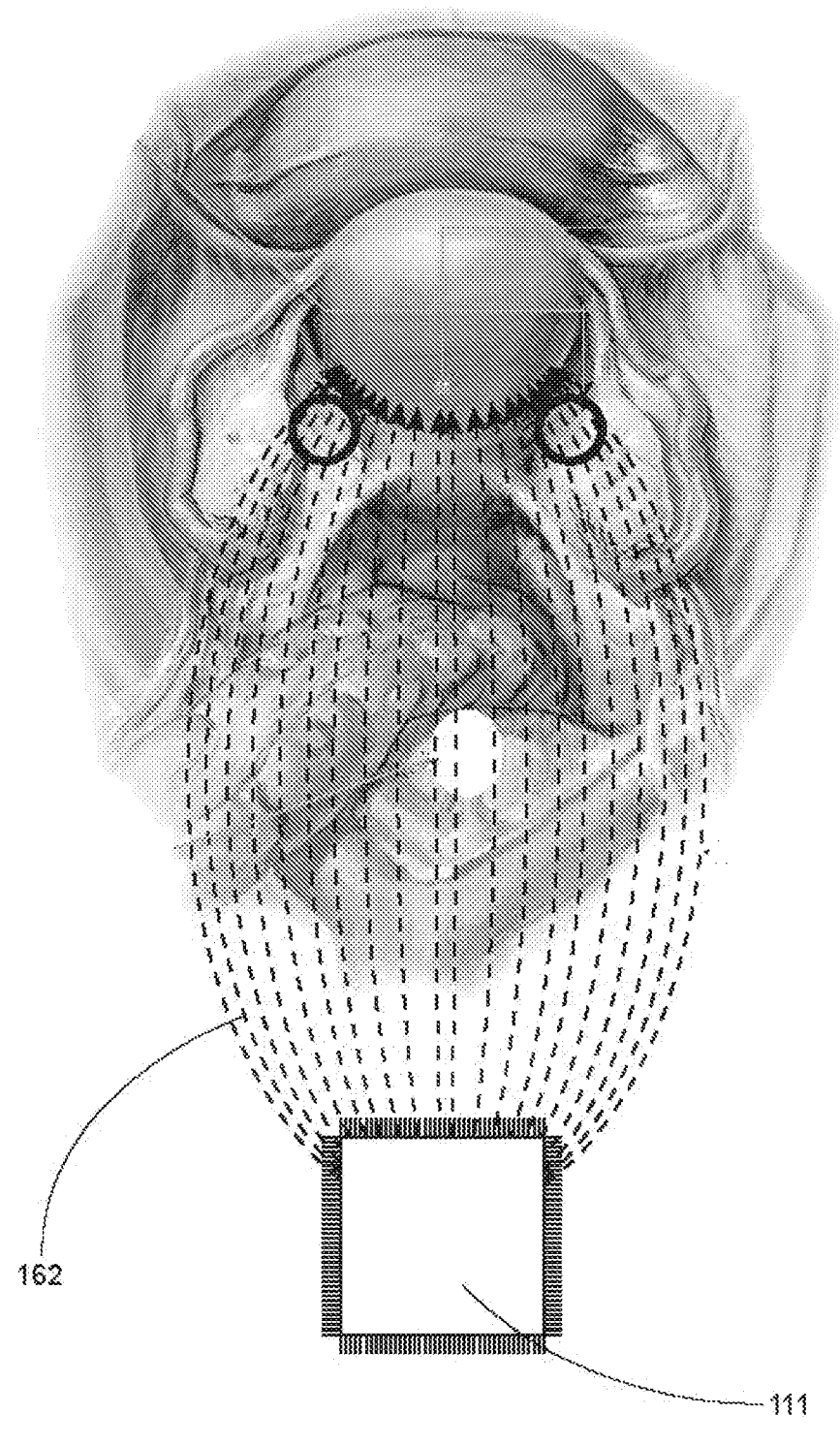
FIG. 34 shows a top-view and intrapelvic view of the electrical field created by an ESC comprised of a paracervical electrode in a lateral vaginal fornix and a cutaneous electrode applied to the midline of the lower back at the level of the L5-S1 vertebral junction.

FIGS. 34 and 35 illustrate the electrical field created by an ESC created between a paracervical electrode electrodes located in the lateral fornices and a cutaneous electrode placed at the L5-S1 vertebral junction is seen from a top intrapelvic view (FIG. 34) and a midline side view (FIG. 35), respectively. This electrical field would have a more significant electrical neuromodulating effect on the nerves traversing the superior hypogastric plexus and the hypogastric nerves than an electrical field (or fields) created between paracervical electrodes located only in the lateral vaginal fornices.

Notably, those skilled in the art will recognize and appreciate that, in various embodiments of the present invention, a variety of differing and potentially overlapping electrical fields can be created and activated simultaneously or sequentially by plugging multiple electrical contacts (connected to differing pairs of paracervical electrodes and/or cutaneous electrodes) in the electrode plug into the socket of the IVC or EESG to produce multiple ESCs. The creation of multiple differing and potentially overlapping electrical fields simultaneously, sequentially and/or in alternating fashion allows for the creation of customized electrical stimulation profiles for individual patients for treating pelvic and external genital pain. Three examples of the types of different electrical fields that may be simultaneously or sequentially activated are shown in FIGS. 22, 23, 34 and 35.

The components of embodiments of the present invention may be arranged and positioned in a variety of different configurations to achieve different patterns of electrical neuromodulation the intrapelvic nerves. For example, in a first embodiment as illustrated in FIGS. 14 and 15E, all of the components of the IVES device, including the IVC, the paracervical electrodes, the frame and all of the contacts and connecting wires there between are positioned inside the vagina when the device is in use, and create electrical fields to electrically neuromodulate the intrapelvic nerves.

In a second embodiment illustrated in FIG. 33A, the ESG 3130 of the IVES device 3100 is contained in an externally worn EESG 3107, with connecting wires that connect the ESG 3130 to a pair of intravaginal paracervical electrodes

3110 to electrically neuromodulate the intrapelvic nerves with electrical fields as illustrated, for example, in FIGS. 20 and 22.

In a third embodiment illustrated in FIG. 33B, the ESG 4130 is contained in an externally worn EESG 4107, and connected to a paracervical electrode 4110 located inside the vagina and a cutaneous electrode 4111 placed on the patient's skin. This embodiment creates and uses an electrical field, as illustrated best in FIGS. 34 and 35, to electrically neuromodulate the intrapelvic nerves.

In a fourth embodiment illustrated in FIG. 33C, the ESG 130 in an IVC 102 is located in the IVC pouch 108 on the frame 104 that is positioned inside the vagina. The IVC 102 is connected to a paracervical electrode 110 positioned on the proximal end of the frame 104, and a cutaneous electrode 111 located on the skin of the patient's body (not shown). This embodiment creates an electrical field as illustrated in FIGS. 34 and 35 to electrically neuromodulate the intrapelvic nerves.

Protocols for Using the IVES Device

It is anticipated that IVES devices constructed in accordance with certain embodiments of the present invention will be available to obtain from medical practitioners who are familiar with the causes and treatments of pelvic pain, female anatomy and physiology. These practitioners are preferably specifically trained on the custom fitting of the IVES devices, the use of electrical stimulation for the treatment of pelvic pain and the proper programming of settings for individual patients using the IVES device. Medical practitioners with the above-mentioned knowledge and training will hereinafter be referred to as "IVES Practitioners."

Evaluation of Candidates for the IVES Device

Appropriate candidates for using IVES devices according to the present invention include, but are not limited to, women with a documented history of endometriosis, dysmenorrhea, dyspareunia or chronic pelvic pain that is not associated with the presence of abdominal or pelvic malignancy. Prior to providing a woman with a device, she should have a complete gynecological examination including a pelvic examination and appropriate screening for cervical dysplasia or cancer and vaginal or pelvic infections. In addition, she should not have any contraindications to the use of electrical stimulation such as the presence of a pacemaker.

Initial Fitting of the Device by an IVES Practitioner

Because every woman's pelvic anatomy is unique and the goal of treatment with the IVES device is to comfortably apply electrical stimulation to the intrapelvic nerves beneath the paracervical vaginal epithelium in the areas of the lateral vaginal fornices, it is important that users of the device be properly fitted for its proper use.

Proper fitting of the intravaginal components 101 of the IVES device 100 requires the selection of a frame 104 that is the appropriately sized for the patient with adjustment made to the shape of the frame 104 if indicated.

Initial Programming of an IVES Device

It is anticipated that individual patients will have several optimal Electrical Stimulation Profiles (ESP's) for the electrical stimulation that is delivered by the IVES device for different circumstances. Circumstances such as activity, time of day, the presence or absence of stress and the level of pelvic pain being experienced by the patient make one ESP preferable over another from time to time. The settings established in each ESP may include adjustments to a variety of parameters such as electrical intensity, stimulation frequency, electrical stimulation waveform, duration of treatment and others.

The initial ESPs made available to the patient may be established in consultation with her IVES practitioner based upon the patient's medical history and the aggregated experiences of numerous patients using the IVES device.

During her initial consultation with an IVES practitioner, the patient will receive an introduction to the use of the IVES device, the external controller, the IVES app, the initially available ESPs, the sensations and feelings that should be avoided during the use of the IVES device and method of recording events through the IVES app.

During the initial consultation or a subsequent one, the patient will receive instruction regarding the creation of "personalized" user defined ESPs created and made available to her through the IVES app.

While the present invention has been disclosed with reference to certain embodiments, numerous modifications, alterations and changes to the disclosed embodiments are possible without departing from the scope of the present invention, as defined in the appended claims. Accordingly, it is not intended that the present invention be limited to the described embodiments, but that it has the full scope defined by the language of the following claims, and equivalents thereof.

What is claimed is:

1. A device for treating pelvic pain in a female patient, comprising:

a set of intravaginal components including a frame having a distal portion and a proximal portion, the frame being configured so that when the set of intravaginal components are inserted into the vagina of the female patient, the proximal portion of the frame will be in contact with the paracervical vaginal epithelium of the posterior and the lateral vaginal fornices of the female patient;

a paracervical electrode attached to the proximal portion of the frame;

a cutaneous electrode configured to be attached the skin of the female patient;

an intravaginal capsule comprising a distal end, a proximal end, a microprocessor, a memory and an electrical stimulation generator communicatively connected to the microprocessor;

a socket in the proximal portion of the intravaginal capsule;

an electrode plug that plugs into the socket in the intravaginal capsule to establish an electrical connection with the electrical stimulation generator;

a first connecting wire that electrically couples the electrode plug to the paracervical electrode;

a second connecting wire that electrically couples the electrode plug to the cutaneous electrode; and a local control program in the memory comprising program instructions that, when executed by the microprocessor, will cause the microprocessor to generate and send control signals to the electrical stimulation generator, the control signals being configured to cause the electrical stimulation generator to apply a voltage to the first connecting wire;

wherein, the voltage applied to the first connecting wire causes a low voltage electrical current to flow through the socket, the electrode plug, the first connecting wire, the paracervical electrode, the cutaneous electrode and the second connecting wire, and the low-voltage electrical current creates an electrical field between the paracervical electrode and the cutaneous electrode, the electric field passes through the paracervical vaginal epithelium of the posterior and the lateral vaginal fornices of the female patient to cause neuromodulation of intrapelvic nerves in the female patient.

2. The device of claim 1, wherein the intrapelvic nerves neuromodulated by the electrical field include the pelvic nerves in the pelvis of the female patient.

3. The device of claim 1, wherein the intrapelvic nerves neuromodulated by the electrical field include the paracervical nerves in the pelvis of the female patient.

4. The device of claim 1, wherein the intrapelvic nerves neuromodulated by the electrical field include the sacral nerves of the female patient.

5. The device of claim 4, wherein the sacral nerves neuromodulated by the electrical field include nerves that innervate the lower vagina and external genitalia of the female patient.

6. The device of claim 1, further comprising:

a sling attached to the frame; and a pouch molded into the sling;

wherein the pouch is configured to receive and hold the distal end of the intravaginal capsule.

7. The device of claim 1, further comprising:

a first radio frequency transceiver located inside the intravaginal capsule; and program instructions in the local control program that, when executed by the microprocessor, will cause the microprocessor to cause the first radio frequency transceiver to establish a data communications channel with an external controller and to receive, via the data communications channel, a remote-control instruction to control operation of the electrical stimulation generator in the intravaginal capsule.

8. The device of claim 7, further comprising the external controller.

9. The device of claim 8, wherein the external controller comprises a second radio frequency transceiver configured to transmit the remote-control instruction from the external controller to the first radio frequency transceiver located inside the intravaginal capsule.

10. The device of claim 7, wherein:

the external controller further comprises a second microprocessor and a memory storage area;

the memory storage area stores a remote-control application and an electrical stimulation pattern; and the remote control application comprises program instructions that, when executed by the second microprocessor on the external controller, will cause the second microprocessor to send a control signal to the microprocessor inside the intravaginal capsule, the control signal being configured to cause the microprocessor in the intravaginal capsule to cause the electrical stimulation generator inside the intravaginal capsule to apply the voltage to the first connecting wire in a manner that causes the low voltage electrical current and the electrical field to vary according to the electrical stimulation pattern stored in the memory storage area of the external controller.

11. The device of claim 10, wherein the remote control program on the external controller further comprises a user interface module, stored in the memory storage area on the external controller, the user interface module having program instructions that, when executed by the second microprocessor on the external controller, will cause the second microprocessor to receive an operating instruction from the female patient.

* * * * *